US012043629B2

(12) United States Patent
Darwish et al.

(10) Patent No.: US 12,043,629 B2
(45) Date of Patent: Jul. 23, 2024

(54) RIP1K INHIBITORS

(71) Applicant: Rigel Pharmaceuticals, Inc., Indianapolis, IN (US)

(72) Inventors: Ihab Darwish, San Carlos, CA (US); Zhushou Luo, San Jose, CA (US); Vanessa Taylor, San Francisco, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 18/154,255

(22) Filed: Jan. 13, 2023

(65) Prior Publication Data

US 2023/0227469 A1 Jul. 20, 2023

Related U.S. Application Data

(62) Division of application No. 17/221,493, filed on Apr. 2, 2021, now Pat. No. 11,584,758.

(60) Provisional application No. 63/004,404, filed on Apr. 2, 2020.

(51) Int. Cl.
*C07D 498/04* (2006.01)
*A61K 9/00* (2006.01)
*C07D 471/04* (2006.01)
*C07D 519/00* (2006.01)

(52) U.S. Cl.
CPC .......... *C07D 498/04* (2013.01); *A61K 9/0053* (2013.01); *C07D 471/04* (2013.01); *C07D 519/00* (2013.01)

(58) Field of Classification Search
CPC ................................... C07D 498/04
USPC ..................................... 514/210.16
See application file for complete search history.

(56) References Cited

U.S. PATENT DOCUMENTS

| 8,658,689 | B2 | 2/2014 | Cuny et al. |
| 9,556,152 | B2 | 1/2017 | Harris |
| 9,624,202 | B2 | 4/2017 | Jeong |
| 9,725,452 | B2 | 8/2017 | Yuan et al. |
| 9,815,850 | B2 | 11/2017 | Estrada |
| 9,896,458 | B2 | 2/2018 | Estrada et al. |
| 10,815,206 | B2 | 10/2020 | Masuda et al. |
| 10,975,064 | B2 | 4/2021 | Taylor et al. |
| 10,988,459 | B2 | 4/2021 | Patel et al. |
| 11,407,736 | B2 | 8/2022 | Chen et al. |
| 11,584,758 | B2 * | 2/2023 | Darwish ............... A61P 17/00 |
| 2021/0069208 | A1 | 3/2021 | Yu et al. |
| 2021/0070735 | A1 | 3/2021 | Bhamidipati et al. |
| 2021/0070744 | A1 | 3/2021 | Shaw et al. |
| 2021/0139494 | A1 | 5/2021 | Chen et al. |
| 2021/0292340 | A1 | 9/2021 | Ma et al. |
| 2021/0317135 | A1 | 10/2021 | Darwish et al. |
| 2021/0371430 | A1 | 12/2021 | Zhou et al. |
| 2022/0009936 | A1 | 1/2022 | Bhamidipati et al. |

FOREIGN PATENT DOCUMENTS

| WO | 2016027253 | 2/2016 |
| WO | 2016128936 | 8/2016 |
| WO | 2017064217 | 4/2017 |
| WO | 2017069279 | 4/2017 |
| WO | 2017109724 | 6/2017 |
| WO | 2018073193 | 4/2018 |
| WO | 2018109097 | 6/2018 |
| WO | 2018154520 | 8/2018 |
| WO | 2020001420 | 1/2020 |
| WO | 2020088194 | 5/2020 |

OTHER PUBLICATIONS

Harris, et al., "Identification of a RIP1 Kinase Inhibitor Clinical Candidate (GSK3145095) for the Treatment of Pancreatic Cancer," ACS Med. Chem. Lett., vol. 10, No. 6, pp. 857-862 (May 9, 2019).
Harris, et al., "Discovery and Lead-Optimization of 4,5-Dihydropyrazoles as Mono-Kinase Selective, Orally Bioavailable and Efficacious Inhibitors of Receptor Interacting Protein 1 (RIP1) Kinase," Journal of Medicinal Chemistry, vol. 62, No. 10, pp. 5096-5110 (Apr. 23, 2019).
Shii, et al., "CETSA quantitatively verifieds in vivo target engagement of novel RIPK1 inhibitors in various biospeciments," Scientific Reports, vol. 7, No. 13000, pp. 1-14 (Oct. 12, 2017).
Najjar, et al., "Structure guided design of potent and selective ponatinib-based hybrid inhibitors for RIPK1," Cell Reports, vol. 10, pp. 1850-1860 (Mar. 24, 2015).
Yoshikawa, et al., "Discovery of 7-Oxo-2,4,5,7-tetrahydro-6 H-pyrazolo [3,4-C] pyridine Derivatives as Potent, Orally Available, and Brian-Penetrating Receptor Interacting Protein 1 (RIP1) Kinase Inhibitors: Analysis of Structure-Kinetic Relationships," Journal of Medicinal Chemistry, vol. 61, No. 6, pp. 2384-2409 (2018).
Harris, et al., "DNA-Encoded Library Screening Identifies Benzo[b][1,4]oxazepin-4-ones as Highly Potent and Monoselective Receptor Interacting Protein 1 Kinase Inhibitors," Journal of Medicinal Chemistry, vol. 59, No. 5, pp. 2163-2178 (Mar. 10, 2016).
Harris, et al., "Discovery of a First-in-Class Receptor Interacting Protein 1 (RIP1) Kinase Specific Clinical Candidate (GSK2982772) for the Treatment of Inflammatory Diseases," Journal of Medicinal Chemistry, vol. 60, pp. 1247-1261 (2017).
International Search Report for PCT Application No. PCT/US2020/049527.
Written Opinion for PCT Application No. PCT/US2020/049527.

* cited by examiner

*Primary Examiner* — Niloofar Rahmani
(74) *Attorney, Agent, or Firm* — Gabriel Magallanes

(57) ABSTRACT

Disclosed herein are kinase inhibitory compounds, such as a receptor-interacting protein-1 (RIP1) kinase inhibitor compounds, as well as pharmaceutical compositions and combinations comprising such inhibitory compounds. The disclosed compounds, pharmaceutical compositions, and/or combinations may be used to treat or prevent a kinase-associated disease or condition, particularly a RIP1-associated disease or condition.

5 Claims, No Drawings

RIP1K INHIBITORS

FIELD

The present disclosure concerns compounds and methods of making and using the compounds, such as for inhibiting receptor-interacting protein-1 kinase ("RIP1"), and for treating diseases and/or conditions related to RIP1.

BACKGROUND

Receptor-interacting protein-1 kinase (referred to herein as "RIP1") belongs to the tyrosine kinase-like family and is a serine/threonine protein kinase involved in innate immune signaling. RIP1 plays a central role in regulating cell signaling and its role in programmed cell death has been linked to various inflammatory diseases, such as inflammatory bowel disease, psoriasis, and other diseases and/or conditions associated with inflammation and/or necroptotic cell death.

SUMMARY

Disclosed herein are compounds according to Formula I

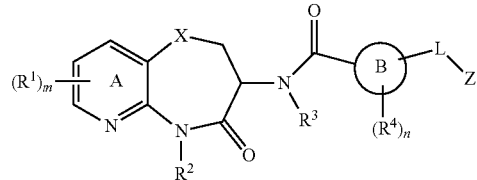

wherein ring B is 5-membered or 6-membered heteroaryl;
X is $CH_2$ or O;
L is a heteroatom or $R^a$, provided that $R^a$ is not hydrogen;
Z is $C_{1-10}$aliphatic (such as $C_{1-10}$alkyl, $C_{2-10}$ alkenyl, $C_{2-10}$ alkynyl, $C_{3-6}$ cycloalkyl); aryl or heteroaryl, each optionally substituted with one or more $R^5$ group;
$R^1$ is independently for each occurrence —$NR^dR^d$ wherein the two $R^d$ groups together with the nitrogen bound thereto provide a $C_{3-10}$heterocyclic group; —C≡CH, or a -linker-$R^6$ group, wherein the linker is a divalent $C_{1-10}$aliphatic moiety (such as $C_{1-10}$alkyl, $C_{2-10}$ alkenyl, $C_{2-10}$ alkynyl) or $C_{1-10}$cycloaliphatic moiety, and $R^6$ is $R^b$, —$C(R^f)_3$, or —$C(R^f)$=$C(R^f)_2$; $C_{5-10}$aromatic, or $C_{3-6}$heterocyclic, each linker optionally substituted with one or more halo, $R^a$, or both;
$R^2$ and $R^3$ independently are $R^a$ In some embodiments, $R^2$ is hydrogen or $C_{1-10}$aliphatic, such as H or $C_{1-6}$alkyl, and in certain embodiments, $R^2$ is $C_{1-6}$alkyl, such as $CH_3$ or $CD_3$;
$R^4$ and $R^5$ independently are, for each occurrence, $R^e$;
$R^a$ is independently for each occurrence hydrogen, $C_{1-10}$aliphatic (such as $C_{1-10}$alkyl, $C_{2-10}$alkenyl, $C_{2-10}$ alkynyl, or $C_{3-6}$ cycloalkyl), $C_{1-10}$haloaliphatic, $C_{5-10}$aromatic, or $C_{3-6}$heterocyclic;
$R^b$ is independently for each occurrence —OH, —SH, —$OR^c$, —$SR^c$, —$NR^eR^e$, —$Si(R^a)_3$, —C(O)OH, —$C(O)OR^c$, or —$C(O)NR^eR^e$
$R^c$ is independently for each occurrence $C_{1-10}$alkyl (optionally substituted with 1, 2 or 3 $R^e$), $C_{2-10}$alkenyl (optionally substituted with 1, 2 or 3 $R^e$), $C_{2-10}$alkynyl (optionally substituted with 1, 2 or 3 $R^e$), $C_{3-6}$cycloalkyl (optionally substituted with 1, 2 or 3 $R^e$), or $C_{5-10}$aromatic (optionally substituted with 1, 2 or 3 $R^e$);
$R^d$ is $C_{1-9}$aliphatic optionally substituted with 1, 2, or 3 $R^a$, $R^b$ and/or $R^e$ groups;
$R^e$ is independently for each occurrence oxo (=O), —$OR^a$, $N(R^a)_2$, halo, $C_{1-6}$alkyl, $C_{1-6}$haloalkyl, $C_{1-6}$heteroalkyl, $C_{3-6}$ cycloalkyl, or two $R^e$ groups join together to provide a $C_{3-10}$heterocyclic group with a nitrogen to which the two $R^e$ groups are bound;
m is 1 to 4; and
n is 0, 1 or 2.

The foregoing and other objects, features, and advantages of the invention will become more apparent from the following detailed description.

DETAILED DESCRIPTION

I. Overview of Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references, including patents and patent applications cited herein, are incorporated by reference.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is expressly recited.

Unless explained otherwise, all technical and scientific terms used herein have the same meaning as commonly understood to one of ordinary skill in the art to which this disclosure pertains. Although methods and materials similar or equivalent to those described herein can be used in the practice or testing of the present disclosure, suitable methods and materials are described below. The materials, methods, and examples are illustrative only and not intended to be limiting.

As used herein, the term "substituted" refers to all subsequent modifiers in a term, for example in the term "substituted aryl$C_{1-8}$alkyl," substitution may occur on the "$C_{1-8}$alkyl" portion, the "aryl" portion or both portions of the aryl$C_{1-8}$alkyl group.

"Substituted," when used to modify a specified group or moiety, means that at least one, and perhaps two or more, hydrogen atoms of the specified group or moiety is independently replaced with the same or different substituent groups as defined below. In a particular embodiment, a group, moiety or substituent may be substituted or unsubstituted, unless expressly defined as either "unsubstituted" or "substituted." Accordingly, any of the groups specified herein may be unsubstituted or substituted unless the context indicates otherwise or a particular structural formula precludes substitution. In particular embodiments, a substituent may or may not be expressly defined as substituted, but is still contemplated to be optionally substituted. For example, an "aliphatic" or a "cyclic" moiety may be unsubstituted or substituted, but an "unsubstituted aliphatic" or an "unsubstituted cyclic" is not substituted.

"Substituents" or "substituent groups" for substituting for one or more hydrogen atoms on saturated carbon atoms in the specified group or moiety can be, unless otherwise specified, —$R^{60}$, halo, =O, —$OR^{70}$, —$N(R^{80})_2$, haloalkyl, perhaloalkyl, —CN, —$NO_2$, =$N_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$P(O)(O^-)_2(M^+)_2$, —$P(O)(O^-)_2M^{2+}$, —$P(O)(OR^{70})O^-M^+$, —$P(O)(OR^{70})_2$, —$C(O)R^{70}$, —$C(S)R^{70}$, —$C(NR^{70})R^{70}$, —$OCO_2^-M^+$, —$CO_2R^{70}$, —$C(S)OR^{70}$, —$C(O)N(R^{80})_2$, —$C(NR^{70})(R^{80})_2$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70})_2$, —$NR^{70}C(O)N(R^{80})_2$, $NR^{70}C(NR^{70})R^{70}$ and —$NR^{70}C(NR^{70})N(R^{80})_2$, where $R^{60}$ is $C_{1-10}$aliphatic, heteroaliphatic, or cycloaliphatic, typically, $C_{1-6}$aliphatic, more typically $C_{1-6}$alkyl, where $R^{60}$ optionally may be substituted; each $R^{70}$ is independently for each occurrence hydrogen or $R^{60}$; each $R^{80}$ is independently for each occurrence $R^{70}$ or alternatively, two $R^{80}$ groups, taken together with the nitrogen atom to which they are bonded, form a 3- to 7-membered heterocycloaliphatic, which optionally includes from 1 to 4 of the same or different additional heteroatoms selected from O, N and S, of which N optionally has $R^{70}$ substitution, such as H or $C_1$-$C_3$alkyl substitution; and each $M^+$ is a counter ion with a net single positive charge. Each $M^+$ is independently for each occurrence, for example, an alkali metal ion, such as $K^+$, $Na^+$, $Li^+$; an ammonium ion, such as $^+N(R^{60})_4$; a protonated amino acid ion, such as a lysine ion, or an arginine ion; or an alkaline metal earth ion, such as $[Ca^{2+}]_{0.5}$, $[Mg^{2+}]_{0.5}$, or $[Ba^{2+}]_{0.5}$ (a subscript "0.5" means, for example, that one of the counter ions for such divalent alkali earth ions can be an ionized form of a compound of the invention and the other a typical counter ion such as chloride, or two ionized compounds can serve as counter ions for such divalent alkali earth ions, or a doubly ionized compound can serve as the counter ion for such divalent alkali earth ions). As specific examples, —$N(R^{80})_2$ includes —$NH_2$, —NH-alkyl, —NH-pyrrolidin-3-yl, N-pyrrolidinyl, N-piperazinyl, 4N-methyl-piperazin-1-yl, N-morpholinyl and the like. Any two hydrogen atoms on a single carbon also can be replaced with, for example, =O, =$NR^{70}$, =N—$OR^{70}$, =$N_2$ or =S.

Substituent groups for replacing hydrogen atoms on unsaturated carbon atoms in groups containing unsaturated carbons are, unless otherwise specified, —$R^{60}$, halo, —$O^-M^+$, —$OR^{70}$, —$S^-R^+$, —$S^-M^+$, —$N(R^{80})_2$, perhaloalkyl, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}(M^+)_2$, —$PO_3^{-2}M^{2+}$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)NR^{80}R^{80}$, —$C(NR^{70})N(R^{80})_2$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^7C(S)OR^{70}$, —$NR^{70}C(O)N(R^{80})_2$, —$NR^{70}C(NR^{70})R^{70}$ and —$NR^{70}C(NR^{70})N(R^{80})_2$, where $R^{60}$, $R^{70}$, $R^{80}$ and $M^+$ are as previously defined. In an independent embodiment, the substituents are not —$O^-M^+$, —$OR^{70}$, —$SR^{70}$, or —$S^-M^+$.

Substituent groups for replacing hydrogen atoms on nitrogen atoms in groups containing such nitrogen atoms are, unless otherwise specified, —$R^{60}$, —$O^-M^+$, —$OR^{70}$, —$SR^{70}$, —$S^-M^+$, —$N(R^{80})_2$, perhaloalkyl, —CN, —NO, —$NO_2$, —$S(O)_2R^{70}$, —$SO_3^-M^+$, —$SO_3R^{70}$, —$OS(O)_2R^{70}$, —$OSO_3^-M^+$, —$OSO_3R^{70}$, —$PO_3^{2-}(M^+)_2$, —$PO_3^{2-}M^{2+}$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$CO_2R^{70}$, —$C(S)OR^{70}$, —$C(O)NR^8OR^{80}$, —$C(NR^{70})NR^8OR^{80}$, —$OC(O)R^{70}$, —$OC(S)R^{70}$, —$OCO_2R^{70}$, —$OC(S)OR^{70}$, —$NR^{70}C(O)R^{70}$, —$NR^{70}C(S)R^{70}$, —$NR^{70}CO_2R^{70}$, —$NR^{70}C(S)OR^{70}$, —$NR^{70}C(O)N(R^{80})_2$, —$NR^{70}C(NR^{70})R^{70}$ and —$NR^{70}C(NR^{70})N(R^{80})_2$, where $R^{60}$, $R^{70}$, $R^{80}$ and $M^+$ are as previously defined.

In one embodiment, a group that is substituted has at least one substituent up to the number of substituents possible for a particular moiety, such as 1 substituent, 2 substituents, 3 substituents, or 4 substituents.

Additionally, in embodiments where a group or moiety is substituted with a substituted substituent, the nesting of such substituted substituents is limited to three, thereby preventing the formation of polymers. Thus, in a group or moiety comprising a first group that is a substituent on a second group that is itself a substituent on a third group, which is attached to the parent structure, the first (outermost) group can only be substituted with unsubstituted substituents. For example, in a group comprising -(aryl-1)-(aryl-2)-(aryl-3), aryl-3 can only be substituted with substituents that are not themselves substituted.

Any group or moiety defined herein can be connected to any other portion of a disclosed structure, such as a parent or core structure, as would be understood by a person of ordinary skill in the art, such as by considering valence rules, comparison to exemplary species, and/or considering functionality, unless the connectivity of the group or moiety to the other portion of the structure is expressly stated, or is implied by context.

"Acyl" refers to the group —C(O)R, where R is H, aliphatic, heteroaliphatic, or aromatic (including both aryl and heteroaryl). Exemplary acyl moieties include, but are not limited to, —C(O)H, —C(O)alkyl, —C(O)$C_1$-$C_6$alkyl, —C(O)$C_1$-$C_6$haloalkyl, —C(O)cycloalkyl, —C(O)alkenyl, —C(O)cycloalkenyl, —C(O)aryl, —C(O)heteroaryl, or —C(O)heterocyclyl. Specific examples include, —C(O)H, —C(O)Me, —C(O)Et, or —C(O)cyclopropyl.

"Aliphatic" refers to a substantially hydrocarbon-based group or moiety. An aliphatic group or moiety can be acyclic, including alkyl, alkenyl, or alkynyl groups (as well as alkylene, alkenylene, or alkynylene groups), cyclic versions thereof, such as cycloaliphatic groups or moieties including cycloalkyl, cycloalkenyl or cycloalkynyl, and further including straight- and branched-chain arrangements, and all stereo and position isomers as well. Unless expressly stated otherwise, an aliphatic group contains from one to twenty-five carbon atoms ($C_{1-25}$); for example, from one to fifteen ($C_{1-15}$), from one to ten ($C_{1-10}$) from one to six ($C_{1-6}$), or from one to four carbon atoms ($C_{1-4}$) for an acyclic aliphatic group or moiety, or from three to fifteen ($C_{3-15}$) from three to ten ($C_{3-10}$), from three to six ($C_{3-6}$), or from three to four ($C_{3-4}$) carbon atoms for a cycloaliphatic group or moiety. An aliphatic group may be substituted or unsubstituted, unless expressly referred to as an "unsubstituted aliphatic" or a "substituted aliphatic." An aliphatic group can be substituted with one or more substituents (up to two substituents for each methylene carbon in an aliphatic chain, or up to one substituent for each carbon of a —C≡C— double bond in an aliphatic chain, or up to one substituent for a carbon of a terminal methine group).

"Lower aliphatic" refers to an aliphatic group containing from one to ten carbon atoms ($C_{1-10}$), such as from one to six ($C_{1-6}$), or from one to four ($C_{1-4}$) carbon atoms; or from three to ten ($C_{3-10}$), such as from three to six ($C_{3-6}$) carbon atoms for a lower cycloaliphatic group.

"Alkoxy" refers to the group —OR, where R is a substituted or unsubstituted alkyl or a substituted or unsubstituted cycloalkyl group. In certain examples R is a $C_{1-6}$ alkyl group or a $C_{3-6}$cycloalkyl group. Methoxy (—OCH$_3$) and ethoxy (—OCH$_2$CH$_3$) are exemplary alkoxy groups. In a substituted alkoxy, R is substituted alkyl or substituted cycloalkyl, examples of which in the presently disclosed compounds include haloalkoxy groups, such as —OCF$_2$H.

"Alkoxyalkyl" refers to the group -alkyl-OR, where R is a substituted or unsubstituted alkyl or a substituted or unsubstituted cycloalkyl group; —CH$_2$CH$_2$—O—CH$_2$CH$_3$ is an exemplary alkoxyalkyl group.

"Alkyl" refers to a saturated aliphatic hydrocarbyl group having from 1 to at least 25 ($C_{1-25}$) carbon atoms, more typically 1 to 10 ($C_{1-10}$) carbon atoms such as 1 to 6 ($C_{1-6}$) carbon atoms. An alkyl moiety may be substituted or unsubstituted. This term includes, by way of example, linear and branched hydrocarbyl groups such as methyl (CH$_3$), ethyl (—CH$_2$CH$_3$), n-propyl (—CH$_2$CH$_2$CH$_3$), isopropyl (—CH (CH$_3$)$_2$), n-butyl (—CH$_2$CH$_2$CH$_2$CH$_3$), isobutyl (—CH$_2$CH$_2$(CH$_3$)$_2$), sec-butyl (—CH(CH$_3$)(CH$_2$CH$_3$), t-butyl (—C(CH$_3$)$_3$), n-pentyl (—CH$_2$CH$_2$CH$_2$CH$_2$CH$_3$), and neopentyl (—CH$_2$C(CH$_3$)$_3$).

"Amino" refers to the group —NH$_2$, —NHR, or —NRR, where each R independently is selected from H, aliphatic, heteroaliphatic, aromatic, including both aryl and heteroaryl, or heterocycloaliphatic, or two R groups together with the nitrogen attached thereto form a heterocyclic ring. Examples of such heterocyclic rings include those wherein two R groups together with the nitrogen to which they are attached form a —(CH$_2$)$_{2-5}$— ring optionally interrupted by one or two heteroatom groups, such as —O— or —N(R$^9$) such as in the groups

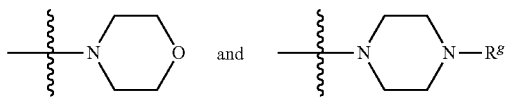

wherein R$^g$ is R$^{70}$, —C(O)R$^{70}$, —C(O)OR$^{60}$ or —C(O)N (R$^{80}$)$_2$.

"Amide" refers to the group —N(R)acyl, wherein R is hydrogen, heteroaliphatic, or aliphatic, such as alkyl, particularly $C_{1-6}$alkyl.

"Aromatic" refers to a cyclic, conjugated group or moiety of, unless specified otherwise, from 5 to 15 ring atoms having a single ring (e.g., phenyl, pyridinyl, or pyrazolyl) or multiple condensed rings in which at least one ring is aromatic (e.g., naphthyl, indolyl, or pyrazolopyridinyl), that is at least one ring, and optionally multiple condensed rings, have a continuous, delocalized 7-electron system. Typically, the number of out of plane π-electrons corresponds to the Hückel rule (4n+2). The point of attachment to the parent structure typically is through an aromatic portion of the condensed ring system. For example,

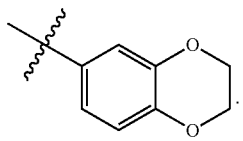 [SMILES: *c1ccc2c(c1)OCCO2]

However, in certain examples, context or express disclosure may indicate that the point of attachment is through a non-aromatic portion of the condensed ring system. For example,

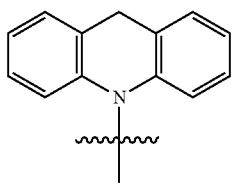

An aromatic group or moiety may comprise only carbon atoms in the ring, such as in an aryl group or moiety, or it may comprise one or more ring carbon atoms and one or more ring heteroatoms comprising a lone pair of electrons (e.g. S, O, N, P, or Si), such as in a heteroaryl group or moiety. Unless otherwise stated, an aromatic group may be substituted or unsubstituted.

"Aryl" refers to an aromatic carbocyclic group of, unless specified otherwise, from 6 to 15 carbon atoms having a single ring (e.g., phenyl) or multiple condensed rings in which at least one ring is aromatic (e.g., 1,2,3,4-tetrahydroquinoline, benzodioxole, and the like). If any aromatic ring portion contains a heteroatom, the group is heteroaryl and not aryl. Aryl groups may be, for example, monocyclic, bicyclic, tricyclic or tetracyclic. Unless otherwise stated, an aryl group may be substituted or unsubstituted.

"Aralyphatic" refers to an aryl group attached to the parent via an aliphatic moiety. Aralyphatic includes aralkyl or arylalkyl groups such as benzyl and phenylethyl.

"Carboxyl" refers to —CO$_2$H.

"Carboxamide" refers to —C(O)amino.

"Carboxyl ester" or "carboxy ester" refers to the group —C(O)OR, where R is aliphatic, heteroaliphatic, or aromatic (including both aryl and heteroaryl).

"Carboxylate" refers to —C(O)O— or salts thereof.

"Cyano" refers to the group —CN.

"Cycloaliphatic" refers to a cyclic aliphatic group having a single ring (e.g., cyclohexyl), or multiple rings, such as in a fused, bridged or spirocyclic system, the ring or at least one of the rings in the system is aliphatic. Typically, the point of attachment to the parent structure is through an aliphatic portion of the multiple ring system. Cycloaliphatic includes saturated and unsaturated systems, including cycloalkyl, cycloalkenyl and cycloalkynyl. A cycloaliphatic group may contain from three to twenty-five carbon atoms; for example, from three to fifteen, from three to ten, or from three to six carbon atoms. Unless otherwise stated, a cycloaliphatic group may be substituted or unsubstituted. Exemplary cycloaliphatic groups include, but are not limited to, cyclopropyl, cyclobutyl, cyclopentyl, cyclohexyl, cycloheptyl, cyclopentenyl, or cyclohexenyl.

"Halo," "halide" or "halogen" refers to fluoro, chloro, bromo or iodo.

"Haloalkyl" refers to an alkyl moiety substituted with one or more halogens. Exemplary haloalkyl moieties include —CH$_2$F, —CHF$_2$ and —CF$_3$.

"Heteroaliphatic" refers to an aliphatic compound or group having at least one heteroatom and at least one carbon atom, i.e., at least one carbon atom from an aliphatic compound or group comprising at least two carbon atoms, has been replaced with an atom having at least one lone pair of electrons, typically nitrogen, oxygen, phosphorus, silicon, or sulfur. Heteroaliphatic compounds or groups may be substituted or unsubstituted, branched or unbranched, chiral or achiral, and/or acyclic or cyclic, such as a heterocycloaliphatic group.

"Heteroaryl" refers to an aromatic group or moiety having, unless specified otherwise, from 5 to 15 ring atoms comprising at least one carbon atom and at least one heteroatom, such as N, S, O, P, or Si. A heteroaryl group or moiety may comprise a single ring (e.g., pyridinyl, pyrimidinyl or pyrazolyl) or multiple condensed rings (e.g., indolyl, benzopyrazolyl, or pyrazolopyridinyl). A heteroaryl group may contain one or more non-aromatic rings fused to an aromatic moiety and such heteroaryl groups may be linked to the remainder of the molecule through an aromatic or non-aromatic ring. Heteroaryl groups or moiety may be, for example, monocyclic, bicyclic, tricyclic or tetracyclic. Unless otherwise stated, a heteroaryl group or moiety may be substituted or unsubstituted.

"Heterocyclyl," "heterocyclo" and "heterocycle" refer to both aromatic and non-aromatic ring systems, and more specifically refer to a stable three- to fifteen-membered ring moiety comprising at least one carbon atom, and typically plural carbon atoms, and at least one, such as from one to five, heteroatoms. The heteroatom(s) may be nitrogen, phosphorus, oxygen, silicon or sulfur atom(s). The heterocyclyl moiety may be a monocyclic moiety, or may comprise multiple rings, such as in a bicyclic or tricyclic ring system, provided that at least one of the rings contains a heteroatom. Such a multiple ring moiety can include fused or bridged ring systems as well as spirocyclic systems; and any nitrogen, phosphorus, carbon, silicon or sulfur atoms in the heterocyclyl moiety can be optionally oxidized to various oxidation states. For convenience, nitrogens, particularly, but not exclusively, those defined as annular aromatic nitrogens, are meant to include their corresponding N-oxide form, although not explicitly defined as such in a particular example. Thus, for a compound having, for example, a pyridinyl ring, the corresponding pyridinyl-N-oxide is included as another compound of the invention, unless expressly excluded or excluded by context. In addition, annular nitrogen atoms can be optionally quaternized. Heterocycle includes heteroaryl moieties, and heteroalicyclyl or heterocycloaliphatic moieties, which are heterocyclyl rings that are partially or fully saturated. Examples of heterocyclyl groups include, but are not limited to, azetidinyl, oxetanyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, diazabicycloheptane, diazapane, diazepine, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Hydroxyl" refers to the group —OH.

"Nitro" refers to the group —NO$_2$.

"Phosphate" refers to the group —O—P(O)(OR')$_2$, where each —OR' independently is —OH; —O-aliphatic, such as —O-alkyl or —O-cycloalkyl; —O-aromatic, including both —O-aryl and —O-heteroaryl; —O-aralkyl; or —OR' is —O$^-$M$^+$, where M$^+$ is a counter ion with a single positive charge. Each M$^+$ may be an alkali ion, such as K$^+$, Na$^+$, Li$^+$; an ammonium ion, such as $^+$N(R")$_4$ where R" is H, aliphatic, heteroaliphatic, or aromatic (including both aryl and heteroaryl); or an alkaline earth ion, such as [Ca$^{2+}$]$_{0.5}$, [Mg$^{2+}$]$_{0.5}$, or [Ba$^{2+}$]$_{0.5}$. Phosphonooxyalkyl refers to the group -alkyl-phosphate, such as, for example, —CH$_2$OP(O)(OH)$_2$, or a salt thereof, such as —CH$_2$OP(O)(O$^-$Na$^+$)$_2$, and (((dialkoxyphosphoryl)oxy)alkyl) refers to the dialkyl ester of a phosphonooxyalkyl group, such as, for example, —CH$_2$OP(O)(O-tert-butyl)$_2$.

"Phosphonate" refers to the group —P(O)(OR')$_2$, where each —OR' independently is —OH; —O-aliphatic such as —O-alkyl or —O-cycloalkyl; —O-aromatic, including both —O-aryl and —O-heteroaryl; or —O-aralkyl; or —OR' is —O$^-$M$^+$, and M$^+$ is a counter ion with a single positive charge. Each M$^+$ is a positively charged counterion and may be, by way of example, an alkali metal ion, such as K$^+$, Na$^+$, Li$^+$; an ammonium ion, such as $^+$N(R")$_4$ where R" is H, aliphatic, heteroaliphatic, or aromatic (including both aryl and heteroaryl); or an alkaline earth metal ion, such as [Ca$^{2+}$]$_{0.5}$, [Mg$^{2+}$]$_{0.5}$, or [Ba$^{2+}$]$_{0.5}$. Phosphonoalkyl refers to the group -alkyl-phosphonate, such as, for example, —CH$_2$P(O)(OH)$_2$, or —CH$_2$P(O)(O$^-$Na$^+$)$_2$, and ((dialkoxyphosphoryl)alkyl) refers to the dialkyl ester of a phosphonoalkyl group, such as, for example, —CH$_2$P(O)(O-tert-butyl)$_2$.

"Patient" or "Subject" may refer generally to any living being, but more typically refers to mammals and other animals, particularly humans. Thus disclosed methods are applicable to both human therapy and veterinary applications.

"Pharmaceutically acceptable excipient" refers to a substance, other than the active ingredient, that is included in a composition comprising the active ingredient. As used herein, an excipient may be incorporated within particles of a pharmaceutical composition, or it may be physically mixed with particles of a pharmaceutical composition. An excipient can be used, for example, to dilute an active agent and/or to modify properties of a pharmaceutical composition. Excipients can include, but are not limited to, antiadherents, binders, coatings, enteric coatings, disintegrants, flavorings, sweeteners, colorants, lubricants, glidants, sorbents, preservatives, carriers or vehicles. Excipients may be starches and modified starches, cellulose and cellulose derivatives, saccharides and their derivatives such as disaccharides, polysaccharides and sugar alcohols, protein, synthetic polymers, crosslinked polymers, antioxidants, amino acids or preservatives. Exemplary excipients include, but are not limited to, magnesium stearate, stearic acid, vegetable stearin, sucrose, lactose, starches, hydroxypropyl cellulose, hydroxypropyl methylcellulose, xylitol, sorbitol, maltitol, gelatin, polyvinylpyrrolidone (PVP), polyethyleneglycol (PEG), tocopheryl polyethylene glycol 1000 succinate (also known as vitamin E TPGS, or TPGS), carboxy methyl cellulose, dipalmitoyl phosphatidyl choline (DPPC), vitamin A, vitamin E, vitamin C, retinyl palmitate, selenium, cysteine, methionine, citric acid, sodium citrate, methyl paraben, propyl paraben, sugar, silica, talc, magnesium carbonate, sodium starch glycolate, tartrazine, aspartame, benzalkonium chloride, sesame oil, propyl gallate, sodium metabisulphite or lanolin.

An "adjuvant" is a component that modifies the effect of other agents, typically the active ingredient. Adjuvants are often pharmacological and/or immunological agents. An adjuvant may modify the effect of an active ingredient by increasing an immune response. An adjuvant may also act as a stabilizing agent for a formulation. Exemplary adjuvants include, but are not limited to, aluminum hydroxide, alum, aluminum phosphate, killed bacteria, squalene, detergents, cytokines, paraffin oil, and combination adjuvants, such as Freund's complete adjuvant or Freund's incomplete adjuvant.

"Pharmaceutically acceptable carrier" refers to an excipient that is a carrier or vehicle, such as a suspension aid, solubilizing aid, or aerosolization aid. *Remington: The Science and Practice of Pharmacy*, The University of the Sciences in Philadelphia, Editor, Lippincott, Williams, & Wilkins, Philadelphia, PA, 21$^{st}$ Edition (2005), incorporated herein by reference, describes exemplary compositions and formulations suitable for pharmaceutical delivery of one or more therapeutic compositions and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

"Pharmaceutically acceptable salt" refers to pharmaceutically acceptable salts of a compound that are derived from a variety of organic and inorganic counter ions as will be known to a person of ordinary skill in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. "Pharmaceutically acceptable acid addition salts" are a subset of "pharmaceutically acceptable salts" that retain the biological effectiveness of the free bases while formed by acid partners. In particular, the disclosed compounds form salts with a variety of pharmaceutically acceptable acids, including, without limitation, inorganic acids such as hydrochloric acid, hydrobromic acid, sulfuric acid, nitric acid, phosphoric acid, and the like, as well as organic acids such as amino acids, formic acid, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, benzene sulfonic acid, isethionic acid, methanesulfonic acid, ethanesulfonic acid, p-toluenesulfonic acid, salicylic acid, xinafoic acid and the like. "Pharmaceutically acceptable base addition salts" are a subset of "pharmaceutically acceptable salts" that are derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, tris(hydroxymethyl)aminomethane (Tris), ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, tris(hydroxymethyl)aminomethane (Tris), ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.) In particular disclosed embodiments, the compounds may be a formate, trifluoroactate, hydrochloride or sodium salt.

"Effective amount" with respect to a compound or pharmaceutical composition refers to an amount of the compound or pharmaceutical composition sufficient to achieve a particular desired result, such as to inhibit a protein or enzyme. In particular embodiments, an "effective amount" is an amount sufficient to inhibit RIP1; to elicit a desired biological or medical response in a tissue, system, subject or patient; to treat a specified disorder or disease; to ameliorate or eradicate one or more of its symptoms; and/or to prevent the occurrence of the disease or disorder. The amount of a compound which constitutes an "effective amount" may vary depending on the compound, the desired result, the disease state and its severity, the size, age, and gender of the patient to be treated and the like, as will be understood by a person of ordinary skill in the art.

"Prodrug" refers to compounds that are transformed in vivo to yield a biologically active compound, or a compound more biologically active than the parent compound. In vivo transformation may occur, for example, by hydrolysis or enzymatic conversion. Common examples of prodrug moieties include, but are not limited to, ester and amide forms of a compound having an active form bearing a carboxylic acid moiety. Examples of pharmaceutically acceptable esters of the compounds of this invention include, but are not limited to, esters of phosphate groups and carboxylic acids, such as aliphatic esters, particularly alkyl esters (for example $C_{1-6}$alkyl esters). Other prodrug moieties include phosphate esters, such as —$CH_2$—O—$P(O)(OR')_2$ or a salt thereof, wherein R' is H or $C_{1-6}$alkyl. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of disclosed exemplary embodiments of compounds according to the present invention can be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Solvate" refers to a complex formed by combination of solvent molecules with molecules or ions of a solute. The solvent can be an organic solvent, an inorganic solvent, or a mixture of both. Exemplary solvents include, but are not limited to, alcohols, such as methanol, ethanol, propanol; amides such as N,N-dialiphatic amides, such as N,N-dimethylformamide; tetrahydrofuran; alkylsulfoxides, such as dimethylsulfoxide; water; and combinations thereof. The compounds described herein can exist in un-solvated as well as solvated forms when combined with solvents, pharmaceutically acceptable or not, such as water, ethanol, and the like. Solvated forms of the presently disclosed compounds are within the scope of the embodiments disclosed herein.

"Sulfonamide" refers to the group or moiety —SO$_2$amino, or —N(R)sulfonyl, where R is H, aliphatic, heteroaliphatic, or aromatic (including both aryl and heteroaryl).

"Sulfanyl" refers to the group or —SH, —S-aliphatic, —S-heteroaliphatic, —S-aromatic, (including both-S-aryl and —S-heteroaryl).

"Sulfinyl" refers to the group or moiety —S(O)H, —S(O)aliphatic, —S(O)heteroaliphatic, or —S(O)aromatic (including both —S(O)aryl and —S(O)heteroaryl).

"Sulfonyl" refers to the group: —SO$_2$H, —SO$_2$aliphatic, —SO$_2$heteroaliphatic, —SO$_2$aromatic (including both —SO$_2$aryl and —SO$_2$heteroaryl).

"Treating" or "treatment" as used herein concerns treatment of a disease or condition of interest in a patient or subject, particularly a human having the disease or condition of interest, and includes by way of example, and without limitation:

(i) preventing the disease or condition from occurring in a patient or subject, in particular, when such patient or subject is predisposed to the condition but has not yet been diagnosed as having it;

(ii) inhibiting the disease or condition, for example, arresting or slowing its development;

(iii) relieving the disease or condition, for example, causing diminution of a symptom or regression of the disease or condition or a symptom thereof; or (iv) stabilizing the disease or condition.

As used herein, the terms "disease" and "condition" can be used interchangeably or can be different in that the particular malady or condition may not have a known causative agent (so that etiology has not yet been determined) and it is therefore not yet recognized as a disease but only as an undesirable condition or syndrome, where a more or less specific set of symptoms have been identified by clinicians.

The above definitions and the following general formulas are not intended to include impermissible substitution patterns (e.g., methyl substituted with 5 fluoro groups). Such impermissible substitution patterns are easily recognized by a person having ordinary skill in the art.

A person of ordinary skill in the art will appreciate that compounds may exhibit the phenomena of tautomerism, conformational isomerism, geometric isomerism, and/or optical isomerism. For example, certain disclosed compounds can include one or more chiral centers and/or double bonds and as a consequence can exist as stereoisomers, such as double-bond isomers (i.e., geometric isomers), enantiomers, diasteromers, and mixtures thereof, such as racemic mixtures. As another example, certain disclosed compounds can exist in several tautomeric forms, including the enol form, the keto form, and mixtures thereof. As the various compound names, formulae and compound drawings within the specification and claims can represent only one of the possible tautomeric, conformational isomeric, optical isomeric, or geometric isomeric forms, a person of ordinary skill in the art will appreciate that the disclosed compounds encompass any tautomeric, conformational isomeric, optical isomeric, and/or geometric isomeric forms of the compounds described herein, as well as mixtures of these various different isomeric forms. Mixtures of different isomeric forms, including mixtures of enantiomers and/or stereoisomers, can be separated to provide each separate enantiomers and/or stereoisomer using techniques known to those of ordinary skill in the art, particularly with the benefit of the present disclosure. In cases of limited rotation, e.g. around the amide bond or between two directly attached rings such as pyridinyl rings, biphenyl groups, and the like, atropisomers are also possible and are also specifically included in the compounds of the invention.

As is understood by those of skill in the art, hydrogen may be present in any of three isotopes, namely, protium, deuterium and tritium. In certain embodiments, any or all hydrogens present in the compound, or in a particular group or moiety within the compound, may be enriched in deuterium or tritium relative to the natural abundance for such isotopes. Thus, a recitation of alkyl includes compounds that are enriched in deuterium relative to protium. A deuterated alkyl group, may have one or more protium atoms replaced by deuterium. For example, ethyl refers to both C$_2$H$_5$ or C$_2$H$_5$ where from 1 to 5 protium atoms are replaced by deuterium, such as in C$_2$D$_x$H$_{5-x}$.

II. RIP1-Active Compounds and Pharmaceutical Compositions Comprising RIP1-Active Compounds A. Compounds Disclosed herein are compounds and pharmaceutical compositions comprising such compounds that are useful for inhibiting RIP1 and/or for treating diseases and/or conditions associated with RIP1. In some embodiments, the compounds are selective kinase inhibitors. For example, exemplary compounds inhibit RIP1 over RIP2, RIP3, or both RIP2 and RIP3. In some embodiments, a compound of the present disclosure can have a structure satisfying Formula I

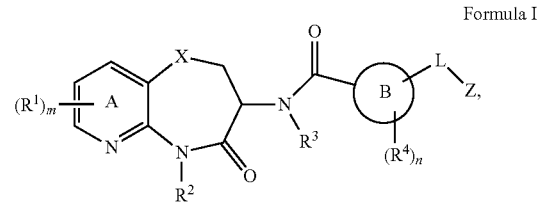

Formula I

A person of ordinary skill in the art will appreciate that the disclosed formulas herein include within their scope all hydrates, solvates, physical forms, stereoisomers, N-oxides, tautomers, and prodrugs of the illustrated compounds.

With reference to Formula I:
ring B is 5-membered or 6-membered heteroaryl;
X is CH$_2$ or O;
L is a heteroatom or R$^a$, provided that R$^a$ is not hydrogen;
Z is C$_{1-10}$aliphatic (such as C$_{1-10}$alkyl, C$_{2-10}$alkenyl, C$_{2-10}$alkynyl, C$_{3-6}$cycloalkyl); aryl or heteroaryl, each optionally substituted with one or more R$^5$ group;

R¹ is independently for each occurrence —NR$^d$R$^d$ wherein the two R$^d$ groups together with the nitrogen bound thereto provide a C$_{3-10}$heterocyclic group; —C≡CH, or a -linker-R$^6$ group, wherein the linker is a divalent C$_{1-10}$aliphatic moiety (such as C$_{1-10}$alkyl, C$_{2-10}$alkenyl, C$_{2-10}$alkynyl) or C$_{1-10}$cycloaliphatic moiety, and R$^6$ is R$^b$, —C(R$^f$)$_3$, or —C(R$^f$)=C(R$^f$)$_2$; C$_{5-10}$aromatic, or C$_{3-6}$heterocyclic, each linker optionally substituted with one or more halo, R$^a$, or both;

R² and R³ independently are R$^a$ In some embodiments, R² is hydrogen or C$_{1-10}$aliphatic, such as H or C$_{1-6}$alkyl, and in certain embodiments, R² is C$_{1-6}$alkyl, such as CH$_3$ or CD$_3$;

R⁴ and R⁵ independently are, for each occurrence, R$^e$;

R$^a$ is independently for each occurrence hydrogen, C$_{1-10}$aliphatic (such as C$_{1-10}$alkyl, C$_{2-10}$alkenyl, C$_{2-10}$alkynyl, or C$_{3-6}$cycloalkyl), C$_{1-10}$haloaliphatic, C$_{5-10}$aromatic, or C$_{3-6}$heterocyclic;

R$^b$ is independently for each occurrence —OH, —SH, —OR$^c$, —SR$^c$, —NR$^e$R$^e$, —Si(R$^a$)$_3$, —C(O)OH, —C(O)OR$^c$, or —C(O)NR$^e$R$^e$ R$^c$ is independently for each occurrence C$_{1-10}$alkyl (optionally substituted with 1, 2 or 3 R$^e$), C$_{2-10}$alkenyl (optionally substituted with 1, 2 or 3 R$^e$), C$_{2-10}$alkynyl (optionally substituted with 1, 2 or 3 R$^e$), C$_{3-6}$cycloalkyl (optionally substituted with 1, 2 or 3 R$^e$), or C$_{5-10}$aromatic (optionally substituted with 1, 2 or 3 R$^e$);

R$^d$ is C$_{1-9}$aliphatic optionally substituted with 1, 2, or 3 R$^a$, R$^b$ and/or R$^e$ groups;

R$^e$ is independently for each occurrence oxo (=O), —OR$^a$, N(R$^a$)$_2$, halo, C$_{1-6}$alkyl, C$_{1-6}$haloalkyl, C$_{1-6}$heteroalkyl, C$_{3-6}$cycloalkyl, or two R$^e$ groups join together to provide a C$_{3-10}$heterocyclic group with a nitrogen to which the two R$^e$ groups are bound;

m is 1 to 4; and n is 0, 1 or 2.

In certain embodiments when R¹ is —NR$^d$R$^d$ wherein the two R$^d$ groups together with the nitrogen bound thereto provide a C$_{3-10}$heterocyclic group, the C$_{3-10}$heterocyclic group optionally includes one, two or three additional heteroatoms selected from nitrogen and oxygen. In some embodiments, the C$_{3-10}$heterocyclic group is substituted with one or more R$^e$ groups that join together to provide a C$_{3-10}$heterocyclic group and this C$_{3-10}$heterocyclic, along with the R$^b$ group can provide a spirocyclic group or a bridged or unbridged bicyclic group.

R¹ can be positioned on any suitable carbon atom(s) of phenyl ring A, such as at the 1, 2, 3, or 4 position, illustrated in Formula I. In some embodiments, one R¹ is R$^a$, wherein R$^a$ is C$_1$-C$_{10}$alkyl (e.g., methyl, ethyl, propyl, butyl, pentyl, hexyl, heptyl, octyl, nonyl, or decyl), and a second R¹ is R$^b$, wherein R$^b$ is halogen (e.g., Br, F, I, or Cl) or —NR$^d$R$^d$ wherein two R$^a$ groups together with the nitrogen bound thereto provide a C$_{4-9}$heterocyclic group. In some embodiments, the C$_{4-9}$heterocyclic group is substituted with one or more R$^e$ groups and/or has one or more additional heteroatoms in addition to the nitrogen to which both R$^a$ groups are bound. Some compound embodiments comprise at least one R¹ group that is an R$^b$ group, wherein R$^b$ is —NR$^d$R$^d$, wherein (i) each R$^d$ independently is R$^a$ or R$^e$; or (ii) two R$^d$ groups together with the nitrogen bound thereto provide a C$_{4-9}$heterocyclic group. In some embodiments, R$^b$ is —NR$^d$R$^d$, wherein one R$^d$ is R$^a$, wherein R$^a$ is H, and the other R$^d$ is R$^e$, wherein R$^e$ is C$_{1-6}$haloalkyl. In some embodiments, the heterocyclic group comprises 1 or 2 heteroatoms (including the nitrogen atom of R$^b$). Certain heterocyclic groups comprise the nitrogen atom of the R$^b$ group and either an oxygen atom or an additional nitrogen atom. The heterocyclic groups in some compound embodiments are bound to the ring A phenyl ring of Formula I via the nitrogen atom of the R$^b$ group. In some embodiments, the heterocyclic group is substituted with two R$^e$ groups, wherein R$^e$ is independently for each occurrence C$_{1-6}$haloalkyl (e.g., —CH$_2$Cl) or C$_{1-6}$heteroalkyl (e.g., CH$_2$OH). The heterocyclic groups are 6-membered or 7-membered heterocyclic groups. In exemplary embodiments, the heterocyclic group is

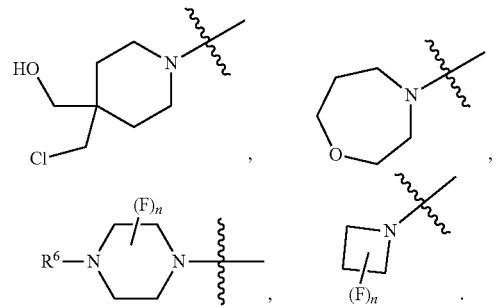

wherein each n independently is an integer ranging from 0 to 4, such as 0, 1, 2, 3, or 4; and R$^6$ is selected from hydrogen; aliphatic, such as C$_{1-10}$aliphatic; aromatic, such as C$_{5-10}$aromatic; or heteroaliphatic, such as C$_{1-10}$heteroaliphatic.

In some embodiments, R¹ is R$^b$ wherein R$^b$ is —NR$^d$R$^d$ and both R$^d$ groups together with the nitrogen bound thereto provide a C$_{4-9}$heterocyclic group substituted with at least two R$^e$ groups wherein the two R$^e$ groups join together to provide a C$_{3-10}$heterocyclic group with the R$^b$ group to which they are attached. In such embodiments, the two R$^e$ groups can join together such that a bicyclic group or a spirocyclic group is provided (wherein one ring of the bicyclic group or spirocyclic group is provided by the R$^b$ group and the other ring of the bicylic group or the spirocyclic group is provided by the two R$^e$ groups). In embodiments comprising a spirocyclic group, each ring of the spirocyclic group may have the same number of atoms or a different number of atoms. In particular embodiments, the spirocyclic group comprises at least two rings, wherein a first ring and a second ring of the spirocyclic group have a different number of carbon atoms, a different number of heteroatoms, or both. In some embodiments, the two rings of the spirocyclic group comprise the same number of carbon atoms, the same number of heteroatoms, or both. In some embodiments, each ring of the spirocyclic group comprises a heteroatom in the ring and the heteroatom may be the same in each ring, or each ring of the spirocyclic group may have a different heteroatom in the ring. The spirocyclic group can comprise a first ring coupled to a carbon atom of the ring A phenyl group, wherein the first ring has from 3 to 7 atoms, and a second ring has from 3 to 7 atoms. In some embodiments, the spirocyclic group comprises at least one oxygen atom in addition to the nitrogen atom of the R$^b$ group. The spirocyclic group may comprise greater than 7 total atoms in the spirocyclic system with particular embodiments comprising 9 total atoms in the spirocyclic system. In exemplary embodiments, R$^b$ together with two R$^e$ groups can provide the following spirocycles:

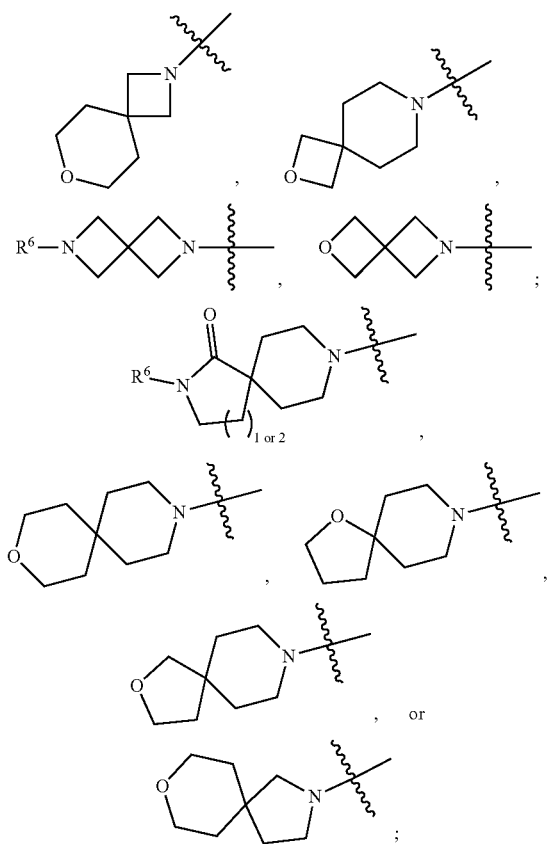
wherein R⁶ is selected from hydrogen; aliphatic, such as $C_{1-10}$aliphatic; aromatic, such as $C_{5-10}$aromatic; or heteroaliphatic, such as $C_{1-10}$heteroaliphatic.
By way of example of such moieties, in certain embodiments, R¹ is selected from
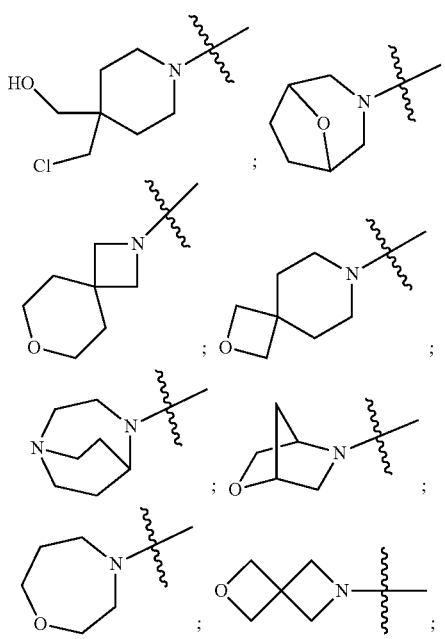
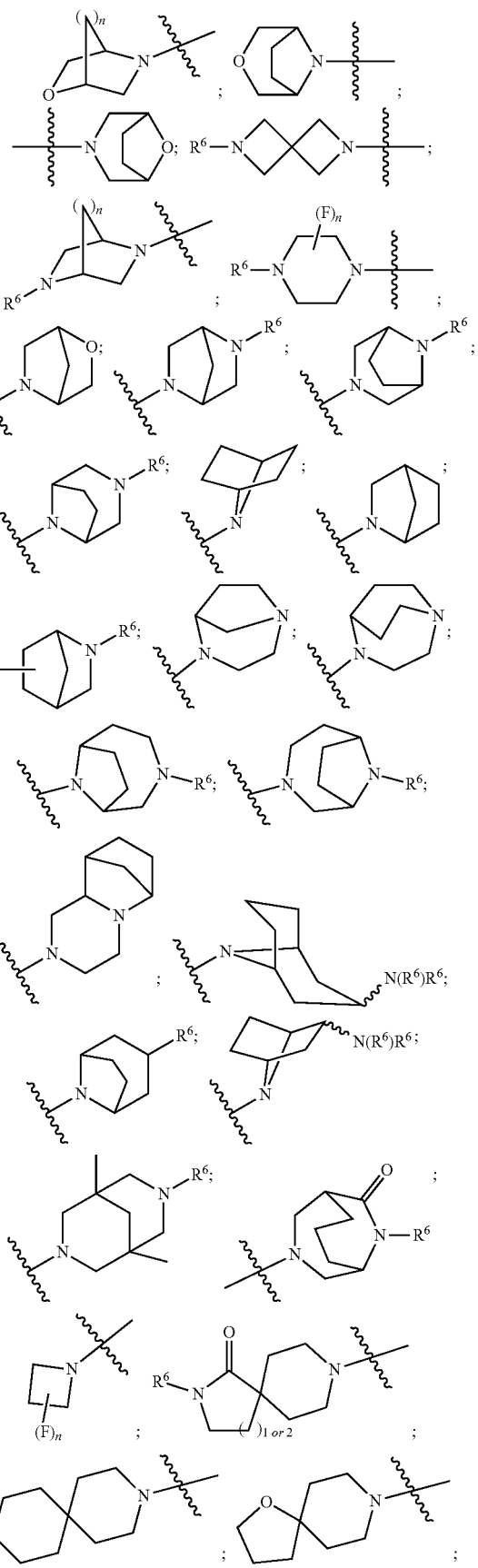

17

-continued

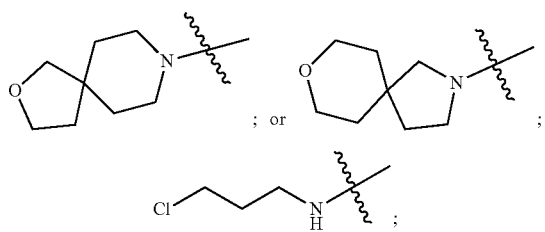

wherein each n independently is an integer ranging from 0 to 4, such as 0, 1, 2, 3, or 4; and $R^6$ independently is selected from hydrogen; aliphatic, such as $C_{1-10}$aliphatic; aromatic, such as $C_{5-10}$aromatic; or heteroaliphatic, such as $C_{1-10}$heteroaliphatic.

In certain embodiments, $R^1$ is a -linker-$R^6$ group, such as a $C_{2-10}$alkynyl moiety. Such $C_{2-10}$alkynyl moieties may be linear, branched, and/or cyclic, and have one, two or three substituents. Exemplary substituents include cycloalkyl and OH. In some embodiments, one substituent is oxetanyl, azetidinyl, pyridinyl, pyrrolidinyl, piperidinyl, tetrahydrofuranyl, tetrahydropyranyl, amino, or phosphate, and/or in some embodiments, one substituent is —OC(O)—$R^8$. The $C_{2-10}$alkyne may comprise a linear and/or branched section and a cyclic section, such as in

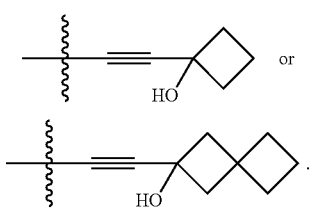

Some compounds comprise a linker that is a $C_1$ group and an $R^6$ group that is $R^b$, wherein $R^b$ is —$NR^dR^d$ wherein one $R^d$ is H and the other $R^6$ is pyridinyl, or wherein both $R^d$ groups together with the nitrogen bound thereto provide a $C_{5-10}$heteroaryl; or $R^b$ is $OR^c$, wherein $R^c$ is $C_{1-4}$alkyl substituted with a pyridinyl group. In some embodiments, $R^b$ is

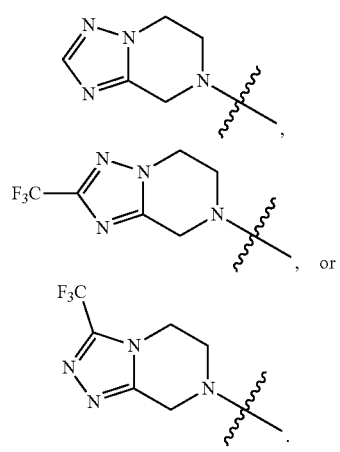

18

In some embodiments, $R^1$ can be selected from any of the following.

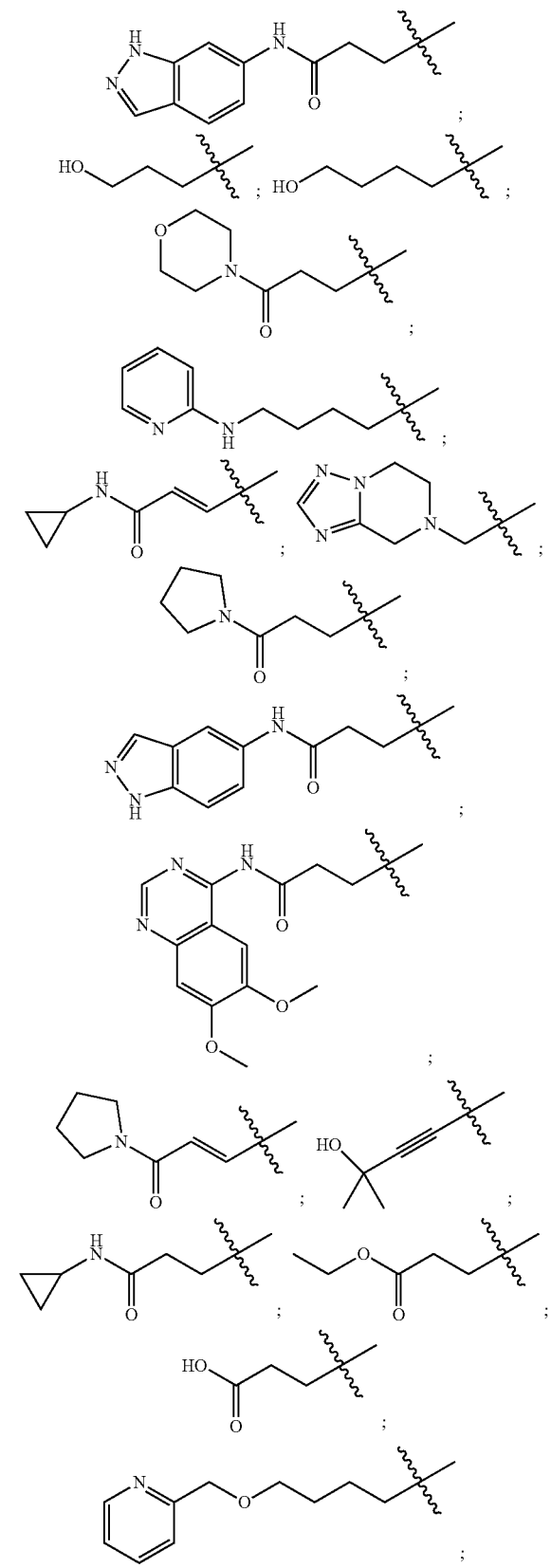

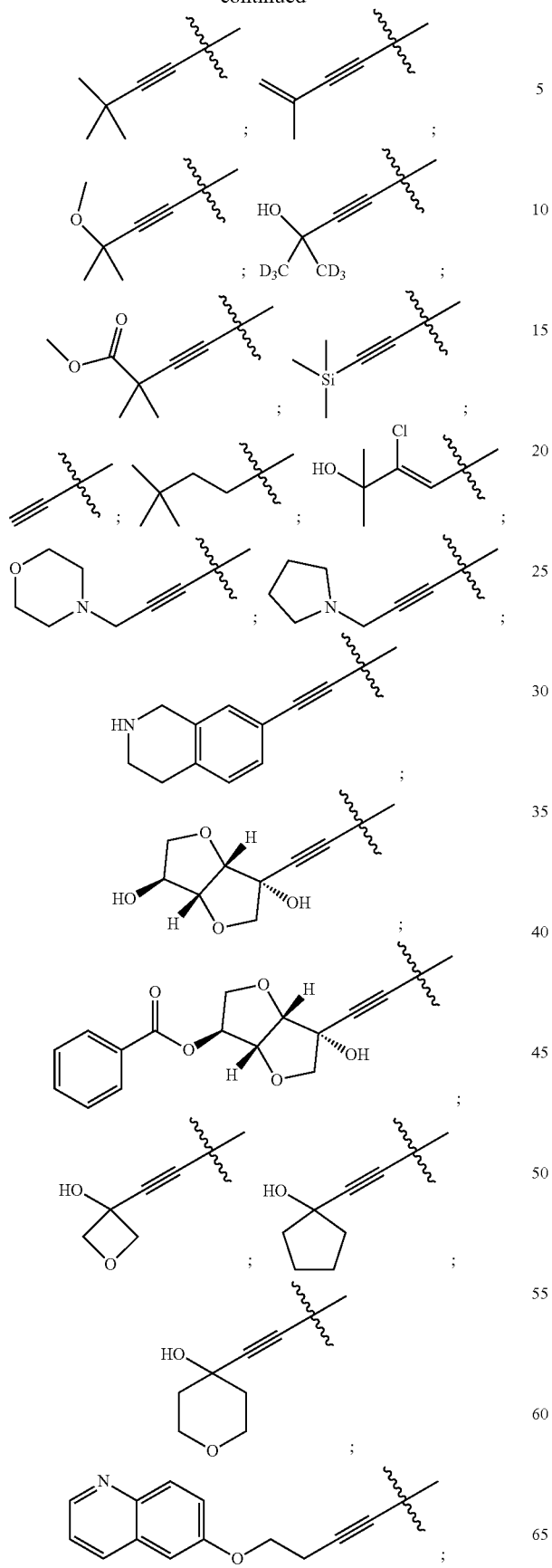
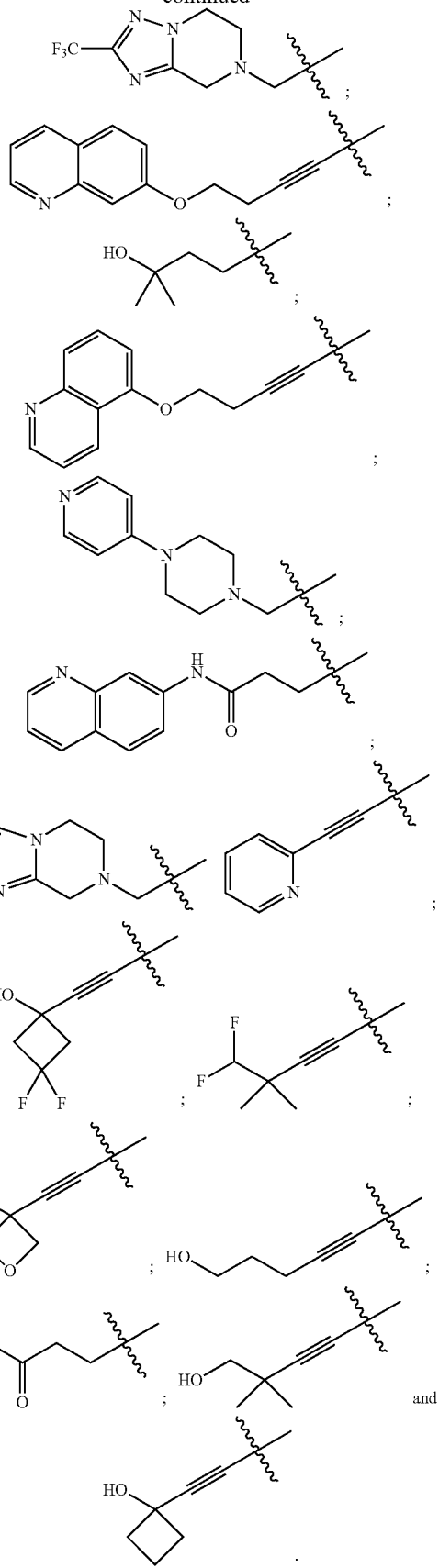

In particular embodiments, $R^1$ is selected from

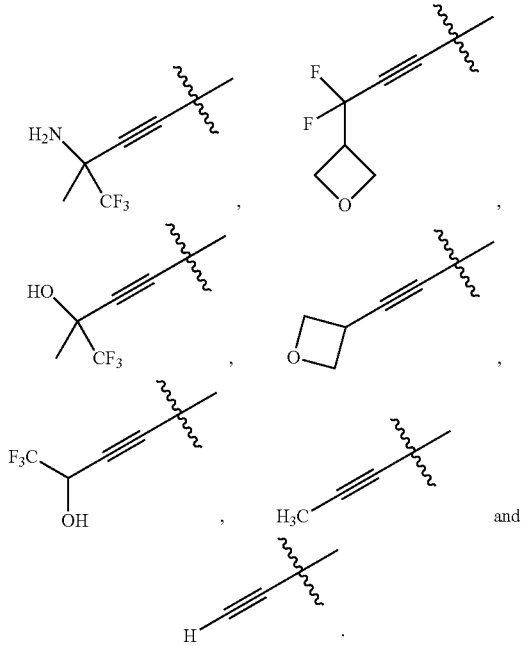

In some embodiments, each of $R^2$ and $R^3$ independently is $R^a$ wherein $R^a$ is independently in each occurrence hydrogen, methyl, ethyl, propyl, butyl, pentyl, or hexyl. In particular embodiments, each of $R^2$ and $R^3$ independently is $R^a$ which is independently for each occurrence hydrogen, methyl, or ethyl. In exemplary embodiments, $R^2$ is methyl and $R^3$ is hydrogen.

With reference to each of the embodiments described above, X is $CH_2$ or O.

In particular embodiments of Formula I, including those described above, the B ring heteroaryl group is five-membered. Such five-membered heteroaryl groups can have a structure satisfying formula

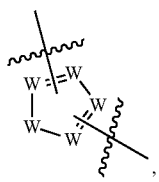

wherein at least one W is nitrogen, and each remaining W independently is selected from C, —C($R^a$)—, CH, oxygen, sulfur, nitrogen, or NH. In some embodiments, the 5-membered heteroaryl group is a triazole, a diazole, such as an imidazole or a pyrazole, an oxazole or an oxadiazole.

Exemplary diazoles and triazoles include any of the following.

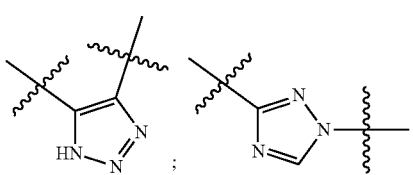

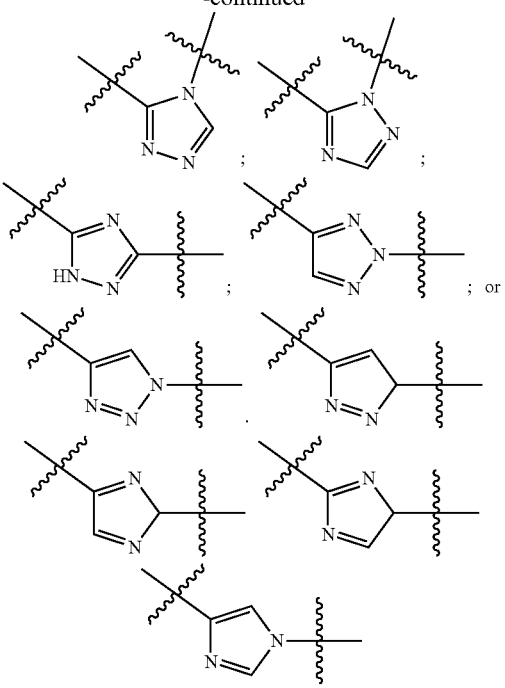

Exemplary oxazoles include any of the following:

In other embodiments, B is six membered heteroaryl, such as a pyridine, pyridazine, pyrimidine or pyrazine.

In certain embodiments, L is a divalent $C_{1-10}$aliphatic group; such as a $C_1$-$C_4$alkylene linker (e.g., —$CH_2$—, —$CH_2CH_2$—, —$CH_2CH_2CH_2$—, or —$CH_2CH_2CH_2CH_2$—). In some embodiments, L is —$CH_2$—.

With continued reference to Formula I, Z may be aryl, such as phenyl, or heteroaryl. In embodiments where Z is heteroaryl, Z may be a 5-membered or 6-membered heteroaryl, such as a 5-membered or 6-membered nitrogen-containing heteroaryl, for example, pyridinyl, pyridazinyl, pyrimidinyl, pyrazinyl, pyrazolyl, imidazolyl, pyrrolyl, or triazolyl. In certain such embodiments, Z is a 6-membered nitrogen-containing heteroaryl, and may be pyridinyl, pyrimidinyl or pyridazinyl. In certain embodiments Z is aryl, such as

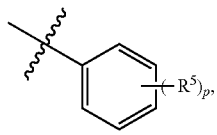

wherein $R^5$ is for each occurrence independently $R^e$ and p is 0, 1, 2, 3, 4, or 5. In other embodiments Z is heteroaryl, such as

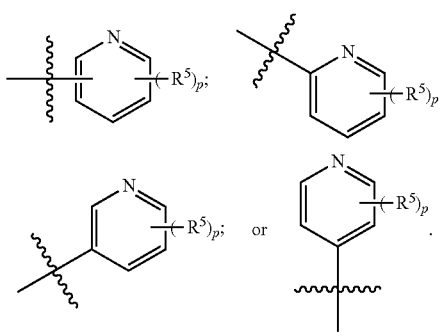

Certain disclosed compounds comprise an $R^5$ group that is an $R^a$ group, wherein $R^a$ is $C_1$-$C_4$aliphatic, or that is an $R^b$ group, wherein $R^b$ is halogen, such as fluoro, $R^2$ is $R^a$ wherein $R^a$ is $C_1$-$C_4$aliphatic, and $R^3$ is $R^a$, wherein $R^a$ is hydrogen.

The compounds of Formulas I can also have structures satisfying any one or more of Formulas II and IIA-IIF, IIG and IIH.

Formula II

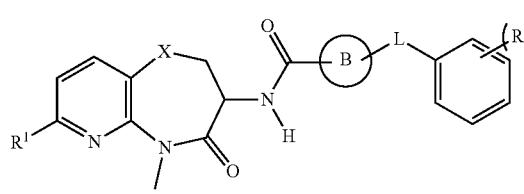

Formula IIA

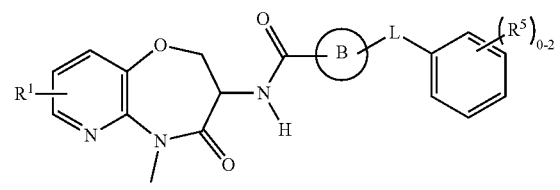

Formula IIB

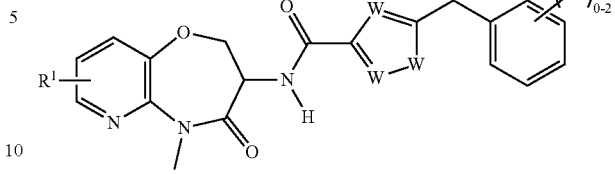

Formula IIC

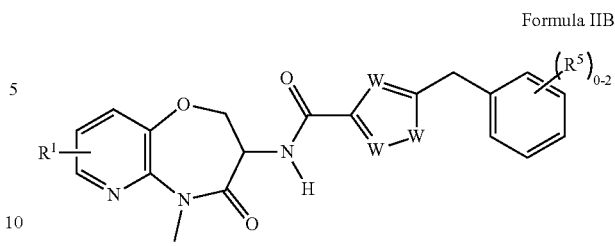

Formula IID

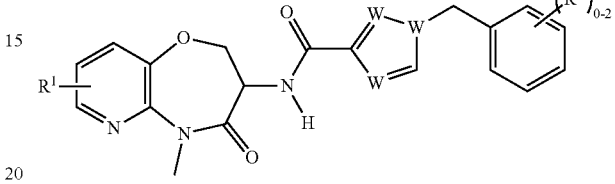

Formula IIE

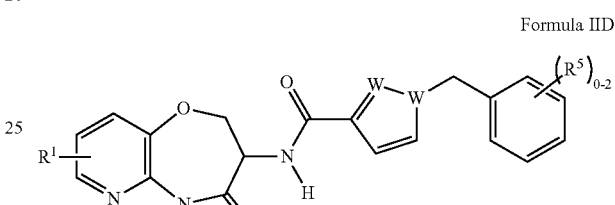

Formula IIF

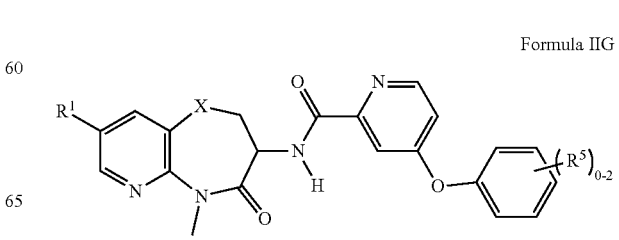

Formula IIG

Formula IIH

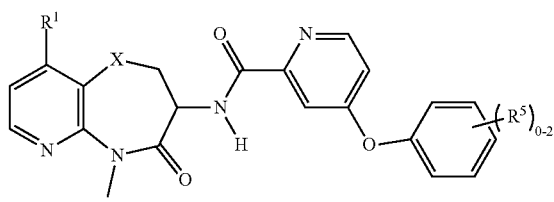

Formula IIK

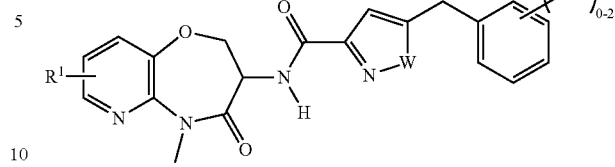

With reference to Formulas II and IIA-IIH, each of $R^1$, X, W and $R^5$ are as recited above for Formula I. In particular embodiments, 0, 1, or 2 $R^5$ groups are present. $R^5$ can be $R^e$ wherein $R^e$ is fluoro or chloro. In other particular embodiments, $R^5$ is not present. With reference to Formulas IIA-IIF, each W independently is nitrogen or oxygen, and particularly nitrogen. In particular embodiments Formula IIE has the formula IIK.

wherein W is O or N. As understood by those of ordinary skill in the art, when W is N in Formula IIK, the N has an open valence and may be substituted with hydrogen or, with reference to Formula I, an $R^e$ group. By way of example, suitable $R^e$ groups for substitution of the nitrogen in such instances includes $C_{1-6}$alkyl, $C_{1-6}$haloalkyl, $C_{1-6}$heteroalkyl, $C_{3-6}$cycloalkyl.

Certain exemplary compounds within the scope of one or more of Formulas I, II, and IIA-IIG, IIH and IIK include:

| Compound | Structure |
|---|---|
| I-1 | 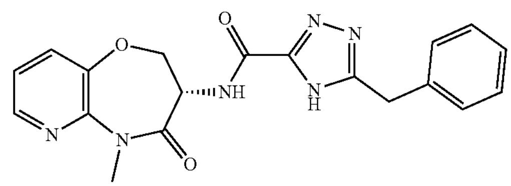 |
| I-2 | 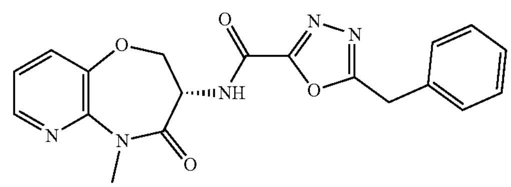 [SMILES: CN1C(=O)[C@@H](NC(=O)c2nnc(Cc3ccccc3)o2)COc2cccnc21] |
| I-3 | 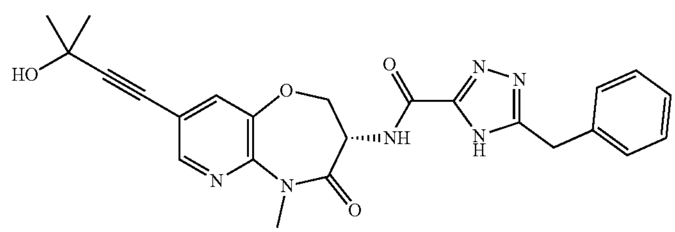 [SMILES: CN1C(=O)[C@@H](NC(=O)c2nnc(Cc3ccccc3)[nH]2)COc2cc(C#CC(C)(C)O)cnc21] |
| I-4 | 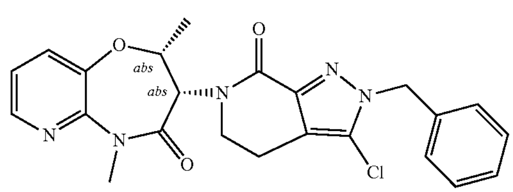 [SMILES: C[C@H]1Oc2cccnc2N(C)C(=O)[C@H]1N1CCc2c(nn(Cc3ccccc3)c2Cl)C1=O] |
| I-5 | 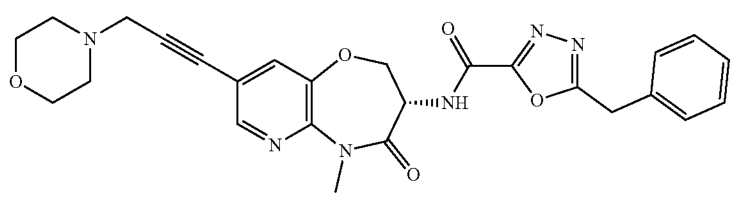 [SMILES: CN1C(=O)[C@@H](NC(=O)c2nnc(Cc3ccccc3)o2)COc2cc(C#CCN3CCOCC3)cnc21] |

-continued

| Compound | Structure |
|---|---|
| I-6 | 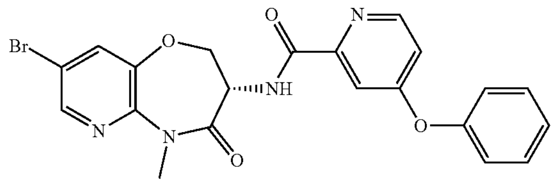 [SMILES: CN1C(=O)[C@@H](NC(=O)c2cc(Oc3ccccc3)ccn2)COc2cc(Br)cnc21] |
| I-7 | 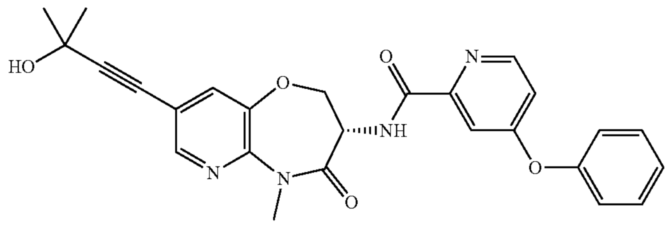 [SMILES: CN1C(=O)[C@@H](NC(=O)c2cc(Oc3ccccc3)ccn2)COc2cc(C#CC(C)(C)O)cnc21] |
| I-8 | 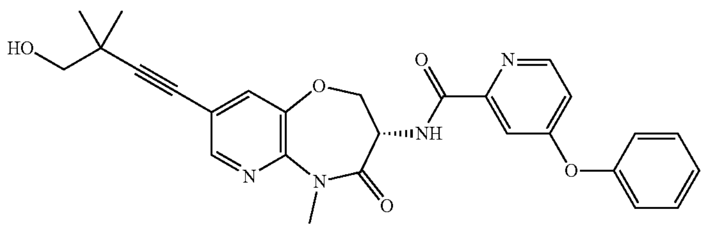 [SMILES: CN1C(=O)[C@@H](NC(=O)c2cc(Oc3ccccc3)ccn2)COc2cc(C#CC(C)(C)CO)cnc21] |
| I-9 | 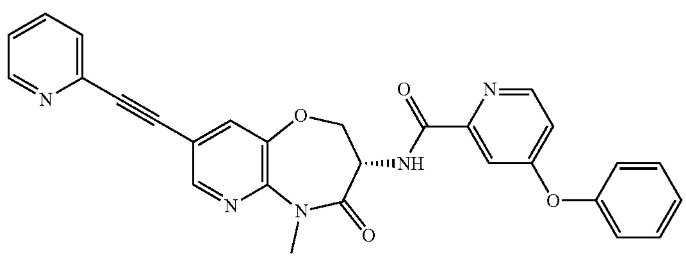 [SMILES: CN1C(=O)[C@@H](NC(=O)c2cc(Oc3ccccc3)ccn2)COc2cc(C#Cc3ccccn3)cnc21] |
| I-10 | 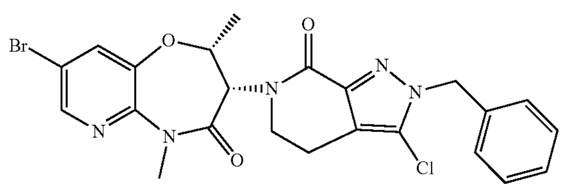 [SMILES: C[C@H]1Oc2cc(Br)cnc2N(C)C(=O)[C@H]1N1CCc2c(nn(Cc3ccccc3)c2Cl)C1=O] |
| I-11 | 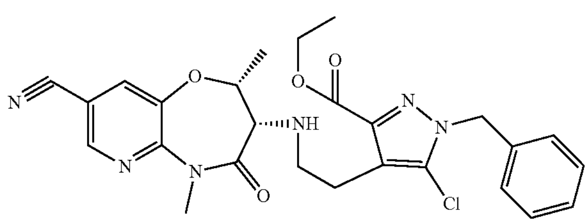 [SMILES: CCOC(=O)c1nn(Cc2ccccc2)c(Cl)c1CCN[C@@H]1C(=O)N(C)c2ncc(C#N)cc2O[C@@H]1C] |
| I-12 | 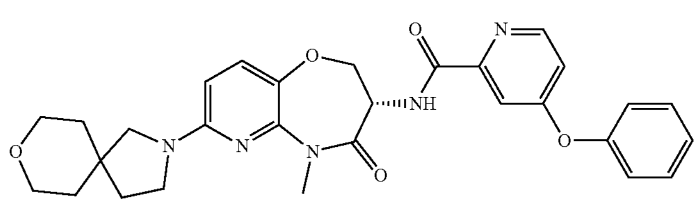 [SMILES: CN1C(=O)[C@@H](NC(=O)c2cc(Oc3ccccc3)ccn2)COc2ccc(N3CCC4(CCOCC4)C3)nc21] |

| Compound | Structure |
|---|---|
| I-13 | 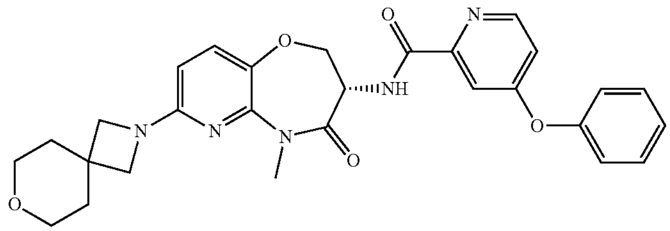 [SMILES: CN1C(=O)[C@@H](NC(=O)c2cc(Oc3ccccc3)ccn2)COc2ccc(N3CC4(CCOCC4)C3)nc21] |
| I-14 | 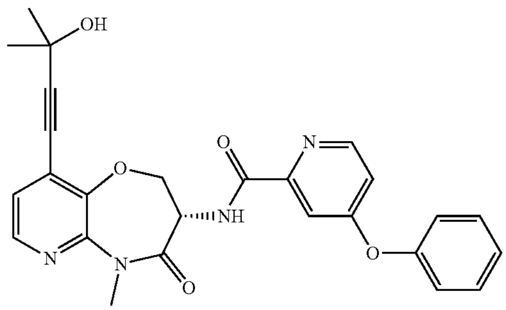 [SMILES: CN1C(=O)[C@@H](NC(=O)c2cc(Oc3ccccc3)ccn2)COc2c(C#CC(C)(C)O)ccnc21] |
| I-15 | 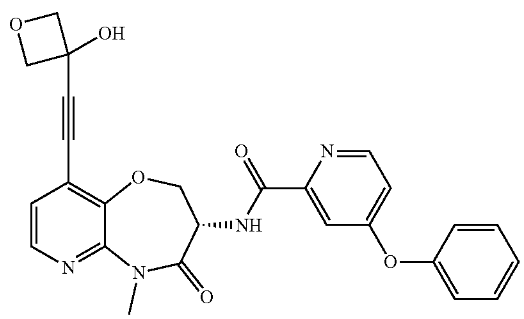 [SMILES: CN1C(=O)[C@@H](NC(=O)c2cc(Oc3ccccc3)ccn2)COc2c(C#CC3(O)COC3)ccnc21] |
| I-16 | 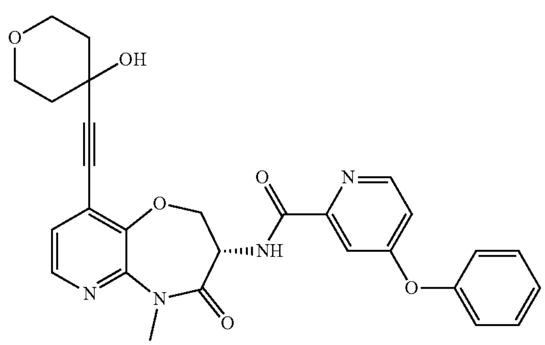 [SMILES: CN1C(=O)[C@@H](NC(=O)c2cc(Oc3ccccc3)ccn2)COc2c(C#CC3(O)CCOCC3)ccnc21] |
| I-17 | 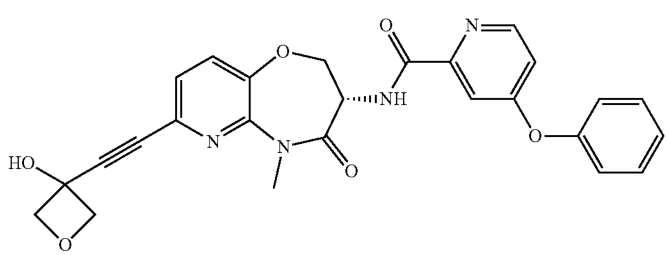 [SMILES: CN1C(=O)[C@@H](NC(=O)c2cc(Oc3ccccc3)ccn2)COc2ccc(C#CC3(O)COC3)nc21] |

-continued

| Compound | Structure |
|---|---|
| I-18 | 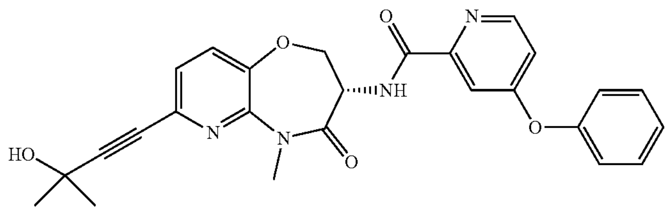 [SMILES: CN1C(=O)[C@@H](NC(=O)c2cc(Oc3ccccc3)ccn2)COc2ccc(C#CC(C)(C)O)nc21] |
| I-19 | 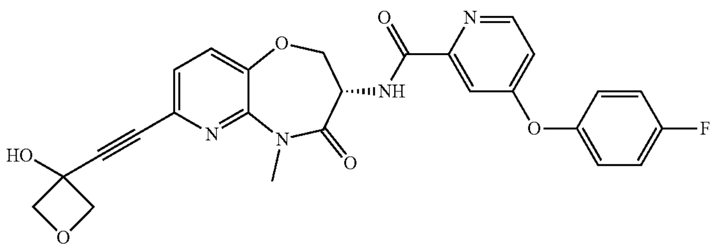 [SMILES: CN1C(=O)[C@@H](NC(=O)c2cc(Oc3ccc(F)cc3)ccn2)COc2ccc(C#CC3(O)COC3)nc21] |
| I-20 | 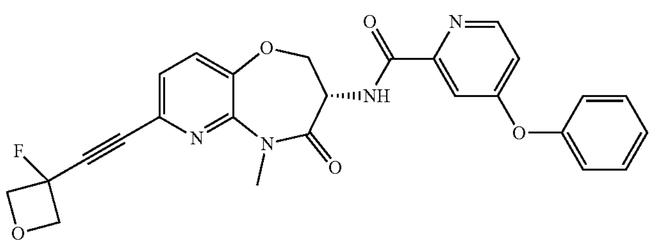 [SMILES: CN1C(=O)[C@@H](NC(=O)c2cc(Oc3ccccc3)ccn2)COc2ccc(C#CC3(F)COC3)nc21] |
| I-21 | 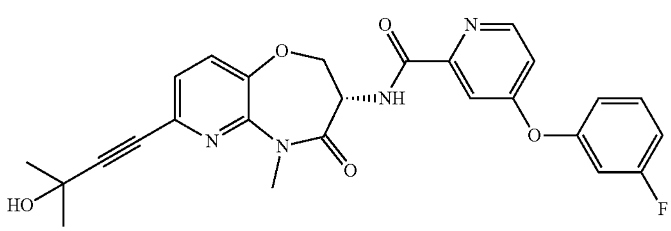 [SMILES: CN1C(=O)[C@@H](NC(=O)c2cc(Oc3cccc(F)c3)ccn2)COc2ccc(C#CC(C)(C)O)nc21] |
| I-22 | 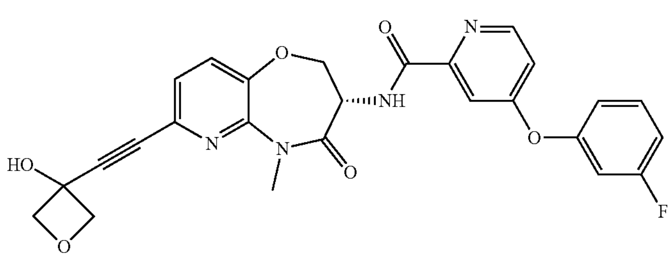 [SMILES: CN1C(=O)[C@@H](NC(=O)c2cc(Oc3cccc(F)c3)ccn2)COc2ccc(C#CC3(O)COC3)nc21] |
| I-23 | 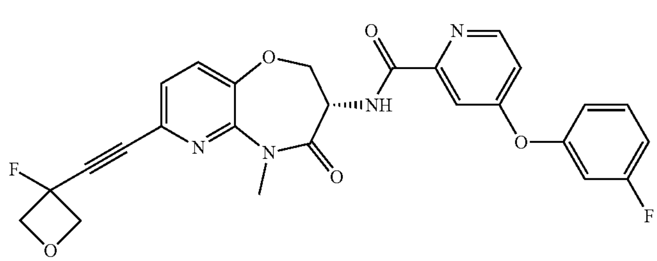 [SMILES: CN1C(=O)[C@@H](NC(=O)c2cc(Oc3cccc(F)c3)ccn2)COc2ccc(C#CC3(F)COC3)nc21] |

-continued
| Compound | Structure |
|---|---|
| I-24 | 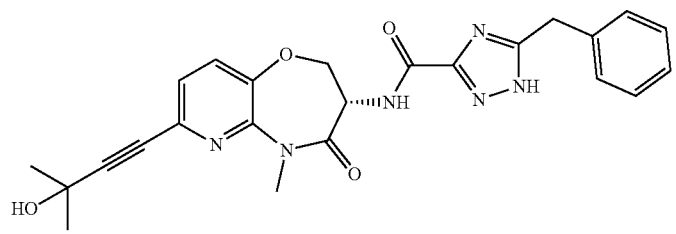 [SMILES: CN1C(=O)[C@@H](NC(=O)c2n[nH]c(Cc3ccccc3)n2)COc2ccc(C#CC(C)(C)O)nc21] |
| I-25 | 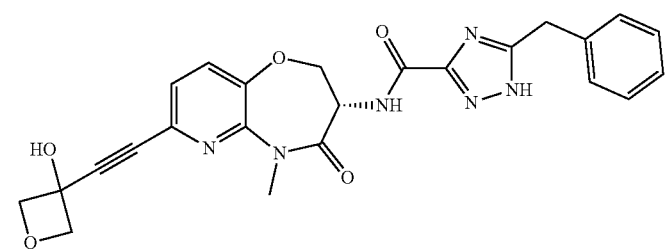 [SMILES: CN1C(=O)[C@@H](NC(=O)c2n[nH]c(Cc3ccccc3)n2)COc2ccc(C#CC3(O)COC3)nc21] |
| I-26 | 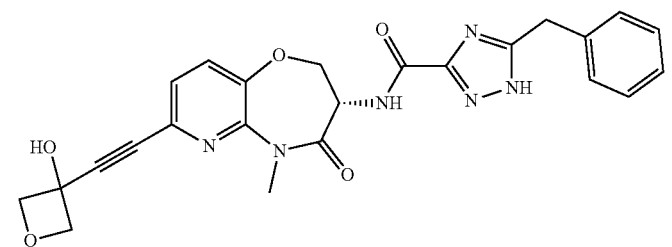 [SMILES: CN1C(=O)[C@@H](NC(=O)c2n[nH]c(Cc3ccccc3)n2)COc2ccc(C#CC3(O)COC3)nc21] |
| I-27 | 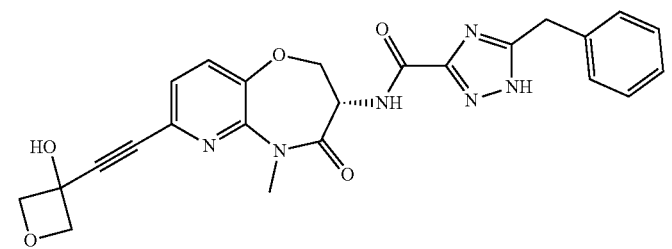 [SMILES: CN1C(=O)[C@@H](NC(=O)c2n[nH]c(Cc3ccccc3)n2)COc2ccc(C#CC3(O)COC3)nc21] |
| I-28 | 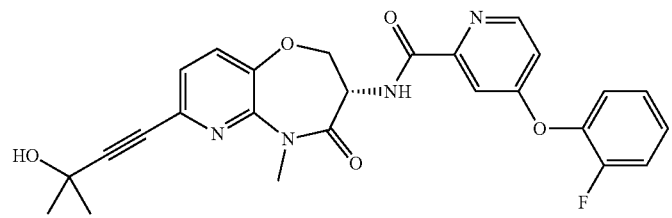 [SMILES: CN1C(=O)[C@@H](NC(=O)c2cc(Oc3ccccc3F)ccn2)COc2ccc(C#CC(C)(C)O)nc21] |
| I-29 | 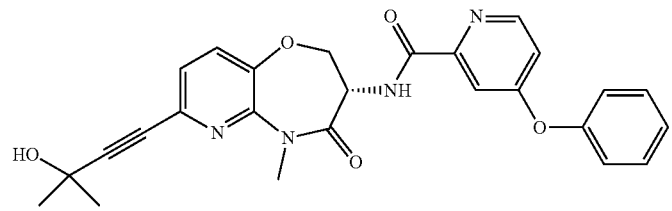 |

-continued
| Compound | Structure |
|---|---|
| I-30 | 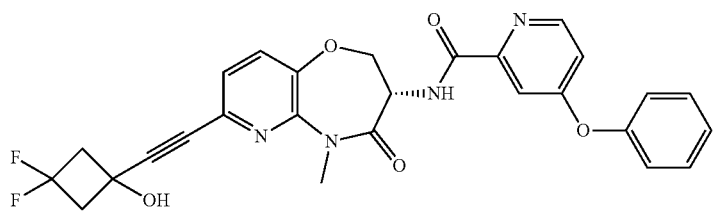 [SMILES: CN1C(=O)[C@@H](NC(=O)c2cc(Oc3ccccc3)ccn2)COc2ccc(C#CC3(O)CC(F)(F)C3)nc21] |
| I-31 | 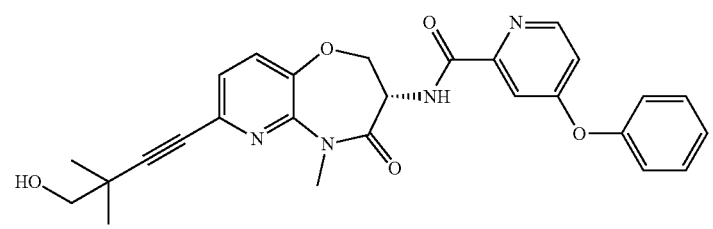 [SMILES: CN1C(=O)[C@@H](NC(=O)c2cc(Oc3ccccc3)ccn2)COc2ccc(C#CC(C)(C)CO)nc21] |
| I-32 | 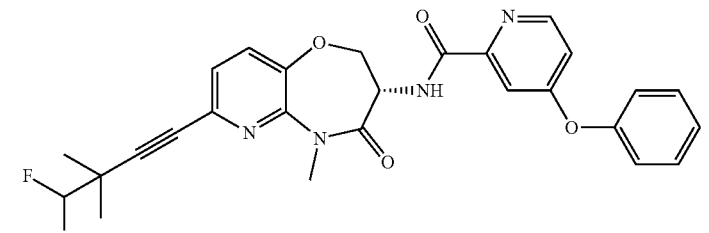 |
| I-33 | 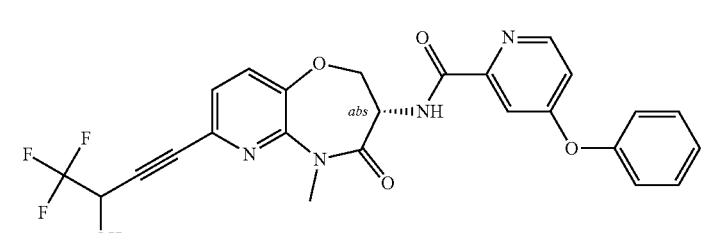 |
| I-34 | 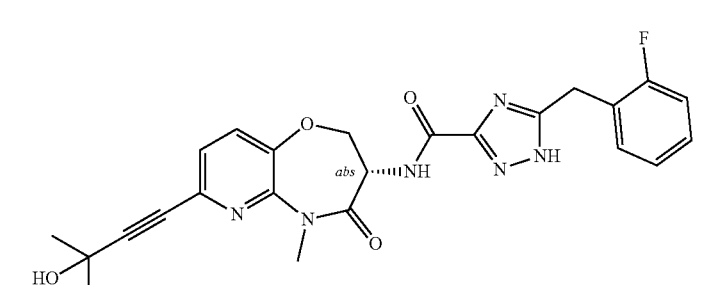 |
| I-35 | 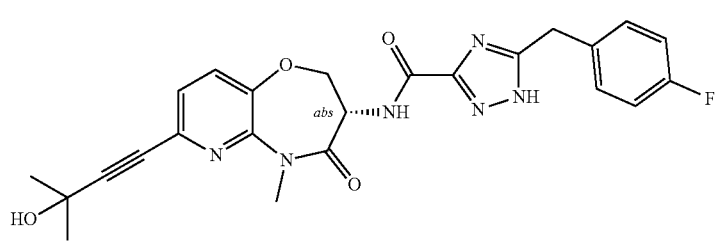 [SMILES: CN1C(=O)[C@@H](NC(=O)c2n[nH]c(Cc3ccc(F)cc3)n2)COc2ccc(C#CC(C)(C)O)nc21] |

-continued

| Compound | Structure |
|---|---|
| I-36 | 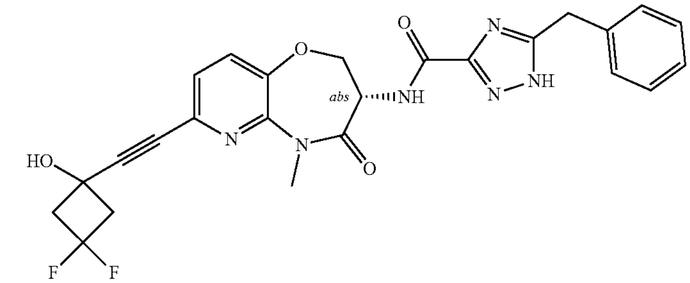 [SMILES: CN1C(=O)[C@@H](NC(=O)c2n[nH]c(Cc3ccccc3)n2)COc2ccc(C#CC3(O)CC(F)(F)C3)nc21] |
| I-37 | 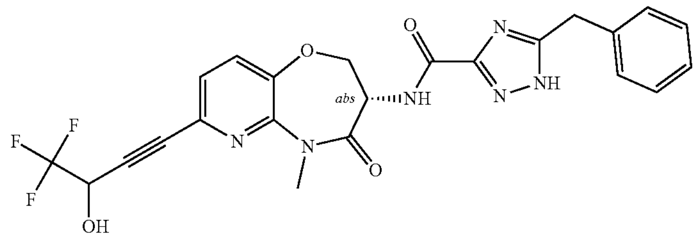 [SMILES: CN1C(=O)[C@@H](NC(=O)c2n[nH]c(Cc3ccccc3)n2)COc2ccc(C#CC(O)C(F)(F)F)nc21] |
| I-38 | 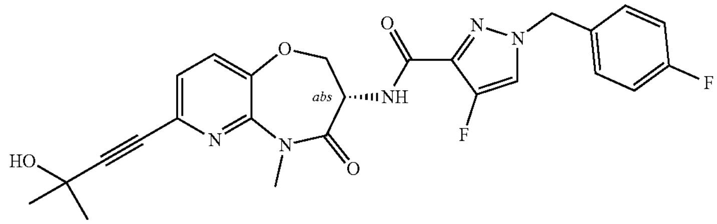 [SMILES: CN1C(=O)[C@@H](NC(=O)c2nn(Cc3ccc(F)cc3)cc2F)COc2ccc(C#CC(C)(C)O)nc21] |
| I-39 | 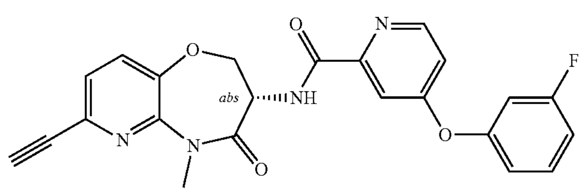 [SMILES: C#Cc1ccc2c(n1)N(C)C(=O)[C@@H](NC(=O)c1cc(Oc3cccc(F)c3)ccn1)CO2] |
| I-40 | 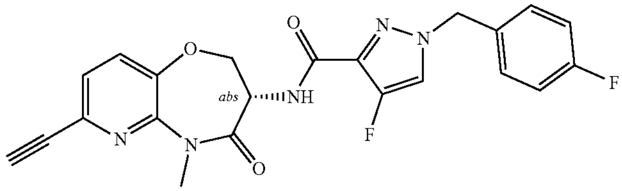 [SMILES: C#Cc1ccc2c(n1)N(C)C(=O)[C@@H](NC(=O)c1nn(Cc3ccc(F)cc3)cc1F)CO2] |
| I-41 | 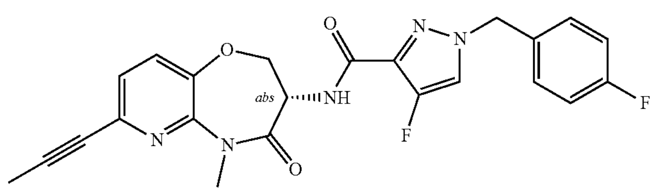 [SMILES: CC#Cc1ccc2c(n1)N(C)C(=O)[C@@H](NC(=O)c1nn(Cc3ccc(F)cc3)cc1F)CO2] |
| I-42 | 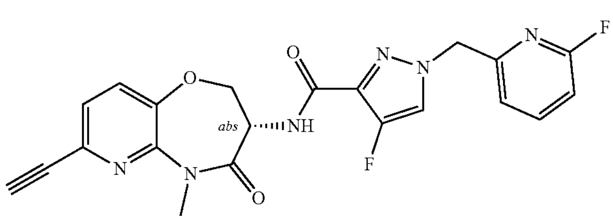 [SMILES: C#Cc1ccc2c(n1)N(C)C(=O)[C@@H](NC(=O)c1nn(Cc3cccc(F)n3)cc1F)CO2] |

-continued

| Compound | Structure |
|---|---|
| I-43 | 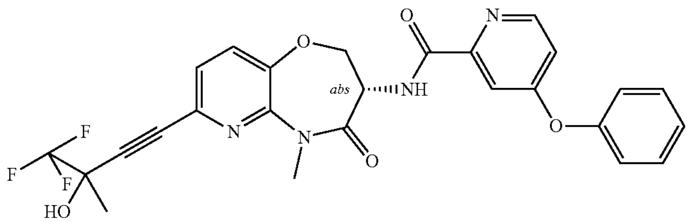 [SMILES: CN1C(=O)[C@@H](NC(=O)c2cc(Oc3ccccc3)ccn2)COc2ccc(C#CC(C)(O)C(F)(F)F)nc21] |
| I-44 | 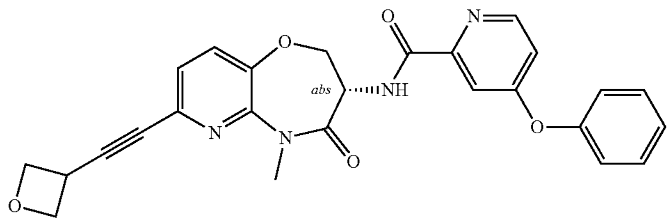 |
| I-45 | 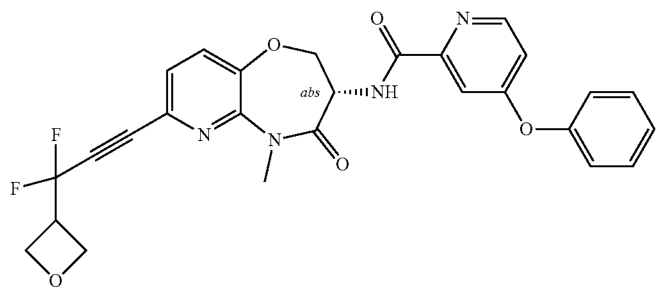 [SMILES: CN1C(=O)[C@@H](NC(=O)c2cc(Oc3ccccc3)ccn2)COc2ccc(C#CC(F)(F)C3COC3)nc21] |
| I-46 | 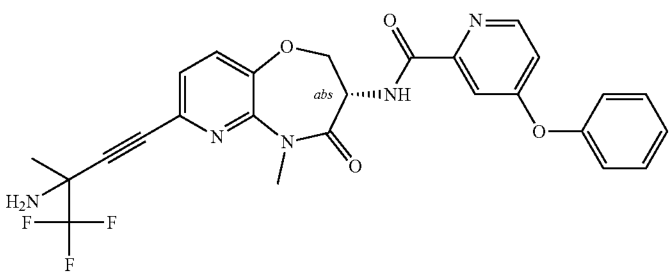 |
| I-47 | 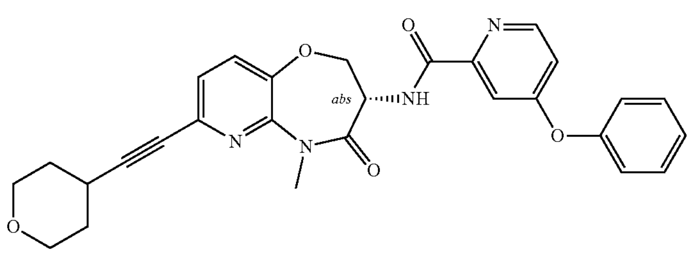 [SMILES: CN1C(=O)[C@@H](NC(=O)c2cc(Oc3ccccc3)ccn2)COc2ccc(C#CC3CCOCC3)nc21] |
| I-48 | 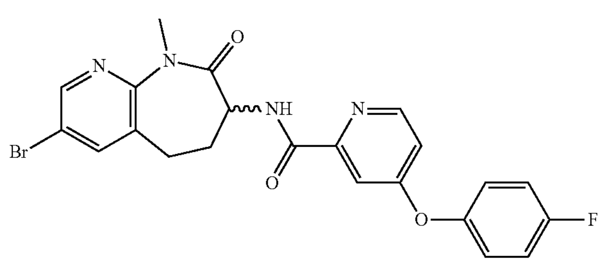 [SMILES: CN1C(=O)C(NC(=O)c2cc(Oc3ccc(F)cc3)ccn2)CCc2cc(Br)cnc21] |

-continued

| Compound | Structure |
|---|---|
| I-49 | 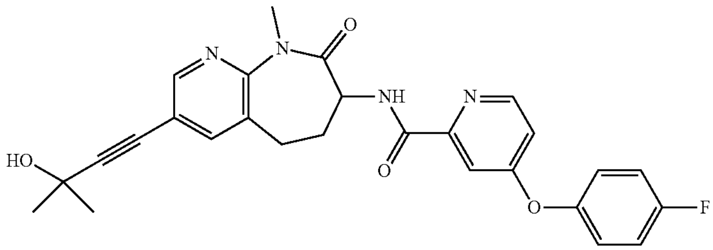 [SMILES: CN1C(=O)C(NC(=O)c2cc(Oc3ccc(F)cc3)ccn2)CCc2cc(C#CC(C)(C)O)cnc21] |
| I-50 | 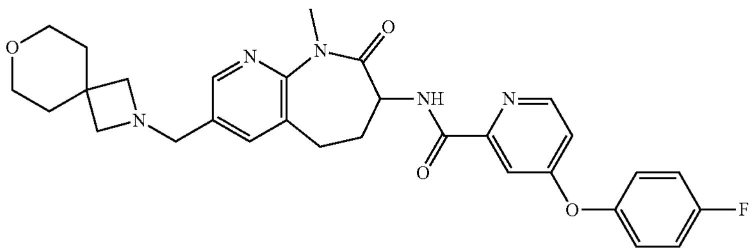 [SMILES: CN1C(=O)C(NC(=O)c2cc(Oc3ccc(F)cc3)ccn2)CCc2cc(CN3CC4(CCOCC4)C3)cnc21] |
| I-51 | 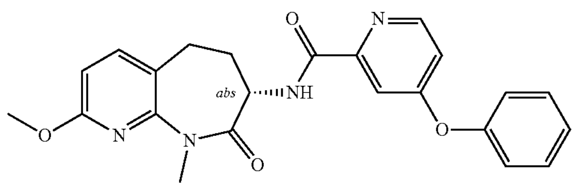 [SMILES: COc1ccc2c(n1)N(C)C(=O)[C@@H](NC(=O)c1cc(Oc3ccccc3)ccn1)CC2] |
| I-52 | 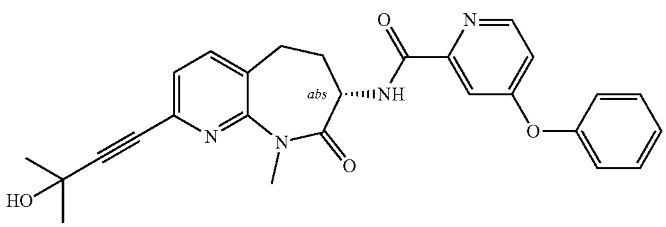 [SMILES: CN1C(=O)[C@@H](NC(=O)c2cc(Oc3ccccc3)ccn2)CCc2ccc(C#CC(C)(C)O)nc21] |
| I-53 | 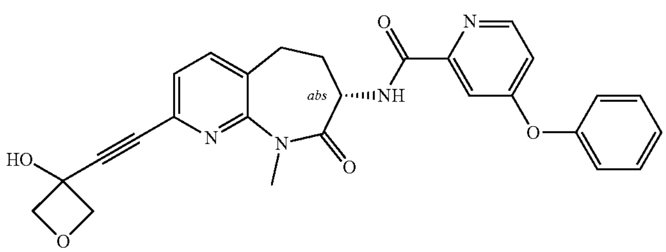 |
| I-54 | 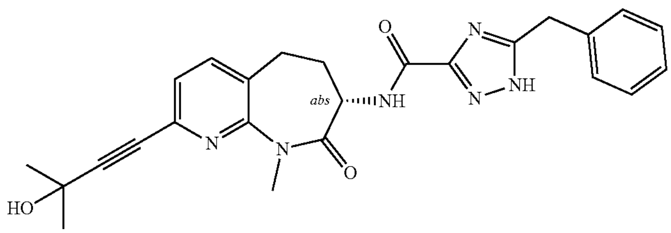 [SMILES: CN1C(=O)[C@@H](NC(=O)c2n[nH]c(Cc3ccccc3)n2)CCc2ccc(C#CC(C)(C)O)nc21] |

| Compound | Structure |
| --- | --- |
| I-55 | 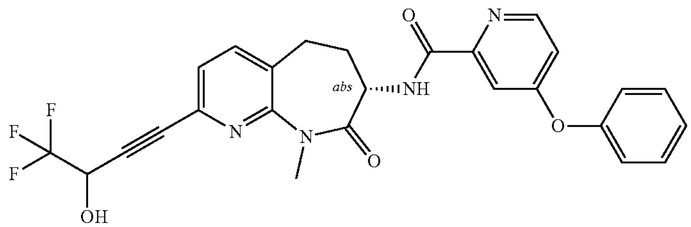 [SMILES: CN1C(=O)[C@@H](NC(=O)c2cc(Oc3ccccc3)ccn2)CCc2ccc(C#CC(O)C(F)(F)F)nc21] |
| I-56 | 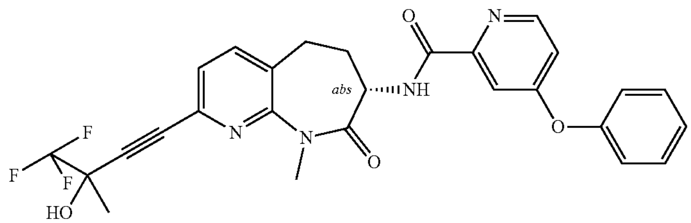 [SMILES: CN1C(=O)[C@@H](NC(=O)c2cc(Oc3ccccc3)ccn2)CCc2ccc(C#CC(C)(O)C(F)(F)F)nc21] |
| I-57 | 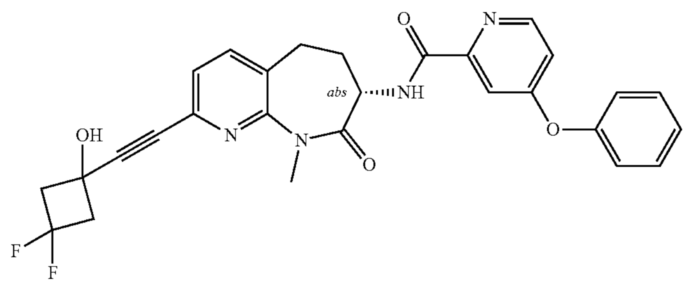 [SMILES: CN1C(=O)[C@@H](NC(=O)c2cc(Oc3ccccc3)ccn2)CCc2ccc(C#CC3(O)CC(F)(F)C3)nc21] |
| I-58 | 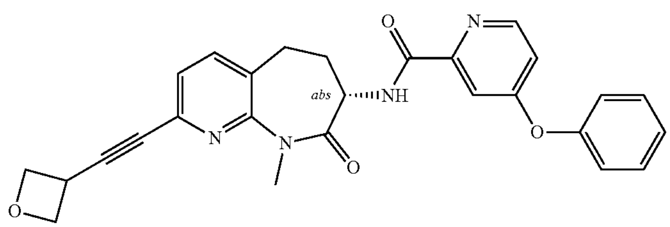 [SMILES: CN1C(=O)[C@@H](NC(=O)c2cc(Oc3ccccc3)ccn2)CCc2ccc(C#CC3COC3)nc21] |
| I-59 | 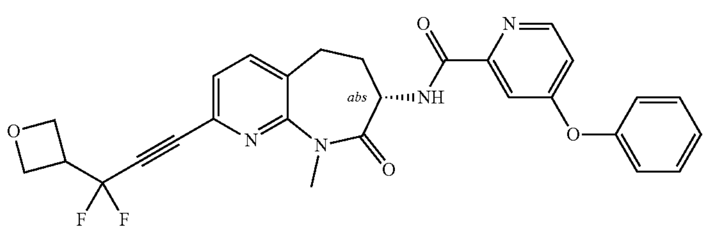 [SMILES: CN1C(=O)[C@@H](NC(=O)c2cc(Oc3ccccc3)ccn2)CCc2ccc(C#CC(F)(F)C3COC3)nc21] |
| I-60 | 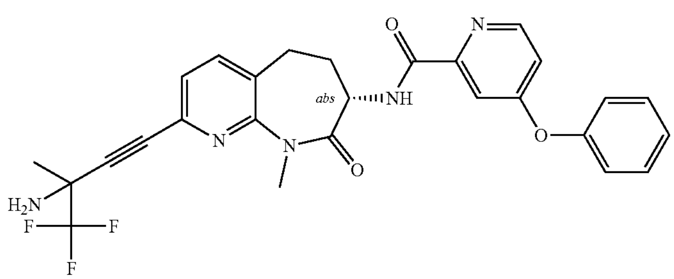 [SMILES: CN1C(=O)[C@@H](NC(=O)c2cc(Oc3ccccc3)ccn2)CCc2ccc(C#CC(C)(N)C(F)(F)F)nc21] |

In some embodiments, one or more of the compounds can be included in a pharmaceutical composition or medicament, and in some embodiments the compound or compounds can be in the form of the parent compound or a pharmaceutically acceptable salt, a stereoisomer, an N-oxide, a tautomer, a hydrate, a solvate, an isotope, or a prodrug thereof. The pharmaceutical composition typically includes at least one additional component other than a disclosed compound or compounds, such as a pharmaceutically acceptable excipient, an adjuvant, an additional therapeutic agent (described in the following section), or any combination thereof.

Pharmaceutically acceptable excipients can be included in pharmaceutical compositions for a variety of purposes, such as to dilute a pharmaceutical composition for delivery to a subject, to facilitate processing of the formulation, to provide advantageous material properties to the formulation, to facilitate dispersion from a delivery device, to stabilize the formulation (e.g., antioxidants or buffers), to provide a pleasant or palatable taste or consistency to the formulation, or the like. The pharmaceutically acceptable excipient(s) may include a pharmaceutically acceptable carrier(s). Exemplary excipients include, but are not limited to: mono-, di-, and polysaccharides, sugar alcohols and other polyols, such as, lactose, glucose, raffinose, melezitose, lactitol, maltitol, trehalose, sucrose, mannitol, starch, or combinations thereof, surfactants, such as sorbitols, diphosphatidyl choline, and lecithin; bulking agents; buffers, such as phosphate and citrate buffers; anti-adherents, such as magnesium stearate; binders, such as saccharides (including disaccharides, such as sucrose and lactose), polysaccharides (such as starches, cellulose, microcrystalline cellulose, cellulose ethers (such as hydroxypropyl cellulose), gelatin, synthetic polymers (such as polyvinylpyrrolidone, polyalkylene glycols); coatings (such as cellulose ethers, including hydroxypropylmethyl cellulose, shellac, corn protein zein, and gelatin); release aids (such as enteric coatings); disintegrants (such as crospovidone, crosslinked sodium carboxymethyl cellulose, and sodium starch glycolate); fillers (such as dibasic calcium phosphate, vegetable fats and oils, lactose, sucrose, glucose, mannitol, sorbitol, calcium carbonate, and magnesium stearate); flavors and sweeteners (such as mint, cherry, anise, peach, apricot or licorice, raspberry, and vanilla; lubricants (such as minerals, exemplified by talc or silica, fats, exemplified by vegetable stearin, magnesium stearate or stearic acid); preservatives (such as antioxidants exemplified by vitamin A, vitamin E, vitamin C, retinyl palmitate, and selenium, amino acids, exemplified by cysteine and methionine, citric acid and sodium citrate, parabens, exemplified by methyl paraben and propyl paraben); colorants; compression aids; emulsifying agents; encapsulation agents; gums; granulation agents; and combinations thereof.

III. Methods of Using Compounds

A. Diseases/Disorders

The disclosed compounds, as well as combinations and/or pharmaceutical compositions thereof, may be used to inhibit a RIP1 kinase by contacting the kinase either in vivo or ex vivo, with a compound or compounds of the present disclosure, or a composition comprising a compound or compounds of the present disclosure. Disclosed compound or compounds, or compositions comprising a disclosed compound or compounds also can be used to ameliorate, treat or prevent a variety of diseases and/or disorders. In particular embodiments, the disclosed compound, combinations of disclosed compounds, or pharmaceutical compositions thereof, may be useful for treating conditions in which inhibition of RIP1 or a pathway involving RIP1 is therapeutically useful. In some embodiments, the compounds directly inhibit RIP1 kinase activity. In certain embodiments, disclosed compounds are useful for treating autoimmune diseases, inflammatory disorders, cardiovascular diseases, nerve disorders, neurodegenerative disorders, allergic disorders, respiratory diseases, kidney diseases, cancers, ischemic conditions, erythrocyte deficiencies, lung and brain injuries (e.g., induced by ischemia-reperfusion or cisplatin and/or cerebrovascular accident), and bacterial and viral infections.

In some embodiments, the disclosed compound, combinations of disclosed compounds, or pharmaceutical compositions thereof, may be used to treat or prevent allergic diseases, amyotrophic lateral sclerosis (ALS), spinal muscular atrophy, systemic lupus erythematosus, rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmyopathy, or asthma.

The disclosed compound, combinations of disclosed compounds, or pharmaceutical compositions thereof, may also be useful for treating immune regulatory disorders related to bone marrow or organ transplant rejection or graft-versus-host disease. Examples of inflammatory and immune regulatory disorders that can be treated with the compounds (or pharmaceutical compositions or combinations thereof) include, but are not limited to, transplantation of organs or tissue, graft-versus-host diseases brought about by transplantation, autoimmune syndromes including rheumatoid arthritis, systemic lupus erythematosus, Hashimoto's thyroiditis, multiple sclerosis, systemic sclerosis, systemic inflammatory response syndrome, myasthenia gravis, type I diabetes, uveitis, posterior uveitis, allergic encephalomyelitis, glomerulonephritis, postinfectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, ischemia-reperfusion injuries, inflammatory bowel diseases, necrotizing enterocolitis, intestinal lesions associated with thermal burns, celiac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis or myocardial infarction, scleroderma (including systemic scleroderma), anti-phospholipid syndrome, Wegener's granuloma, Sjögren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, retinal degeneration, retinal detachment, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic liver disease, including alcoholic cirrhosis, alcoholic steatohepatitis, non-alcoholic steatohepatitis (NASH), autoimmune hepatobiliary diseases, acetaminophen toxicity, hepatotoxicity, hepatic failure, fulminant hepatic failure, late-onset hepatic failure, "acute-on-chronic" liver failure, chronic kidney diseases, kidney damage/injury (caused by, for example, nephritis, renal transplant, surgery, administration of nephrotoxic drugs, acute kidney injury), augmentation of chemotherapeutic effect, cytomegalovirus infection, HCMV infection, AIDS, cancer, senile dementia, Parkinson's disease, trauma, or chronic bacterial infection.

In certain embodiments the present compounds are useful for treating nerve pain, including neuropathic pain and inflammation induced pain.

In certain embodiments, the compounds are useful for treating interleukin-1 converting enzyme-associated associated fever syndrome, tumor necrosis factor receptor-associated periodic syndrome, NEMO-deficiency syndrome, HOIL-1 deficiency, linear ubiquitin chain assembly complex deficiency syndrome, lysosomal storage diseases (e.g., Gaucher disease, GM2 gangliosidosis, alpha-mannosidosis, aspartylglucosaminuria, cholesteryl ester storage disease, chronic hexosaminidase A deficiency, cystinosis, Danon disease, Fabry disease, Farber disease, fucosidosis, galacto-sialidosis, GM1 gangliosidosis, mucolipidosis, infantile free sialic acid storage disease, juvenile hexosaminidase A deficiency, Krabbe disease, lysosomal acid lipase deficiency, metachromatic leukodystrophy, mucopolysaccharidoses disorders, multiple sulfatase deficiency, Niemann-Pick disease, neuronal ceroid lipofuscinoses, Pompe disease, pycnodysostosis, Sandhoff disease, Schindler disease, sialic acid storage disease, Tay-Sach disease, and Wolman disease).

In certain embodiments, the disclosed compound, combinations of disclosed compounds, or pharmaceutical compositions thereof, are useful for treating and/or preventing rheumatoid arthritis, psoriatic arthritis, osteoarthritis, systemic lupus erythematosus, lupus nephritis, ankylosing spondylitis, osteoporosis, systemic sclerosis, multiple sclerosis, psoriasis, in particular pustular psoriasis, type I diabetes, type II diabetes, inflammatory bowel disease (Crohn's disease and ulcerative colitis), hyperimmunoglobulinemia d and periodic fever syndrome, cryopyrin-associated periodic syndromes, Schnitzler's syndrome, systemic juvenile idiopathic arthritis, adult's onset Still's disease, gout, gout flares, pseudogout, sapho syndrome, Castleman's disease, sepsis, stroke, atherosclerosis, celiac disease, DIRA (deficiency of II-1 receptor antagonist), Alzheimer's disease, Huntington's disease, or Parkinson's disease.

Proliferative diseases that may be treated by the disclosed compound, combinations of disclosed compounds, or pharmaceutical compositions thereof, include benign or malignant tumors, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, undifferentiated carcinoma, papillary carcinoma, seminoma, melanoma, IL-1 driven disorders, a MyD88 driven disorder (such as ABC diffuse large B-cell lymphoma (DLBCL), Waldenström's macroglobulinemia, Hodgkin's lymphoma, primary cutaneous T-cell lymphoma or chronic lymphocytic leukemia), smoldering or indolent multiple myeloma, or hematological malignancies (including leukemia, acute myeloid leukemia (AML), DLBCL, ABC DLBCL, chronic lymphocytic leukemia (CLL), chronic lymphocytic lymphoma, chronic myeloid leukemia (CML), primary effusion lymphoma, Burkitt lymphoma/leukemia, acute lymphocytic leukemia, B-cell prolymphocytic leukemia, lymphoplasmacytic lymphoma, myelodysplastic/myeloproliferative neoplasms (MDS/MPN) such as chronic myelomonocytic leukemia (CMML, including CMML-0, CMML-1 and CMML-2), myelofibrosis, polycythemia vera, Kaposi's sarcoma, Waldenström's macroglobulinemia (WM), splenic marginal zone lymphoma, multiple myeloma, plasmacytoma, intravascular large B-cell lymphoma). In particular, the presently disclosed compounds are useful in treating drug resistant malignancies, such as those resistant to JAK inhibitors ibrutinib resistant malignancies, including ibrutinib resistant hematological malignancies, such as ibrutinib resistant CLL and ibrutinib resistant Waldenström's macroglobulinemia.

Despite CMML having certain clinical and pathological features of both a myeloproliferative neoplasm (MPN) and a myelodysplastic syndrome (MDS), CMML is classified by the World Health Organization (WHO) in a separate category of an MDS/MPN overlap group. (Arber et al. "*The 2016 revision to the World Health Organization classification of myeloid neoplasms and acute leukemia*" Blood, vol. 127, number 20, pages 2391-2405, May 19, 2016.) According to the WHO, the diagnosis of CMML now requires both the presence of persistent peripheral blood monocytosis of $\geq 1 \times 10^9$/L and monocytes accounting for $\geq 10\%$ of the white blood cell (WBC) differential count. Additionally, CMML can only be diagnosed per the definition when rearrangements in PDGFRA, PDGFRB or FGFR1 genes have been excluded, and in the 2016 update, the PCM1-JAK2 fusion gene was added as an excluding criterion. In some embodiments, a method for treating CMML comprises identifying a subject having the WHO diagnosis criteria (i.e., persistent peripheral blood monocytosis of $\geq 1 \times 10^9$/L and monocytes accounting for $\geq 10\%$ of the white blood cell differential count) and excluding rearrangements in PDGFRA, PDGFRB, FGFR1, or PCM1-JAK2 genes), and treating the subject by administering a RIP1 inhibitor disclosed herein, combinations of such compounds, and/or compositions thereof.

Examples of allergic disorders that may be treated using the disclosed compound, combinations of disclosed compounds, or pharmaceutical compositions thereof, include, but are not limited to, asthma (e.g. atopic asthma, allergic asthma, atopic bronchial IgE-mediated asthma, non-atopic asthma, bronchial asthma, non-allergic asthma, essential asthma, true asthma, intrinsic asthma caused by pathophysiologic disturbances, essential asthma of unknown or unapparent cause, emphysematous asthma, exercise-induced asthma, emotion-induced asthma, extrinsic asthma caused by environmental factors, cold air induced asthma, occupational asthma, infective asthma caused by or associated with bacterial, fungal, protozoal, or viral infection, incipient asthma, wheezy infant syndrome, bronchiolitis, cough variant asthma or drug-induced asthma), allergic bronchopulmonary aspergillosis (ABPA), allergic rhinitis, perennial allergic rhinitis, perennial rhinitis, vasomotor rhinitis, postnasal drip, purulent or non-purulent sinusitis, acute or chronic sinusitis, and ethmoid, frontal, maxillary, or sphenoid sinusitis.

As another example, rheumatoid arthritis (RA) typically results in swelling, pain, loss of motion and tenderness of target joints throughout the body. RA is characterized by chronically inflamed synovium that is densely crowded with lymphocytes. The synovial membrane, which is typically one cell layer thick, becomes intensely cellular and assumes a form similar to lymphoid tissue, including dendritic cells, T-, B- and NK cells, macrophages and clusters of plasma cells. This process, as well as a plethora of immunopathological mechanisms including the formation of antigen-immunoglobulin complexes, eventually result in destruction of the integrity of the joint, resulting in deformity, permanent loss of function and/or bone erosion at or near the joint. The disclosed compound, combinations of disclosed compounds, or pharmaceutical compositions thereof, may be used to treat, ameliorate or prevent any one, several or all of these symptoms of RA. Thus, in the context of RA, the compounds are considered to provide therapeutic benefit when a reduction or amelioration of any of the symptoms commonly associated with RA is achieved, regardless of whether the treatment results in a concomitant treatment of the underlying RA and/or a reduction in the amount of circulating rheumatoid factor ("RF").

The American College of Rheumatology (ACR) has developed criteria for defining improvement and clinical remission in RA. Once such parameter, the ACR20 (ACR criteria for 20% clinical improvement), requires a 20% improvement in the tender and swollen joint count, as well as a 20% improvement in 3 of the following 5 parameters: patient's global assessment, physician's global assessment, patient's assessment of pain, degree of disability, and level of acute phase reactant. These criteria have been expanded for 50% and 70% improvement in ACR50 and ACR70, respectively. Other criteria include Paulu's criteria and radiographic progression (e.g. Sharp score).

In some embodiments, therapeutic benefit in patients suffering from RA is achieved when the patient exhibits an ACR20. In specific embodiments, ACR improvements of ACRC50 or even ACR70 may be achieved.

B. Combinations of Therapeutic Agents

The compounds described herein may be used alone, in combination with one another, in separate pharmaceutical compositions, together in a single pharmaceutical composition, or as an adjunct to, or in combination with, other established therapies. The compound or compounds or composition comprising the compound (or compounds) may be administered once, or in plural administrations. In some embodiments, the compounds of the present invention may be used in combination with other therapeutic agents useful for the disorder or condition being treated. These other therapeutic agents may be administered simultaneously, sequentially in any order, by the same route of administration, or by a different route as the presently disclosed compounds. For sequential administration, the compound(s) and the therapeutic agent(s) may be administered such that an effective time period of at least one compound and the therapeutic agent overlaps with an effective time period of at least one other compound and/or therapeutic agent. In an exemplary embodiment of a combination comprising four components, the effective time period of the first component administered may overlap with the effective time periods of the second, third and fourth components, but the effective time periods of the second, third and fourth components independently may or may not overlap with one another. In another exemplary embodiment of a combination comprising four components, the effective time period of the first component administered overlaps with the effective time period of the second component, but not that of the third or fourth; the effective time period of the second component overlaps with those of the first and third components; and the effective time period of the fourth component overlaps with that of the third component only. In some embodiments, the effective time periods of all compounds and/or therapeutic agents overlap with each other.

In some embodiments, the compounds are administered with another therapeutic agent, such as an analgesic, an antibiotic, an anticoagulant, an antibody, an anti-inflammatory agent, an immunosuppressant, a guanylate cyclase-C agonist, an intestinal secretagogue, an antiviral, anticancer, antifungal, or a combination thereof. The anti-inflammatory agent may be a steroid or a nonsteroidal anti-inflammatory agent. In certain embodiments, the nonsteroidal anti-inflammatory agent is selected from aminosalicylates, cyclooxygenase inhibitors, diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin, or a combination thereof. In some embodiments, the immunosuppressant is mercaptopurine, a corticosteroid, an alkylating agent, a calcineurin inhibitor, an inosine monophosphate dehydrogenase inhibitor, antilymphocyte globulin, antithymocyte globulin, an anti-T-cell antibody, or a combination thereof. In one embodiment, the antibody is infliximab.

In some embodiments, the present compounds may be used with anti-cancer or cytotoxic agents. Various classes of anti-cancer and anti-neoplastic compounds include, but are not limited to, alkylating agents, antimetabolites, BCL-2 inhibitors, vinca alkyloids, taxanes, antibiotics, enzymes, cytokines, platinum coordination complexes, proteasome inhibitors, substituted ureas, kinase inhibitors, hormones and hormone antagonists, and hypomethylating agents, for example DNMT inhibitors, such as azacitidine and decitabine. Exemplary alkylating agents include, without limitation, mechlorothamine, cyclophosphamide, ifosfamide, melphalan, chlorambucil, ethyleneimines, methylmelamines, alkyl sulfonates (e.g., busulfan), and carmustine. Exemplary antimetabolites include, by way of example and not limitation, folic acid analog methotrexate; pyrmidine analog fluorouracil, cytosine arbinoside; purine analogs mercaptopurine, thioguanine, and azathioprine. Exemplary vinca alkyloids include, by way of example and not limitation, vinblastine, vincristine, paclitaxel, and colchicine. Exemplary antibiotics include, by way of example and not limitation, actinomycin D, daunorubicin, and bleomycin. An exemplary enzyme effective as an anti-neoplastic agent includes L-asparaginase. Exemplary coordination compounds include, by way of example and not limitation, cisplatin and carboplatin. Exemplary hormones and hormone related compounds include, by way of example and not limitation, adrenocorticosteroids prednisone and dexamethasone; aromatase inhibitors amino glutethimide, formestane, and anastrozole; progestin compounds hydroxyprogesterone caproate, medroxyprogesterone; and anti-estrogen compound tamoxifen.

These and other useful anti-cancer compounds are described in Merck Index, 13th Ed. (O'Neil M. J. et al., ed.) Merck Publishing Group (2001) and Goodman and Gilman's The Pharmacological Basis of Therapeutics, 12th Edition, Brunton L. L. ed., Chapters 60-63, McGraw Hill, (2011), both of which are incorporated by reference herein.

Among the CTLA 4 antibodies that can be used in combination with the presently disclosed inhbitors is ipilimumab, marketed as YERVOY® by Bristol-Myers Squibb.

Other chemotherapeutic agents for combination include immunooncology agents, such as checkpoint pathway inhibitors, for example, PD-1 inhibitors, such as nivolumab and lambrolizumab, and PD-L1 inhibitors, such as pembrolizumab, MEDI-4736 and MPDL3280A/RG7446. Additional checkpoint inhibitors for combination with the compounds disclosed herein include, Anti-LAG-3 agents, such as BMS-986016 (MDX-1408).

Further chemotherapeutic agents for combination with the presently disclosed inhibitors include Anti-SLAMF7 agents, such as the humanized monoclonal antibody elotuzumab (BMS-901608), anti-KIR agents, such as the anti-KIR monoclonal antibody lirilumab (BMS-986015), and anti-CD137 agents, such as the fully human monoclonal antibody urelumab (BMS-663513).

The presently disclosed compounds also may be used advantageously with CAR-T therapies. Example of currently available CAR-T therapies are axicabtagene ciloleucel and tisagenlecleucel.

Additional anti-proliferative compounds useful in combination with the compounds of the present invention include, by way of example and not limitation, antibodies directed against growth factor receptors (e.g., anti-Her2); and cytokines such as interferon-α and interferon-γ, interleukin-2, and GM-CSF.

Additional chemotherapeutic agents useful in combination with the present compounds include proteasome inhibitors, such as bortezomib, carfilzomib, marizomib and the like.

Examples of kinase inhibitors that are useful in combination with the presently disclosed compounds, particularly in treating malignancies include: Btk inhibitors, such as ibrutinib; CDK inhibitors, such as palbociclib; EGFR inhibitors, such as afatinib, erlotinib, gefitinib, lapatinib, osimertinib and vandetinib; Mek inhibitors, such as trametinib; Raf inhibitors, such as dabrafenib, sorafenib and vemurafenib; VEGFR inhibitors, such as axitinib, lenvatinib, nintedanib, pazopanib; BCR-Abl inhibitors, such as bosutinib, dasatinib, imatinib and nilotinib; FLT-3 inhibitors, such as gilteritinib and quizartinib, PI3-kinase inhibitors, such as idelalisib, Syk inhibitors, such as fostamatinib; and JAK inhibitors, such as ruxolitinib and fedratinib.

In other embodiments, the second therapeutic agent may be selected from any of the following:

analgesics, including morphine, fentanyl, hydromorphone, oxycodone, codeine, acetaminophen, hydrocodone, buprenorphine, tramadol, venlafaxine, flupirtine, meperidine, pentazocine, dextromoramide, dipipanone;

antibiotics, including aminoglycosides (e.g., amikacin, gentamicin, kanamycin, neomycin, netilmicin, tobramycin, and paromycin), carbapenems (e.g., ertapenem, doripenem, imipenem, cilastatin, and meropenem), cephalosporins (e.g., cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, and cefobiprole), glycopeptides (e.g., teicoplanin, vancomycin, and telavancin), lincosamides (e.g., clindamycin and incomysin), lipopeptides (e.g., daptomycin), macrolides (azithromycin, clarithromycin, dirithromycin, erythromycin, roxithromycin, troleandomycin, telithromycin, and spectinomycin), monobactams (e.g., aztreonam), nitrofurans (e.g., furazolidone and nitrofurantoin), penicilllins (e.g., amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, and ticarcillin), penicillin combinations (e.g., amoxicillin/clavulanate, ampicillin/sulbactam, piperacillin/tazobactam, and ticarcillin/clavulanate), polypeptides (e.g., bacitracin, colistin, and polymyxin B), quinolones (e.g., ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, and temafloxacin), sulfonamides (e.g., mafenide, sulfonamidochrysoidine, sulfacetamide, sulfadiazine, silver sulfadiazine, sulfamethizole, sulfamethoxazole, sulfanilimide, sulfasalazine, sulfisoxazole, trimethoprim, and trimethoprim-sulfamethoxaxzole), tetracyclines (e.g., demeclocycline, doxycycline, minocycline, oxytetracycline, and tetracycline), antimycobacterial compounds (e.g., clofazimine, dapsone, capreomycin, cycloserine, ethambutol, ethionamide, isoniazid, pyrazinamide, rifampicin (rifampin), rifabutin, rifapentine, and streptomycin), and others, such as arsphenamine, chloramphenicol, fosfomycin, fusidic acid, linezolid, metronidazole, mupirocin, platensimycin, quinuprisin/dalfopristin, rifaximin, thiamphenicol, tigecycline, and timidazole;

antibodies—including anti-TNF-α antibodies, e.g., infliximab (Remicade™), adalimumab, golimumab, certolizumab; anti-B cell antibodies, e.g., rituximab; anti-IL-6 antibodies, e.g., tocilizumab; anti-IL-1 antibodies, e.g., anakinra; anti PD-1 and/or anti-PD-L1 antibodies, e.g. nivolumab, pembrolizumab, pidilizumab, BMS-936559, MPDL3280A, AMP-224, MEDI4736; ixekizumab, brodalumab, ofatumumab, sirukumab, clenoliximab, clazakiumab, fezakinumab, fletikumab, mavrilimumab, ocrelizumab, sarilumab, secukinumab, toralizumab, zanolimumab;

anticoagulants—including warfarin (Coumadin™), acenocoumarol, phenprocoumon, atromentin, phenindione, heparin, fondaparinux, idraparinux, rivaroxaban, apixaban, hirudin, lepirudin, bivalirudin, argatrobam, dabigatran, ximelagatran, batroxobin, hementin;

anti-inflammatory agents—including steroids, e.g., budesonide, nonsteroidal anti-inflammatory agents, e.g., aminosalicylates (e.g., sulfasalazine, mesalamine, olsalazine, and balsalazide), cyclooxygenase inhibitors (COX-2 inhibitors, such as rofecoxib, celecoxib), diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin;

immunosuppressants—including mercaptopurine, corticosteroids such as dexamethasone, hydrocortisone, prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil and azathioprine, and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. Azathioprine is currently available from Salix Pharmaceuticals, Inc. under the brand name Azasan; mercaptopurine is currently available from Gate Pharmaceuticals, Inc. under the brand name Purinethol; prednisone and prednisolone are currently available from Roxane Laboratories, Inc.; Methyl prednisolone is currently available from Pfizer; sirolimus (rapamycin) is currently available from Wyeth-Ayerst under the brand name Rapamune; tacrolimus is currently available from Fujisawa under the brand name Prograf; cyclosporine is current available from Novartis under the brand name Sandimmune and Abbott under the brand name Gengraf; IMPDH inhibitors such as mycophenolate mofetil and mycophenolic acid are currently available from Roche under the brand name Cellcept and Novartis under the brand name Myfortic; azathioprine is currently available from Glaxo Smith Kline under the brand name Imuran; and antibodies are currently available from Ortho Biotech under the brand name Orthoclone, Novartis under the brand name Simulect (basiliximab) and Roche under the brand name Zenapax (daclizumab); and Guanylate cyclase-C receptor agonists or intestinal secretagogues, for example linaclotide, sold under the name Linzess.

These various agents can be used in accordance with their standard or common dosages, as specified in the prescribing information accompanying commercially available forms of the drugs (see also, the prescribing information in the 2006 Edition of The Physician's Desk Reference), the disclosures of which are incorporated herein by reference.

IV. Methods of Making Compounds

The compounds can be prepared by any suitable method as will be understood by a person of ordinary skill in the art. One exemplary suitable method is provided below with reference to specific compounds in the examples, and can include the following first reaction step according to Scheme 1.

Scheme 1

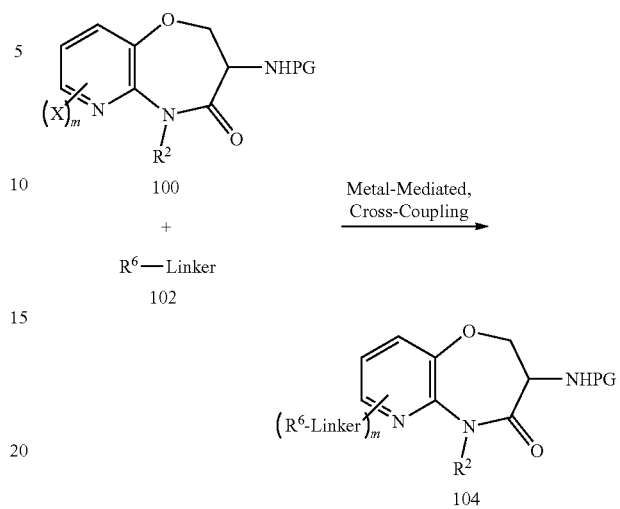

With reference to Scheme 1, protected amine precursor 100 can be coupled with $R^1$ group 102, which comprises an "$R^6$-linker" group as illustrated in Scheme 1, using a metal-mediated, cross-coupling reaction to provide the cross-coupled product 104. In some embodiments, the metal-mediated, cross-coupling reaction can be carried out using a transition metal catalyst, such as a palladium catalyst. Exemplary palladium catalysts include, but are not limited to, Pd(0) catalysts (e.g., $Pd_2(dba)_3$, $Pd(dba)_2$, $Pd(PPh_3)_4$, and the like) or Pd(II) catalyst (e.g., XPhos Pd generation 2 or generation 3, $PdCl_2$, $Pd(OAc)_2$, and the like). In some embodiments, the palladium catalyst can be used in combination with another co-catalyst, such as CuI, to promote the cross-coupling reaction, such as in a Sonogoshira reaction. The metal-mediated, cross-coupling also can comprise using a base, such as an amine base (e.g., $Et_3N$), or an inorganic base (e.g., $Cs_2CO_3$, $Na_2CO_3$, $K_2CO_3$ or the like), and a solvent (e.g., dimethylformamide). With reference to Scheme 1, X is a suitable group for metal-mediated, cross-coupling, such as a halogen or a triflate group and PG is an amine protecting group, which can be selected from, but is not limited to, a 9-fluorenylmethoxycarbonyl ("Fmoc") group, a t-butyloxycarbonyl ("Boc") group, a trityl ("Tr") group, an allyloxycarbonyl ("Alloc") group, a benzyloxycarbonyl ("Cbz") group, and the like.

Synthesis of tert-Butyl (S)-(9-Bromo-5-methyl-4-oxo-2,3,4,5-tetrahydropyrido[3,2-b][1,4]oxazepin-3-yl)carbamate 8 and tert-Butyl (S)-(7-Bromo-5-methyl-4-oxo-2,3,4,5-tetrahydropyrido[3,2-b][1,4]oxazepin-3-yl)carbamate 9

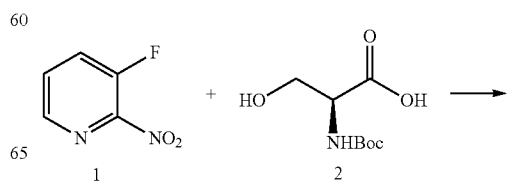

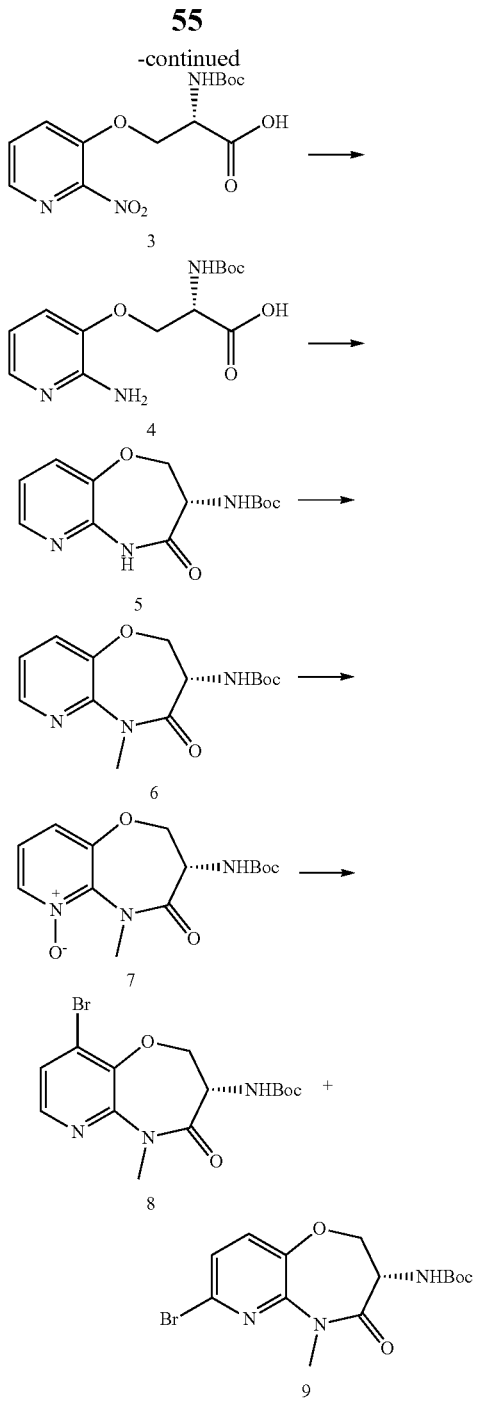

Intermediates 8 and 9 are referred to as intermediates II and I, respectively in other schemes herein.

Synthesis of N-(tert-Butoxycarbonyl)-O-(2-nitropyridin-3-yl)-L-serine (3)

To a solution of (tert-butoxycarbonyl)-L-serine 2 (5.13 g, 25.0 mmol) in anhydrous DMF (100 mL) at 0° C. was added sodium hydride (2.0 g, 60% in oil, 50 mmol). The resulting solution was stirred at this temperature for 2 hrs, then 3-fluoro-2-nitropyridine 1 (3.60 g, 25.3 mmol) was added. The resulting solution was allowed to warm up to ambient temperature over 8 hrs and quenched with aqueous HCl solution (3N, 25 mL) slowly until pH of the solution was around 4. The reaction solution was extracted with ethyl acetate (3×120 mL) and the combined organic layer was washed with brine (40 mL), dried over anhydrous magnesium sulfate, filtered and concentrated under reduced pressure. Residue obtained was purified by silica gel chromatography using a gradient of 0 to 10% methanol in dichloromethane to afford N-(tert-butoxycarbonyl)-O-(2-nitropyridin-3-yl)-L-serine 3 (5.35 g, 65%) as a pale yellow solid. $^1$H NMR (400 MHz, CDCl$_3$) δ 8.18-8.08 (m, 1H), 7.57 (d, J=3.3 Hz, 2H), 5.60 (d, J=7.9 Hz, 1H), 4.76 (d, J=7.8 Hz, 1H), 4.64 (dd, J=9.3, 2.9 Hz, 1H), 4.46 (dd, J=9.3, 3.1 Hz, 1H), 1.46 (s, 9H). MS (ESI, m/e) Calculated 327.1066; Found 228.1 [M-Boc+H]$^+$.

Synthesis of O-(2-Aminopyridin-3-yl)-N-(tert-butoxycarbonyl)-L-serine (4)

To a solution of N-(tert-butoxycarbonyl)-O-(2-nitropyridin-3-yl)-L-serine 3 (4.81 g, 14.72 mmol) in methanol (100 mL) was added 5% palladium on carbon (950 mg). The resulting solution was hydrogenated in Parr-Shaker under 60 PSI for 16 hrs, filtered through Celite and washed with methanol. The filtrate was concentrated under reduced pressure to afford crude product 0-(2-aminopyridin-3-yl)-N-(tert-butoxycarbonyl)-L-serine 4 (4.40 g, >95% yield) as a pale, yellow solid which was directly used in next step without purification. MS (ESI, m/e) Calculated 297.1325; Found 298.0 [M+H]$^+$.

Synthesis of tert-Butyl (S)-(4-oxo-2,3,4,5-tetrahydropyrido[3,2-b][1,4]oxazepin-3-yl)carbamate (5)

To a solution of crude O-(2-aminopyridin-3-yl)-N-(tert-butoxycarbonyl)-L-serine 4 (4.40 g, 14.72 mmol) in anhydrous DMF (300 mL) was added diisopropylethylamine (2.09 g, 2.80 mL, 16.19 mmol) followed by HATU (6.16 g, 16.19 mmol). The resulting solution was stirred at ambient temperature for 2 days, water (200 mL) was then added, and the aqueous solution was extracted with ethyl acetate (4×200 mL). Combined organic layer was dried over anhydrous magnesium sulfate, filtered and concentrated under reduced pressure. The residue obtained was purified by silica gel chromatography a gradient of using 0 to 5% methanol in dichloromethane to afford tert-butyl (S)-(4-oxo-2,3,4,5-tetrahydropyrido[3,2-b][1,4]oxazepin-3-yl)carbamate 5 (899 mg, 22% over 2 steps) as a white solid. $^1$H NMR (400 MHz, CDCl$_3$) δ 8.86 (s, 1H), 8.16 (dd, J=4.7, 1.5 Hz, 1H), 7.42 (dd, J=8.0, 1.5 Hz, 1H), 7.08 (dd, J=8.0, 4.7 Hz, 1H), 5.64 (s, 1H), 4.73-4.47 (m, 2H), 4.17 (dd, J=10.7, 9.4 Hz, 1H), 1.46 (s, 9H). MS (ESI, m/e) Calculated 279.1219; Found 280.1 [M+H]$^+$.

Synthesis of tert-Butyl (S)-(5-methyl-4-oxo-2,3,4,5-tetrahydropyrido[3,2-b][1,4]oxazepin-3-yl)carbamate (6)

To a solution of tert-butyl (S)-(4-oxo-2,3,4,5-tetrahydropyrido[3,2-b][1,4]oxazepin-3-yl) carbamate 5 (796 mg, 2.85 mmol) in anhydrous DMF (28 mL) was added anhydrous cesium carbonate (930 mg, 2.85 mmol) followed by methyl iodide (368 mg, 162 μL, 2.59 mmol). The resulting solution was stirred at ambient temperature for 2 days, followed by addition of water (100 mL) and ethyl acetate (100 mL). The organic layer was separated, and the aqueous layer was extracted with ethyl acetate (2×50 mL). The combined organic layer was then washed with brine (50 mL), dried over anhydrous magnesium sulfate, filtered and concentrated under reduced pressure to obtain a residue in DMF solution (about 12 mL). Crude product was purified by reverse HPLC using a gradient of 0 to 50% acetonitrile in water buffered with 0.1% formic acid. The desired fractions were combined, basified with saturated sodium bicarbonate aqueous solution and extracted with ethyl acetate. The combined organic layer was dried over anhydrous magnesium sulfate, filtered and concentrated under the reduced pressure to afford tert-butyl (S)-(5-methyl-4-oxo-2,3,4,5-tetrahydropyrido[3,2-b][1,4]oxazepin-3-yl)carbamate 6 (434 mg, 57%) as a white solid. $^1$H NMR (400 MHz, CDCl$_3$) δ 8.28 (dd, J=4.8, 1.6 Hz, 1H), 7.47 (dd, J=7.9, 1.6 Hz, 1H), 7.14 (dd, J=7.9, 4.7 Hz, 1H), 5.59 (d, J=5.2 Hz, 1H), 4.73-4.53 (m, 2H), 4.31-4.12 (m, 1H), 3.51 (s, 3H), 1.41 (s, 9H). MS (ESI, m/e) Calculated 293.1376; Found 194.1 [M-Boc+H]$^+$.

Synthesis of (S)-3-((tert-Butoxycarbonyl)amino)-5-methyl-4-oxo-2,3,4,5-tetrahydropyrido[3,2-b][1,4]oxazepine 6-oxide (7)

To a solution of tert-butyl (S)-(5-methyl-4-oxo-2,3,4,5-tetrahydropyrido[3,2-b][1,4]oxazepin-3-yl)carbamate 6 (429 mg, 1.46 mmol) in anhydrous dichloromethane (5 mL) was added mCPBA (730 mg, 77% max purity, 2.93 mmol). The resulting solution was stirred at ambient temperature for 20 hrs, diluted with dichloromethane (200 mL) and washed with saturated sodium carbonate aqueous solution (20 mL) and saturated sodium thiosulfate solution (20 mL). Resulting organic layer was separated, washed with brine (2×30 mL), dried over anhydrous magnesium sulfate, filtered and concentrated under reduced pressure. Residue obtained was purified by silica gel chromatography using a gradient of 0 to 5% methanol in dichloromethane to afford (S)-3-((tert-butoxycarbonyl)amino)-5-methyl-4-oxo-2,3,4,5-tetrahydropyrido[3,2-b][1,4]oxazepine 6-oxide 7 (303 mg, 67%). MS (ESI, m/e) Calculated 309.1325; Found 310.0 [M+H]$^+$. Starting material tert-butyl (S)-(5-methyl-4-oxo-2,3,4,5-tetrahydropyrido[3,2-b][1,4]oxazepin-3-yl)carbamate 6 (139 mg, 32%) was partially recovered.

Synthesis of tert-Butyl (S)-(9-bromo-5-methyl-4-oxo-2,3,4,5-tetrahydropyrido[3,2-b][1,4]oxazepin-3-yl)carbamate (8) and tert-butyl (S)-(7-bromo-5-methyl-4-oxo-2,3,4,5-tetrahydropyrido[3,2-b][1,4]oxazepin-3-yl)carbamate (9)

To a solution of (S)-3-((tert-butoxycarbonyl)amino)-5-methyl-4-oxo-2,3,4,5-tetrahydropyrido [3,2-b][1,4] oxazepine 6-oxide 7 (303 mg, 0.98 mmol) in anhydrous 1,2-dichloroethane (20 mL) was added 4 Å molecular sieves (303 mg) followed by n-tetrabutylammonium bromide (474 mg, 1.47 mmol). The reaction solution was allowed to stir at ambient temperature for 10 minutes, then 4-methylbenzenesulfonic anhydride (480 mg, 1.47 mmol) was added. The resulting reaction mixture was then allowed to stir at ambient temperature for 17 hrs and heated at 65° C. for 8 hrs, cooled down to ambient temperature, filtered through Celite and washed with dichloromethane (about 100 mL). The filtrate was then washed with saturated sodium bicarbonate aqueous solution, brine, dried over anhydrous magnesium sulfate, filtered and concentrated under reduced pressure. The residue obtained was purified by silica gel chromatography using a gradient of 0 to 10% methanol in dichloromethane to afford less polar isomer of tert-butyl (S)-(7-bromo-5-methyl-4-oxo-2,3,4,5-tetrahydropyrido[3,2-b][1,4]oxazepin-3-yl)carbamate 9 (67 mg, 18%) as a white solid.

$^1$H NMR (400 MHz, DMSO-d$_6$) δ 7.59 (d, J=8.2 Hz, 1H), 7.49 (d, J=8.2 Hz, 1H), 7.30 (d, J=7.0 Hz, 1H), 4.50-4.21 (m, 3H), 3.27 (s, 3H), 1.33 (s, 9H). MS (ESI, m/e) Calculated 371.0481; Found 372.0 [M+H]$^+$. Additional impure fractions were combined and further purified by reverse HPLC using a gradient of 35 to 80% acetonitrile in water buffered with 0.10% formic acid. The desired fractions were combined and lyophilized to afford the more polar isomer of tert-butyl (S)-(9-bromo-5-methyl-4-oxo-2,3,4,5-tetrahydropyrido[3,2-b][1,4]oxazepin-3-yl) carbamate 8 (85 mg, 23%) as a white solid. $^1$H NMR (400 MHz, DMSO-d$_6$) δ 8.19 (d, J=5.2 Hz, 1H), 7.63 (d, J=5.2 Hz, 1H), 7.38-7.27 (m, 1H), 4.51-4.32 (m, 3H), 3.32 (s, 3H), 1.35 (s, 9H). MS (ESI, m/e) Calculated 371.0481; Found 372.0 [M+H]$^+$. Also starting material (S)-3-((tert-butoxycarbonyl)amino)-5-methyl-4-oxo-2,3,4,5-tetrahydropyrido [3,2-b][1,4]oxazepine 6-oxide 7 (61 mg, 20%) was partially recovered.

Synthesis of (S)—N-(5-Methyl-4-oxo-7-(8-oxa-2-azaspiro[4.5]decan-2-yl)-2,3,4,5-tetrahydropyrido[3,2-b][1,4]oxazepin-3-yl)-4-phenoxypicolinamide 14

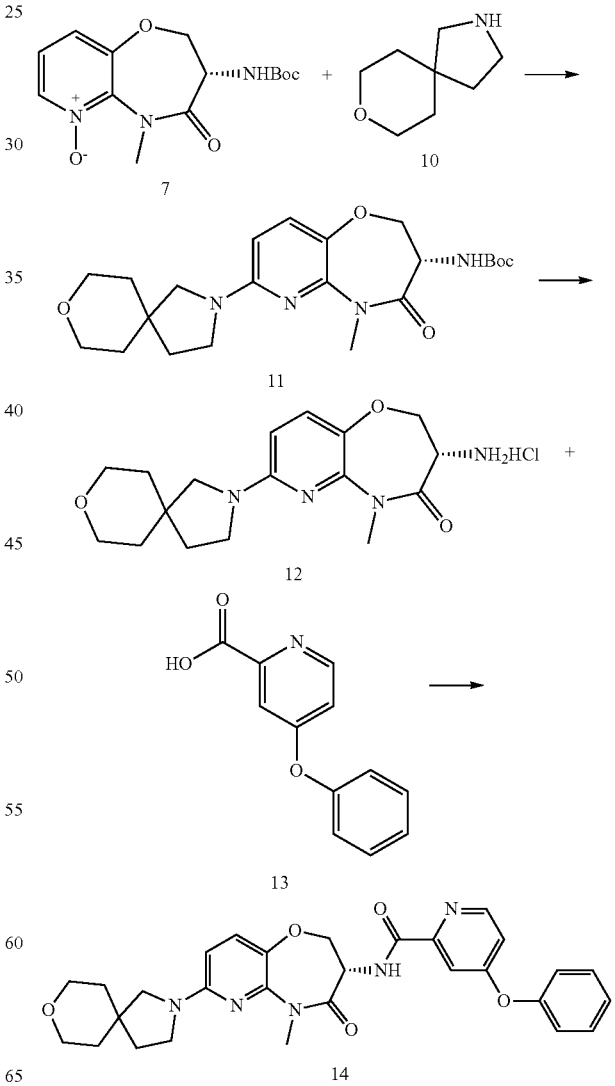

Synthesis of tert-Butyl (S)-(5-Methyl-4-oxo-7-(8-oxa-2-azaspiro[4.5]decan-2-yl)-2,3,4,5-tetrahydropyrido[3,2-b][1,4]oxazepin-3-yl)carbamate 11

To a solution of (S)-3-((tert-butoxycarbonyl)amino)-5-methyl-4-oxo-2,3,4,5-tetrahydropyrido [3,2-b][1,4] oxazepine 6-oxide 7 (24.5 mg, 0.079 mmol) and 8-oxa-2-azaspiro[4.5]decane 10 (14.6 mg, 0.103 mmol) in anhydrous dichloroethane (1 mL) was added diisopropylethylamine (41 mg, 55 µL, 0.317 mmol) followed by PyBrOP (48 mg, 0.103 mmol). The resulting solution was stirred at ambient temperature for 19 hrs, then heated at 60° C. for 2 days. All solvents were removed under reduced pressure and the residue obtained was purified by reverse HPLC using a gradient of 0 to 80% acetonitrile in water buffered with 0.1% formic acid. The desired fractions were combined, diluted with ethyl acetate and the solution was washed with saturated sodium bicarbonate aqueous solution, brine, dried over anhydrous magnesium sulfate, filtered and concentrated under reduced pressure to afford tert-butyl (S)-(5-methyl-4-oxo-7-(8-oxa-2-azaspiro[4.5]decan-2-yl)-2,3,4,5-tetrahydropyrido [3,2-b][1,4]oxazepin-3-yl)carbamate 11 (2.8 mg, 8%). MS (ESI, m/e) Calculated 432.2373; Found 433.2 $[M+H]^+$.

Synthesis of (S)-3-Amino-5-methyl-7-(8-oxa-2-azaspiro[4.5]decan-2-yl)-2,3-dihydropyrido[3,2-b][1,4]oxazepin-4 (5H)-one Hydrochloride 12

Hydrogen chloride solution (0.5 mL, 4.0M in dioxane, 2 mmol) was added to a vial containing tert-butyl (S)-(5-methyl-4-oxo-7-(8-oxa-2-azaspiro[4.5]decan-2-yl)-2,3,4,5-tetrahydropyrido [3,2-b][1,4]oxazepin-3-yl)carbamate 11 (2.8 mg) and the resulting solution was stirred at ambient temperature for 16 hrs. The reaction mixture was then concentrated under reduced pressure to afford crude product (S)-3-amino-5-methyl-7-(8-oxa-2-azaspiro[4.5]decan-2-yl)-2,3-dihydropyrido[3,2-b][1,4]oxazepin-4 (5H)-one hydrochloride 12 (2.4 mg, >95% yield) which was used directly in next step. MS (ESI, m/e) Calculated 332.1848; Found 333.1 $[M+H]^+$.

Synthesis of (S)—N-(5-Methyl-4-oxo-7-(8-oxa-2-azaspiro[4.5]decan-2-yl)-2,3,4,5-tetrahydropyrido[3,2-b][1,4]oxazepin-3-yl)-4-phenoxypicolinamide 14

To a solution of (S)-3-amino-5-methyl-7-(8-oxa-2-azaspiro[4.5]decan-2-yl)-2,3-dihydropyrido[3,2-b][1,4]oxazepin-4 (5H)-one hydrochloride 12 (2.4 mg, 6.48 µmol) and 4-phenoxypicolinic acid 13 (2.8 mg, 13 µmol) in anhydrous DMF (0.5 mL) was added diisopropylethylamine (4.2 mg, 5.6 µL, 32 µmol) followed by HATU (4.9 mg, 13 µmol). The resulting solution was stirred at ambient temperature for 16 hrs. A drop of water was added to quench the reaction and the resulting solution was directly purified by reverse HPLC using a gradient of 40 to 100% acetonitrile in water buffered with 0.1% formic acid. Desired fractions were combined and diluted with ethyl acetate (60 mL). The solution was washed with saturated sodium bicarbonate aqueous solution, brine, dried over anhydrous magnesium sulfate, filtered and concentrated under reduced pressure to afford (S)—N-(5-methyl-4-oxo-7-(8-oxa-2-azaspiro[4.5]decan-2-yl)-2,3,4,5-tetrahydropyrido [3,2-b][1,4]oxazepin-3-yl)-4-phenoxypicolinamide 14 (2.2 mg, 64%) as a white solid. MS (ESI, m/e) Calculated 529.2325; Found 530.2 $[M+H]^+$.

Synthesis of (S)—N-(5-Methyl-4-oxo-7-(7-oxa-2-azaspiro[3.5]nonan-2-yl)-2,3,4,5-tetrahydro-pyrido[3,2-b][1,4] oxazepin-3-yl)-4-phenoxypicolinamide 18

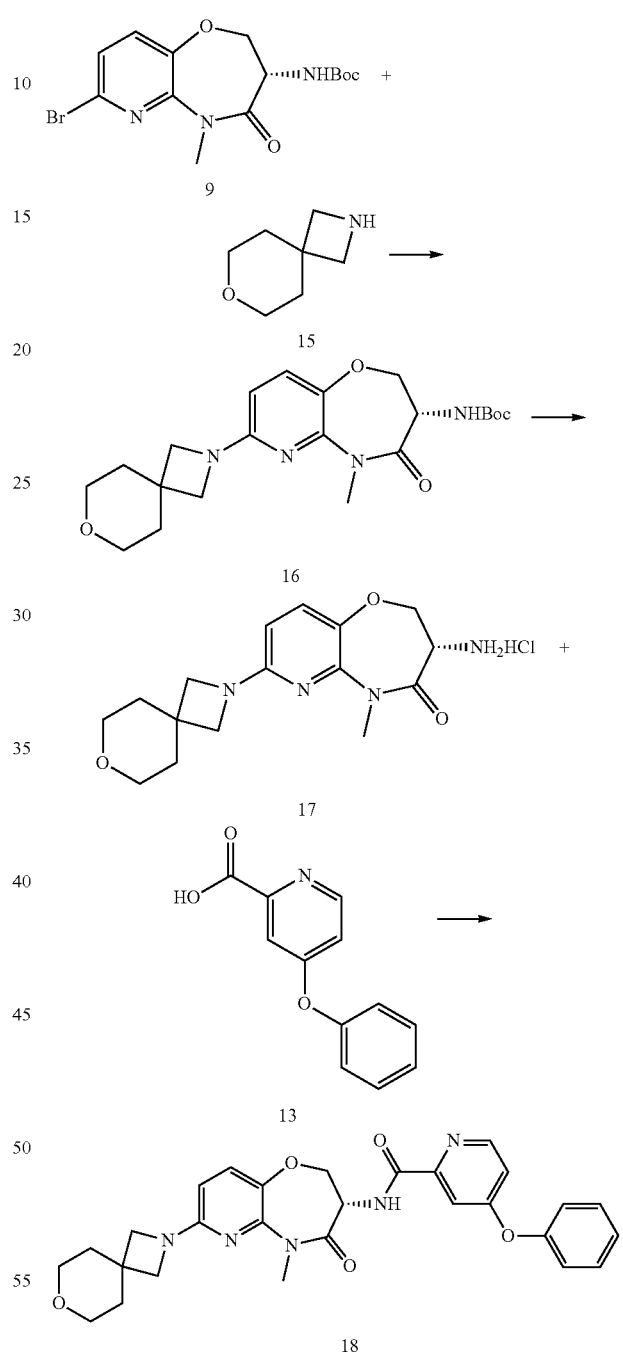

Synthesis of tert-Butyl (S)-(5-Methyl-4-oxo-7-(7-oxa-2-azaspiro[3.5]nonan-2-yl)-2,3,4,5-tetrahydropyrido[3,2-b][1,4]oxazepin-3-yl)carbamate 16

To a solution of tert-butyl (S)-(7-bromo-5-methyl-4-oxo-2,3,4,5-tetrahydropyrido[3,2-b][1,4]oxazepin-3-yl)carbamate 9 (32 mg, 85 µmol), $Pd_2(dba)_3$ (7.8 mg, 8.5 µmol), xantphos (4.9 mg, 8.5 µmol) and cesium carbonate (56 mg, 170 µmol) in anhydrous 1,4-dioxane (1 mL) was added 7-oxa-2-azaspiro[3.5]nonane (13 mg, 102 µmol). The reaction solution was purged with nitrogen for 1 minute, sealed and heated at 90° C. for 16 hrs. The reaction solution was cooled to ambient temperature and diluted with ethyl acetate (50 mL). The resulting solution was washed with water, brine, dried over anhydrous magnesium sulfate, filtered and concentrated under reduced pressure. The residue obtained was purified by reverse HPLC using a gradient of 30 to 80% acetonitrile in water buffered with 0.1% formic acid. The desired fractions were combined, diluted with ethyl acetate (100 mL) and washed saturated sodium bicarbonate aqueous solution, brine, dried over anhydrous magnesium sulfate, filtered and concentrated under reduced pressure to afford tert-butyl (S)-(5-methyl-4-oxo-7-(7-oxa-2-azaspiro[3.5] nonan-2-yl)-2,3,4,5-tetrahydropyrido[3,2-b][1,4]oxazepin-3-yl)carbamate 16 (35 mg, >95% yield) as a pale liquid. MS (ESI, m/e) Calculated 418.2216; Found 419.2 [M+H]⁺.

Synthesis of (S)-3-Amino-5-methyl-7-(7-oxa-2-azaspiro[3.5]nonan-2-yl)-2,3-dihydropyrido[3,2-b][1,4] oxazepin-4 (5H)-one Hydrochloride 17

Hydrogen chloride solution (0.5 mL, 4M in dioxane, 2 mmol) was added to a vial containing tert-butyl (S)-(5-methyl-4-oxo-7-(7-oxa-2-azaspiro[3.5]nonan-2-yl)-2,3,4,5-tetrahydropyrido [3,2-b][1,4]oxazepin-3-yl)carbamate 16 (35 mg, 0.085 mmol) and the reaction mixture was allowed to stir at ambient temperature for 16 hrs. All solvents were removed under reduced pressure to afford 1:1 mixture of azetidine ring-opening side product and the desired product (S)-3-amino-5-methyl-7-(7-oxa-2-azaspiro[3.5]nonan-2-yl)-2,3-dihydropyrido[3,2-b][1,4]oxazepin-4 (5H)-one hydrochloride 17 which was used directly in next step without purification. MS (ESI, m/e) Calculated 318.1692; Found 319.1 [M+H]⁺.

Synthesis of (S)—N-(5-Methyl-4-oxo-7-(7-oxa-2-azaspiro[3.5]nonan-2-yl)-2,3,4,5-tetrahydro-pyrido [3,2-b][1,4] oxazepin-3-yl)-4-phenoxypicolinamide 18

Crude product (S)-3-amino-5-methyl-7-(7-oxa-2-azaspiro [3.5]nonan-2-yl)-2,3-dihydropyrido[3,2-b][1,4]oxazepin-4 (5H)-one hydrochloride 17 and 4-phenoxypicolinic acid 13 (27.5 mg, 0.128 mmol) were dissolved in anhydrous DMF (1 mL), and diisopropylethylamine (55 mg, 74 µL, 0.425 mmol) was added followed by HATU (48.5 mg, 0.128 mmol). The resulting solution was stirred at ambient temperature for 16 hrs. Two drops of water were added to quench the reaction, and the resulting solution was directly purified by reverse HPLC using a gradient of 40 to 80% acetonitrile in water buffered with 0.1% formic acid. Desired fractions were combined, diluted with ethyl acetate (60 mL) and the resulting organic solution was washed with saturated sodium bicarbonate aqueous solution (5 mL), brine, dried over anhydrous magnesium sulfate, filtered and concentrated under reduced pressure. Product obtained was dissolved in 80% acetonitrile in water and lyophilized to afford (S)—N-(5-methyl-4-oxo-7-(7-oxa-2-azaspiro[3.5]nonan-2-yl)-2,3,4,5-tetrahydropyrido[3,2-b][1,4]oxazepin-3-yl)-4-phenoxypicolinamide 18 (5.7 mg, 13% over 2 steps). MS (ESI, m/e) Calculated 515.2169; Found 516.1 [M+H]⁺.

General Procedure to Prepare 9-Substituted Pyridooxaazepine Compounds

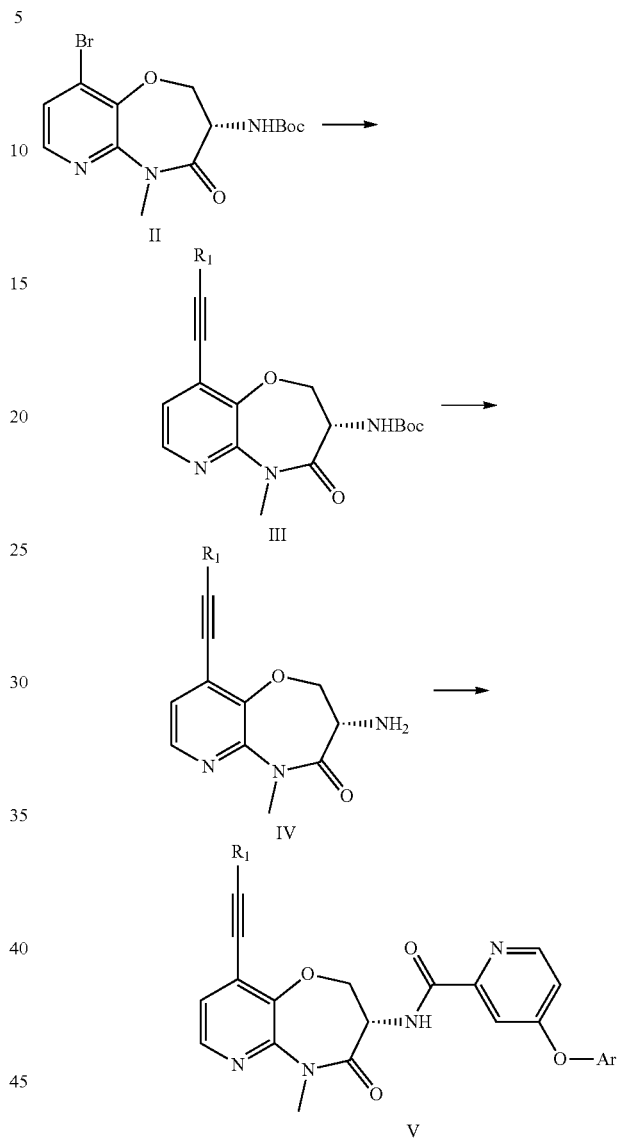

Exemplary 9-substituted pyridooxaazepine compounds were prepared according to the general procedure set forth above. Versatile intermediate II can be coupled with a variety of groups, via metal-catalyzed (for example palladium-catalyzed) cross coupling reactions as is known to those of skill in the art. In particular alkynyl groups can be readily coupled to the pyridooxezepine ring according to this general scheme by adapting the procedures set forth below. By way of example, compounds I-14, I-15 and I-16 were synthesized by this method.

Step 1: Synthesis of Intermediate (III)

Intermediate II (0.1 mmol, 1 eq), substituted ethyne (0.2 to 0.3 mmol, 2 to 3 eq), Pd(PPh₃)₄ (0.01 mmol, 0.1 eq) and CuI (0.01 mmol, 0.1 eq) in anhydrous DMF (1 mL) in a vial was added Et₃N (0.4 mmol, 4 eq). The reaction solution was purged with nitrogen for 1 minute, then sealed and heated at 70° C. for 14 to 24 hours. Reaction solution was cooled to ambient temperature, diluted with ethyl acetate (100 mL), washed with brine, dried over anhydrous magnesium sulfate, filtered, and concentrated under the reduced pressure. Residue obtained was purified by silica gel chromatography or reverse HPLC (mobile phase A: water with 0.1% HCOOH; mobile phase B: acetonitrile with 0.1% HCOOH) to afford intermediate III.

Step 2: Synthesis of Intermediate (IV)

Intermediate III (1 eq) was dissolved in dichloromethane, then TFA (concentration: 10% in dichloromethane) or HCl (40 eq, 4N in dioxane) was added. The resulting solution was stirred at ambient temperature until all starting material disappeared (monitored by reverse HPLC). All solvents were removed under the reduced pressure to afford crude product of intermediate IV which was directly used in next step.

Step 3: Synthesis of Final Product (V)

Intermediate IV (1 eg), corresponding acid (1.2 eg), and diisopropylethylamine (5 eq) were dissolved in DMF (concentration 0.05M to 0.1M), then HATU (1.2 eq) was added. The resulting solution was stirred at ambient temperature for 14 to 24 hours. Reaction solution was added brine and ethyl acetate. Organic layer was separated and dried over anhydrous magnesium sulfate, filtered, and concentrated under the reduced pressure. Residue obtained was purified by silica gel chromatography or reverse HPLC (mobile phase A: water with 0.1% HCOOH; mobile phase B: acetonitrile with 0.1% HCOOH) to afford final product (V).

Synthesis of (S)—N-(9-Bromo-5-methyl-4-oxo-2,3,4,5-tetrahydropyrido[3,2-b][1,4]oxazepin-3-yl)-4-phenoxypicolinamide 21

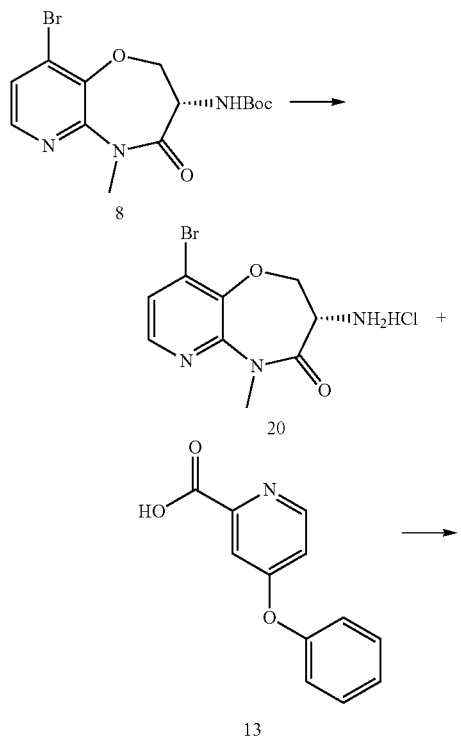

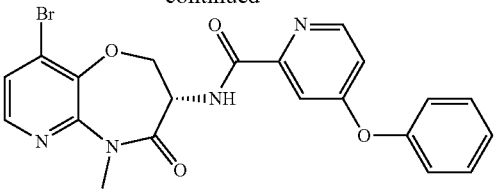

Synthesis of (S)-3-Amino-9-bromo-5-methyl-2,3-dihydropyrido[3,2-b][1,4]oxazepin-4 (5H)-one Hydrochloride 20

Hydrogen chloride solution (1 mL, 4M in dioxane, 4 mmol) was added to a vial containing tert-butyl (S)-(9-bromo-5-methyl-4-oxo-2,3,4,5-tetrahydropyrido[3,2-b][1,4]oxazepin-3-yl) carbamate 8 (52 mg, 0.139 mmol). The resulting solution was stirred at ambient temperature for 19 hrs. All solvents were removed under reduced pressure to afford (S)-3-amino-9-bromo-5-methyl-2,3-dihydropyrido[3,2-b][1,4]oxazepin-4 (5H)-one hydrochloride 20 (43 mg, 100%) as a white solid. MS (ESI, m/e) Calculated 270.9956; Found 272.0 [M+H]$^+$.

(S)—N-(9-Bromo-5-methyl-4-oxo-2,3,4,5-tetrahydropyrido[3,2-b][1,4]oxazepin-3-yl)-4-phenoxypicolinamide 21

To a solution of (S)-3-amino-9-bromo-5-methyl-2,3-dihydropyrido[3,2-b][1,4]oxazepin-4 (5H)-one hydrochloride 20 (43 mg, 85.8 μmol) and 4-phenoxypicolinic acid 13 (45 mg, 0.209 mmol) in anhydrous DMF (1.4 mL) was added diisopropylethylamine (135.2 mg, 0.18 mL, 1.05 mmol) followed by HATU (79.5 mg, 0.209 mmol). The resulting solution was stirred at ambient temperature for 16 hrs. Water (0.1 mL) was then added, and the solution was directly purified by reverse HPLC using a gradient of 37 to 90% acetonitrile in water buffered with 0.1% formic acid. The desired fractions were combined, diluted with ethyl acetate (100 mL) and the resulting solution was washed with saturated sodium bicarbonate solution, brine, dried over anhydrous magnesium sulfate, filtered and concentrated under reduced pressure to afford (S)—N-(9-bromo-5-methyl-4-oxo-2,3,4,5-tetrahydropyrido[3,2-b][1,4]oxazepin-3-yl)-4-phenoxypicolinamide 21 (50 mg, 77%) as a white solid. MS (ESI, m/e) Calculated 468.0433; Found 469.0 [M+H]$^+$.

Synthesis of (S)—N-(9-((3-Hydroxyoxetan-3-yl) ethynyl)-5-methyl-4-oxo-2,3,4,5-tetrahydro-pyrido[3,2-b][1,4]oxazepin-3-yl)-4-phenoxypicolinamide 23 (I-15)

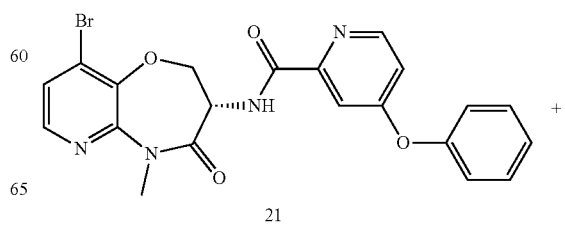

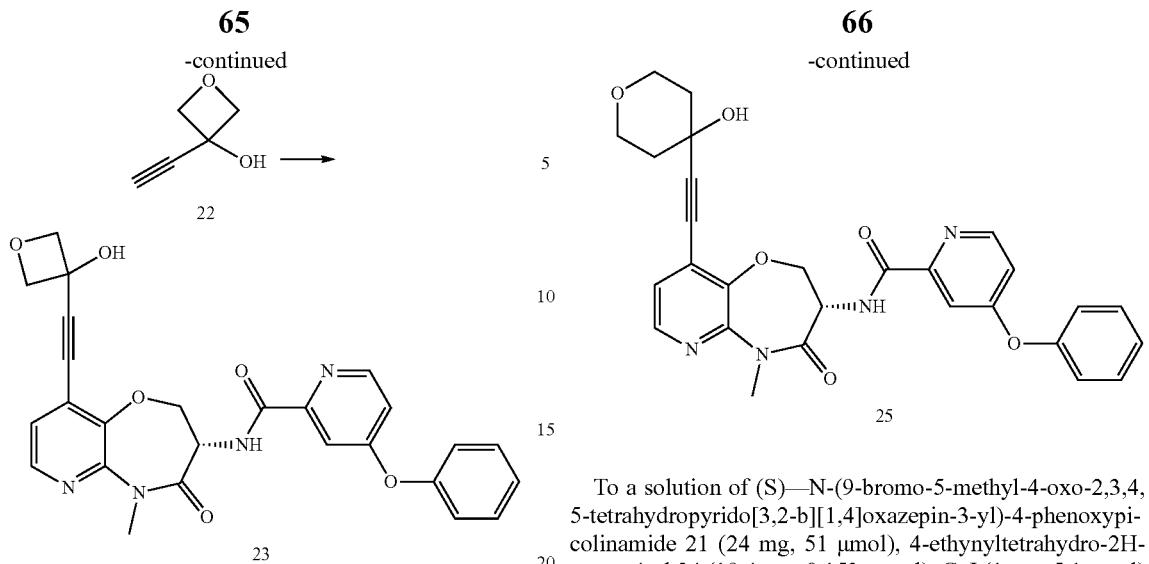

To a solution of (S)—N-(9-bromo-5-methyl-4-oxo-2,3,4,5-tetrahydropyrido[3,2-b][1,4]oxazepin-3-yl)-4-phenoxypicolinamide 21 (25 mg, 53 μmol), 3-ethynyloxetan-3-ol 22 (15.7 mg, 0.160 mmol), CuI (1 mg, 5.3 μmol) and Pd(PPh$_3$)$_4$ (6.2 mg, 5.3 μmol) in anhydrous DMF (1 mL) was added triethylamine (32.4 mg, 45 μL, 0.320 mmol). The reaction solution was purged with nitrogen for 1 minute, then sealed and heated at 70° C. for 16 hrs, cooled down to ambient temperature and diluted with ethyl acetate (60 mL). The diluted reaction mixture was then washed with brine, dried over anhydrous magnesium sulfate, filtered and concentrated under reduced pressure. The resulting residue was purified by reverse phase HPLC using a gradient of 27 to 67% acetonitrile in water buffered with 0.1% formic acid. The desired fractions were combined and lyophilized to afford (S)—N-(9-((3-hydroxyoxetan-3-yl)ethynyl)-5-methyl-4-oxo-2,3,4,5-tetrahydropyrido[3,2-b][1,4]oxazepin-3-yl)-4-phenoxypicolinamide 23 (8.5 mg, 33%) as a white solid. MS (ESI, m/e) Calculated 486.1539; Found 487.1 [M+H]$^+$.

Synthesis of (S)—N-(9-((4-Hydroxytetrahydro-2H-pyran-4-yl)ethynyl)-5-methyl-4-oxo-2,3,4,5-tetrahydropyrido[3,2-b][1,4]oxazepin-3-yl)-4-phenoxypicolinamide 25 (I-16)

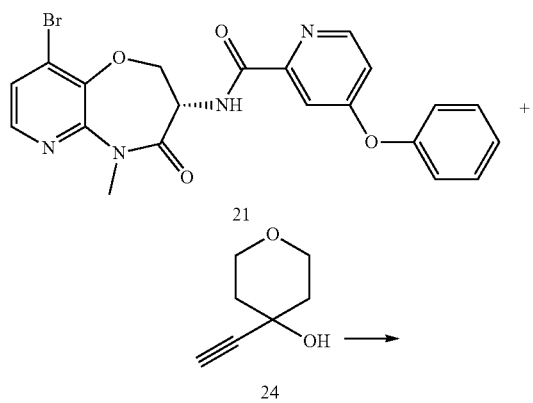

To a solution of (S)—N-(9-bromo-5-methyl-4-oxo-2,3,4,5-tetrahydropyrido[3,2-b][1,4]oxazepin-3-yl)-4-phenoxypicolinamide 21 (24 mg, 51 μmol), 4-ethynyltetrahydro-2H-pyran-4-ol 24 (19.4 mg, 0.153 mmol), CuI (1 mg, 5.1 μmol) and Pd(PPh$_3$)$_4$ (5.9 mg, 5.1 μmol) in anhydrous DMF (1 mL) was added triethylamine (31 mg, 43 μL, 0.307 mmol). The reaction mixture was then purged with nitrogen for 1 minute, sealed and heated at 70° C. for 16 hrs, cooled down to ambient temperature and diluted with ethyl acetate (60 mL). The reaction mixture was washed with brine, dried over anhydrous magnesium sulfate, filtered and concentrated under reduced pressure and the resulting residue was purified by reverse HPLC using a gradient of 27 to 67% acetonitrile in water buffered with 0.1% formic acid. The desired fractions were combined and lyophilized to afford (S)—N-(9-((4-hydroxytetrahydro-2H-pyran-4-yl)ethynyl)-5-methyl-4-oxo-2,3,4,5-tetrahydropyrido[3,2-b][1,4]oxazepin-3-yl)-4-phenoxypicolinamide 25 (13.6 mg, 52%) as a white solid. MS (ESI, m/e) Calculated 514.1852; Found 515.1 [M+H]$^+$.

Synthesis of (S)—N-(9-(3-Hydroxy-3-methylbut-1-yn-1-yl)-5-methyl-4-oxo-2,3,4,5-tetra-hydropyrido[3,2-b][1,4]oxazepin-3-yl)-4-phenoxypicolinamide 29 (I-14)

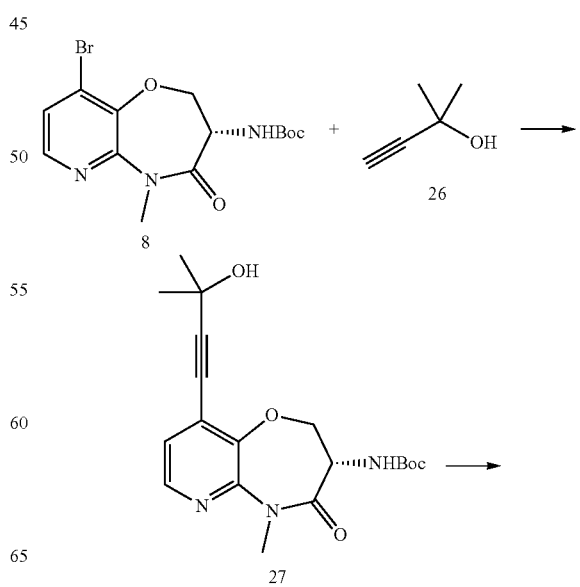

67

-continued

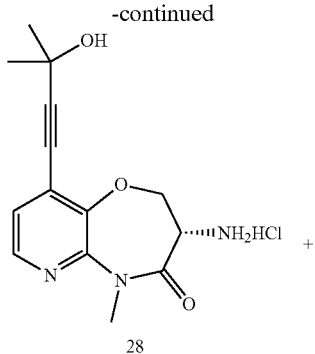

28

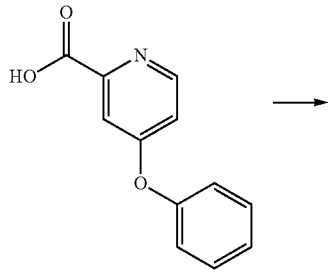

13

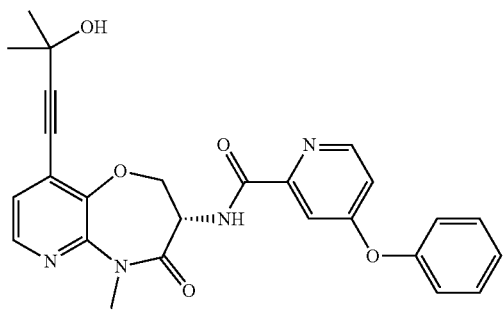

29

Synthesis of tert-Butyl (S)-(9-(3-hydroxy-3-methyl-but-1-yn-1-yl)-5-methyl-4-oxo-2,3,4,5-tetrahydro-pyrido[3,2-b][1,4]oxazepin-3-yl)carbamate 27

To a solution of tert-butyl (S)-(9-bromo-5-methyl-4-oxo-2,3,4,5-tetrahydropyrido[3,2-b][1,4]oxazepin-3-yl)carbamate 8 (32 mg, 0.086 mmol) and 2-methylbut-3-yn-2-ol 26 (22 mg, 0.257 mmol) in anhydrous DMF (1 mL) were added Pd(PPh$_3$)$_4$ (9.9 mg, 8.6 μmol), CuI (1.6 mg, 8.6 μmol) and triethylamine (52 mg, 72 μL, 0.515 mmol). The reaction mixture was then purged with nitrogen for 1 minute, sealed and heated at 70° C. for 22 hrs, cooled down to ambient temperature and diluted with ethyl acetate (80 mL). The resulting organic mixture was washed with water (20 mL), brine (20 mL), dried over anhydrous magnesium sulfate, filtered and concentrated under reduced pressure. The residue obtained was purified by reverse phase HPLC using a gradient of 20 to 70% acetonitrile in water buffered with 0.1% formic acid. The desired fractions were combined and diluted with ethyl acetate, washed with saturated sodium bicarbonate aqueous solution, brine, dried over anhydrous magnesium sulfate, filtered and concentrated under reduced pressure to afford tert-butyl (S)-(9-(3-hydroxy-3-methylbut-1-yn-1-yl)-5-methyl-4-oxo-2,3,4,5-tetrahydropyrido[3,2-b][1,4]oxazepin-3-yl)carbamate 27 (32 mg, >95% yield). MS (ESI, m/e) Calculated 375.1794; Found 320.0 [M-$^t$Bu+H]$^+$.

68

Synthesis of (S)-3-Amino-9-(3-hydroxy-3-methyl-but-1-yn-1-yl)-5-methyl-2,3-dihydropyrido[3,2-b][1,4] oxazepin-4 (5H)-one hydrochloride 28

To a solution of tert-butyl (S)-(9-(3-hydroxy-3-methyl-but-1-yn-1-yl)-5-methyl-4-oxo-2,3,4,5-tetrahydropyrido[3,2-b][1,4]oxazepin-3-yl)carbamate 27 (32 mg, 0.086 mmol) in anhydrous 1,4-dioxane (2 mL) was added hydrogen chloride solution (0.2 mL, 4M in dioxane, 0.8 mmol). The reaction mixture was stirred at ambient temperature for 15 hrs, then an additional amount of hydrogen chloride solution (0.6 mL, 4M in dioxane, 2.4 mmol) was added, and the reaction mixture was allowed to stir for another 9 hrs. All solvents were removed under reduced pressure to afford (S)-3-amino-9-(3-hydroxy-3-methylbut-1-yn-1-yl)-5-methyl-2,3-dihydropyrido[3,2-b][1,4]oxazepin-4 (5H)-one hydrochloride 28 (27 mg, 100%) as a pale yellow solid, which was directly used in the next step. MS (ESI, m/e) Calculated 275.1270; Found 276.1 [M+H]$^+$.

Synthesis of (S)—N-(9-(3-Hydroxy-3-methylbut-1-yn-1-yl)-5-methyl-4-oxo-2,3,4,5-tetra-hydropyrido [3,2-b][1,4]oxazepin-3-yl)-4-phenoxypicolinamide 29

To a solution of (S)-3-amino-9-(3-hydroxy-3-methylbut-1-yn-1-yl)-5-methyl-2,3-dihydropyrido[3,2-b][1,4] oxazepin-4 (5H)-one hydrochloride 28 (27 mg, 0.0858 mmol) and 4-phenoxypicolinic acid 13 (28 mg, 0.129 mmol) in anhydrous DMF (1.4 mL) was added diisopropylethylamine (55.5 mg, 74 μL, 0.429 mmol) followed by HATU (48.9 mg, 0.129 mmol). The resulting reaction mixture was stirred at ambient temperature for 14 hrs. A drop of water was added, and the solution was directly purified by reverse HPLC using a gradient of 40 to 80% acetonitrile in water buffered with 0.1% formic acid. The desired fractions were combined and lyophilized to afford (S)—N-(9-(3-hydroxy-3-methyl-but-1-yn-1-yl)-5-methyl-4-oxo-2,3,4,5-tetrahydropyrido[3, 2-b][1,4]oxazepin-3-yl)-4-phenoxypicolinamide 29 (22.1 mg, 55%) as a white solid. $^1$H NMR (400 MHz, CDCl$_3$) δ 8.96 (d, J=7.1 Hz, 1H), 8.46 (dd, J=5.6, 0.5 Hz, 1H), 8.23 (d, J=5.0 Hz, 1H), 7.62 (dd, J=2.6, 0.5 Hz, 1H), 7.48-7.38 (m, 2H), 7.31-7.22 (m, 1H), 7.19 (d, J=5.0 Hz, 1H), 7.12-7.06 (m, 2H), 6.97 (dd, J=5.6, 2.5 Hz, 1H), 5.03 (dt, J=11.3, 7.2 Hz, 1H), 4.89 (dd, J=9.6, 7.2 Hz, 1H), 4.39 (dd, J=11.3, 9.6 Hz, 1H), 3.52 (s, 3H), 1.63 (s, 6H). MS (ESI, m/e) Calculated 472.1747; Found 473.1 [M+H]$^+$.

General Procedure to Prepare 7-Substituted Pyridooxaazepine Compounds VIII Method A

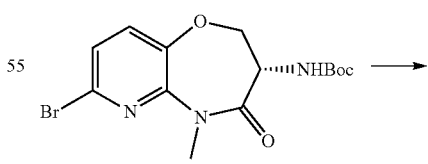

I

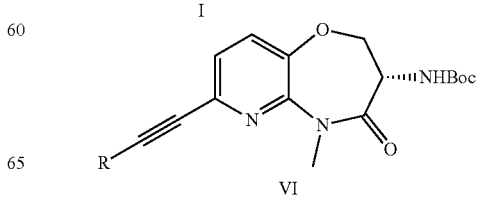

VI

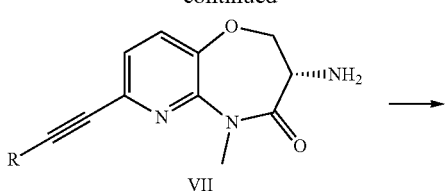

VII

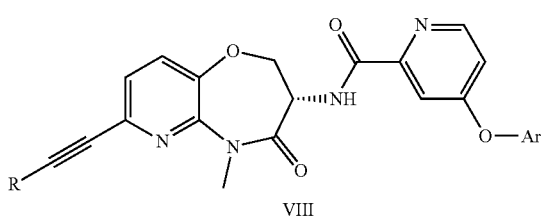

VIII 7-substituted pyridooxaazepine compounds were prepared according to the the Method A general procedure set forth above. Versatile intermediate I can be coupled with a variety of groups, via metal-catalyzed (for example palladium-catalyzed) cross coupling reactions as is known to those of skill in the art. In particular alkynyl groups can be readily coupled to the pyridooxezepine ring according to this general scheme by adapting the procedures set forth below. By way of example, compounds made by method A include I-32, I-33, I-34, I-35, I-36, I-37, I-38, I-39, I-41, I-42, I-43, I-44, I-45, I-46 and I-47.

(S)—N-(7-(4,4-difluoro-3,3-dimethylbut-1-yn-1-yl)-5-methyl-4-oxo-2,3,4,5-tetrahydropyrido [3,2-b][1,4]oxazepin-3-yl)-4-phenoxypicolinamide (I-32)

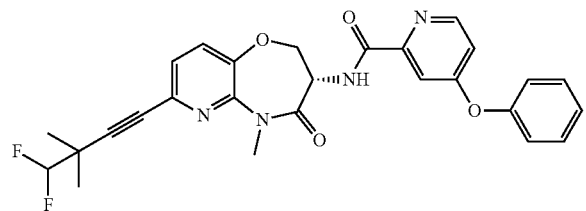 [SMILES: CN1C(=O)[C@@H](NC(=O)c2cc(Oc3ccccc3)ccn2)COc2ccc(C#CC(C)(C)C(F)F)nc21]

This compound was obtained from the corresponding aldehyde which was obtained by the oxidation of (S)—N-(7-(4-hydroxy-3,3-dimethylbut-1-yn-1-yl)-5-methyl-4-oxo-2,3,4,5-tetrahydro pyrido[3,2-b][1,4]oxazepin-3-yl)-4-phenoxypicolinamide. MS (ESI, m/z) Calculated 506.1766; Found [M+1]$^+$ 507.1. $^1$H NMR (400 MHz, Chloroform-d) δ (ppm) 8.93 (d, J=7.0 Hz, 1H), 8.45 (d, J=5.6 Hz, 1H), 7.61 (d, J=2.5 Hz, 1H), 7.49 (d, J=8.1 Hz, 1H), 7.46-7.38 (m, 2H), 7.36 (d, J=8.1 Hz, 1H), 7.28-7.23 (m, 1H), 7.10-7.05 (m, 2H), 6.96 (dd, J=5.6, 2.5 Hz, 1H), 5.25 (dd, J=48.3, 10.7 Hz, 1H), 5.02 (dt, J=11.4, 6.9 Hz, 1H), 4.79 (ddd, J=9.7, 6.8, 1.3 Hz, 1H), 4.37 (dd, J=11.4, 9.7 Hz, 1H), 3.53 (s, 3H), 1.62-1.59 (m, 3H), 1.55-1.51 (m, 3H).

N-((3S)-5-methyl-4-oxo-7-(4,4,4-trifluoro-3-hydroxybut-1-yn-1-yl)-2,3,4,5-tetrahydropyrido [3,2-b][1,4]oxazepin-3-yl)-4-phenoxypicolinamide (I-33)

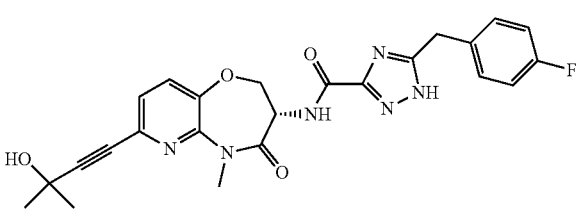 [SMILES: CN1C(=O)[C@@H](NC(=O)c2n[nH]c(Cc3ccc(F)cc3)n2)COc2ccc(C#CC(C)(C)O)nc21]

MS (ESI, m/z) Calculated 512.1308; Found [M+1]$^+$513.0. $^1$H NMR (400 MHz, Chloroform-d) δ (ppm) 9.03-8.89 (m, 1H), 8.45 (dt, J=5.7, 0.6 Hz, 1H), 7.61 (dt, J=2.6, 0.7 Hz, 1H), 7.52-7.46 (m, 1H), 7.46-7.38 (m, 2H), 7.35 (dd, J=8.1, 4.8 Hz, 1H), 7.28-7.24 (m, 1H), 7.10-7.04 (m, 2H), 6.96 (dd, J=5.6, 2.5 Hz, 1H), 5.18-4.99 (m, 1H), 4.94 (t, J=6.3 Hz, 1H), 4.81 (dt, J=9.7, 7.2 Hz, 1H), 4.43-4.31 (m, 1H), 3.54-3.46 (m, 3H), 3.23-2.86 (m, 1H).

(S)-5-(2-fluorobenzyl)-N-(7-(3-hydroxy-3-methylbut-1-yn-1-yl)-5-methyl-4-oxo-2,3,4,5-tetrahydropyrido[3,2-b][1,4]oxazepin-3-yl)-1H-1,2,4-triazole-3-carboxamide (I-34)

MS (ESI, m/z) Calculated 478.1765; Found [M+1]$^+$479.1. $^1$H NMR (400 MHz, Chloroform-d) δ (ppm) 12.18 (s, 1H), 8.10 (d, J=7.0 Hz, 1H), 7.44 (s, 1H), 7.27 (d, J=8.1 Hz, 1H), 7.26-7.18 (m, 2H), 7.10-6.97 (m, 2H), 5.01 (dt, J=11.4, 7.0 Hz, 1H), 4.75 (dd, J=9.8, 7.0 Hz, 1H), 4.32 (dd, J=11.4, 9.8 Hz, 1H), 4.20 (s, 2H), 3.50 (s, 3H), 1.64 (s, 6H).

(S)-5-(4-fluorobenzyl)-N-(7-(3-hydroxy-3-methylbut-1-yn-1-yl)-5-methyl-4-oxo-2,3,4,5-tetrahydropyrido[3,2-b][1,4]oxazepin-3-yl)-1H-1,2,4-triazole-3-carboxamide (I-35)

MS (ESI, m/z) Calculated 478.1765; Found [M+1]$^+$479.1.

(S)-5-benzyl-N-(7-((3,3-difluoro-1-hydroxycyclobutyl)ethynyl)-5-methyl-4-oxo-2,3,4,5-tetrahydropyrido[3,2-b][1,4]oxazepin-3-yl)-1H-1,2,4-triazole-3-carboxamide (I-36)

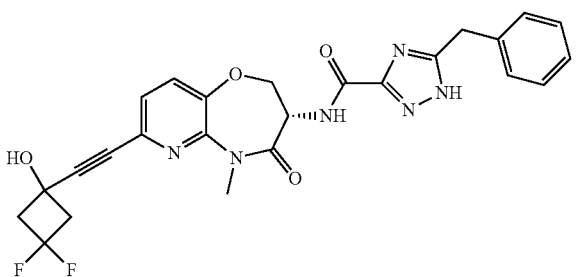 [SMILES: CN1C(=O)[C@@H](NC(=O)c2n[nH]c(Cc3ccccc3)n2)COc2ccc(C#CC3(O)CC(F)(F)C3)nc21]

MS (ESI, m/z) Calculated 508.1671; Found [M+1]⁺509.5. ¹H NMR (400 MHz, Chloroform-d) δ (ppm) 12.33 (s, 1H), 8.11 (d, J=7.0 Hz, 1H), 7.42 (d, J=8.1 Hz, 1H), 7.31-7.17 (m, 6H), 5.02 (dt, J=11.3, 6.9 Hz, 1H), 4.73 (dd, J=9.8, 6.9 Hz, 1H), 4.33 (dd, J=11.4, 9.8 Hz, 1H), 4.14 (s, 2H), 3.51 (s, 1H), 3.46 (s, 3H), 3.27-3.11 (m, 2H), 2.99 (dtd, J=13.0, 11.7, 4.0 Hz, 2H).

5-Benzyl-N-((3S)-5-methyl-4-oxo-7-(4,4,4-trifluoro-3-hydroxybut-1-yn-1-yl)-2,3,4,5-tetrahydropyrido[3,2-b][1,4]oxazepin-3-yl)-1H-1,2,4-triazole-3-carboxamide (I-37)

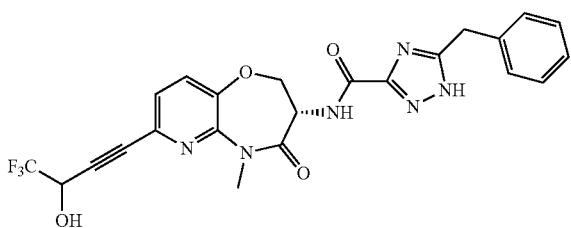 [SMILES: CN1C(=O)[C@@H](NC(=O)c2n[nH]c(Cc3ccccc3)n2)COc2ccc(C#CC(O)C(F)(F)F)nc21]

MS (ESI, m/z) Calculated 500.1420; Found [M+1]⁺501.5. ¹H NMR (400 MHz, Chloroform-d) δ (ppm) 9.20 (s, 0.5H), 8.11 (dd, J=6.9, 3.2 Hz, 1H), 7.47 (dd, J=8.1, 1.2 Hz, 1H), 7.36-7.29 (m, 3H), 7.28 (d, J=4.0 Hz, 2H), 6.27 (q, J=5.7 Hz, 0.5H), 5.13-4.89 (m, 2H), 4.78 (ddd, J=9.8, 6.8, 3.0 Hz, 1H), 4.35 (ddd, J=11.3, 9.9, 1.2 Hz, 1H), 4.16 (s, 2H), 3.48 (m, 3H).

(S)-4-Fluoro-1-(4-fluorobenzyl)-N-(7-(3-hydroxy-3-methylbut-1-yn-1-yl)-5-methyl-4-oxo-2,3,4,5-tetrahydropyrido[3,2-b][1,4]oxazepin-3-yl)-1H-pyrazole-3-carboxamide (I-38)

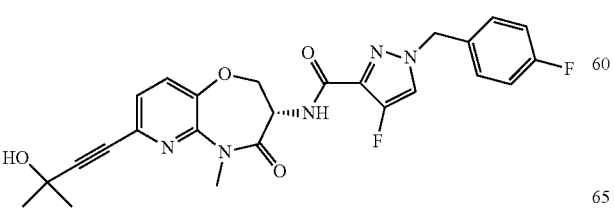

MS (ESI, m/z) Calculated 495.1718; Found [M+1]⁺496.5. ¹H NMR (400 MHz, Chloroform-d) δ (ppm) 7.64 (d, J=6.4 Hz, 1H), 7.43 (d, J=8.1 Hz, 1H), 7.25-7.16 (m, 4H), 7.07-6.98 (m, 2H), 5.17 (s, 2H), 5.00 (dt, J=11.3, 6.7 Hz, 1H), 4.82 (dd, J=9.7, 6.9 Hz, 1H), 4.28 (dd, J=11.3, 9.7 Hz, 1H), 3.49 (s, 3H), 1.62 (s, 6H).

(S)—N-(7-ethynyl-5-methyl-4-oxo-2,3,4,5-tetrahydropyrido[3,2-b][1,4]oxazepin-3-yl)-4-(3-fluorophenoxy)picolinamide (I-39)

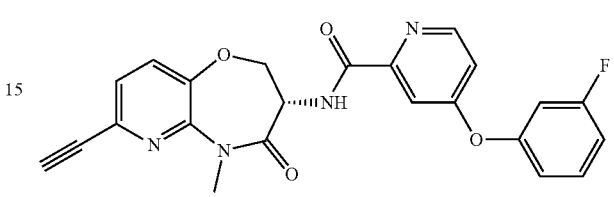

This compound was obtained from the desilyation of (S)-4-(3-fluorophenoxy)-N-(5-methyl-4-oxo-7-((trimethylsilyl)ethynyl)-2,3,4,5-tetrahydropyrido[3,2-b][1,4]oxazepin-3-yl)picolinamide. MS (ESI, m/z) Calculated 432.1234; Found [M+1]⁺433.1. ¹H NMR (400 MHz, Chloroform-d) δ (ppm) 8.94 (d, J=7.0 Hz, 1H), 8.49 (dd, J=5.6, 0.5 Hz, 1H), 7.63 (dd, J=2.5, 0.5 Hz, 1H), 7.49 (d, J=8.1 Hz, 1H), 7.42-7.32 (m, 2H), 7.02-6.94 (m, 2H), 6.88 (ddt, J=8.1, 2.2, 0.8 Hz, 1H), 6.82 (dt, J=9.3, 2.3 Hz, 1H), 5.03 (dt, J=11.4, 6.9 Hz, 1H), 4.79 (dd, J=9.7, 6.9 Hz, 1H), 4.38 (dd, J=11.4, 9.7 Hz, 1H), 3.54 (s, 3H), 3.17 (s, 1H).

(S)-4-fluoro-1-(4-fluorobenzyl)-N-(5-methyl-4-oxo-7-(prop-1-yn-1-yl)-2,3,4,5-tetrahydropyrido[3,2-b][1,4]oxazepin-3-yl)-1H-pyrazole-3-carboxamide (I-41)

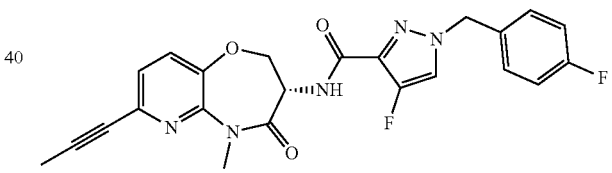

MS (ESI, m/z) Calculated 451.1456; Found [M+1]⁺452.1. ¹H NMR (400 MHz, Chloroform-d) δ (ppm) 7.66 (d, J=6.4 Hz, 1H), 7.43 (d, J=8.1 Hz, 1H), 7.24 (d, J=1.2 Hz, 1H), 7.21 (td, J=4.3, 1.4 Hz, 3H), 7.09-6.97 (m, 2H), 5.19 (s, 2H), 5.01 (dt, J=11.2, 6.7 Hz, 1H), 4.83 (dd, J=9.7, 7.0 Hz, 1H), 4.29 (dd, J=11.3, 9.7 Hz, 1H), 3.51 (s, 3H), 2.08 (s, 3H).

(S)-4-fluoro-1-((6-fluoropyridin-2-yl)methyl)-N-(5-methyl-4-oxo-7-(prop-1-yn-1-yl)-2,3,4,5-tetrahydropyrido[3,2-b][1,4]oxazepin-3-yl)-1H-pyrazole-3-carboxamide (I-42)

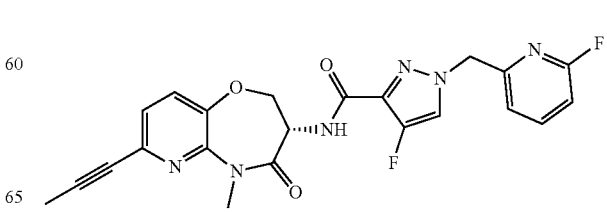

MS (ESI, m/z) Calculated 452.1408; Found [M+1]⁺453.1. ¹H NMR (400 MHz, Chloroform-d) δ (ppm) 7.85-7.75 (m, 1H), 7.65 (d, J=6.4 Hz, 1H), 7.50 (d, J=4.7 Hz, 1H), 7.44 (d, J=8.1 Hz, 1H), 7.24 (d, J=8.1 Hz, 1H), 7.06-7.00 (m, 1H), 6.94-6.88 (m, 1H), 5.28 (s, 2H), 5.02 (dt, J=11.2, 6.7 Hz, 1H), 4.83 (dd, J=9.7, 6.9 Hz, 1H), 4.29 (dd, J=11.2, 9.7 Hz, 1H), 3.52 (s, 3H), 2.09 (s, 3H).

N-((3S)-5-methyl-4-oxo-7-(4,4,4-trifluoro-3-hydroxy-3-methylbut-1-yn-1-yl)-2,3,4,5-tetrahydro pyrido[3,2-b][1,4]oxazepin-3-yl)-4-phenoxypicolinamide (I-43)

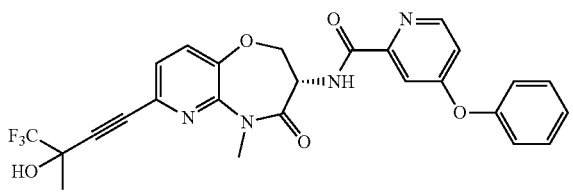 [SMILES: CN1C(=O)[C@@H](NC(=O)c2cc(Oc3ccccc3)ccn2)COc2ccc(C#CC(C)(O)C(F)(F)F)nc21]

MS (ESI, m/z) Calculated 526.1464; Found [M+1]⁺527.3. ¹H NMR (400 MHz, Chloroform-d) δ (ppm) 9.01 (dd, J=23.0, 6.7 Hz, 1H), 8.44 (dt, J=5.6, 0.7 Hz, 1H), 7.62 (ddd, J=3.3, 2.5, 0.5 Hz, 1H), 7.47 (d, J=8.1 Hz, 1H), 7.45-7.38 (m, 2H), 7.30-7.26 (m, 1H), 7.25-7.21 (m, 1H), 7.07 (dq, J=7.3, 1.0 Hz, 2H), 6.94 (ddd, J=5.6, 2.5, 1.5 Hz, 1H), 5.19 (ddt, J=51.2, 11.3, 6.7 Hz, 1H), 4.85 (ddd, J=19.7, 9.7, 6.7 Hz, 1H), 4.35 (ddd, J=11.5, 9.7, 1.8 Hz, 1H), 3.49-3.37 (m, 3H), 1.80-1.72 (m, 3H).

(S)—N-(5-methyl-7-(oxetan-3-ylethynyl)-4-oxo-2,3,4,5-tetrahydropyrido[3,2-b][1,4]oxazepin-3-yl)-4-phenoxypicolinamide (I-44)

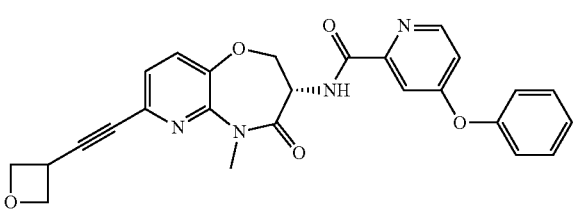 [SMILES: CN1C(=O)[C@@H](NC(=O)c2cc(Oc3ccccc3)ccn2)COc2ccc(C#CC3COC3)nc21]

MS (ESI, m/z) Calculated 470.1590; Found [M+1]⁺471.1. ¹H NMR (400 MHz, Chloroform-d) δ (ppm) 8.92 (d, J=7.0 Hz, 1H), 8.44 (dd, J=5.6, 0.5 Hz, 1H), 7.61 (dd, J=2.5, 0.5 Hz, 1H), 7.46 (d, J=8.1 Hz, 1H), 7.44-7.37 (m, 2H), 7.28 (d, J=8.1 Hz, 1H), 7.26-7.22 (m, 1H), 7.09-7.04 (m, 2H), 6.95 (dd, J=5.6, 2.6 Hz, 1H), 5.01 (dt, J=11.4, 7.0 Hz, 1H), 4.86 (dq, J=7.4, 5.6 Hz, 4H), 4.78 (dd, J=9.7, 6.9 Hz, 1H), 4.34 (dd, J=11.4, 9.7 Hz, 1H), 4.11 (tt, J=8.5, 7.4 Hz, 1H), 3.52 (s, 3H).

(S)—N-(7-(3,3-difluoro-3-(oxetan-3-yl)prop-1-yn-1-yl)-5-methyl-4-oxo-2,3,4,5-tetrahydropyrido [3,2-b][1,4]oxazepin-3-yl)-4-phenoxypicolinamide (I-45)

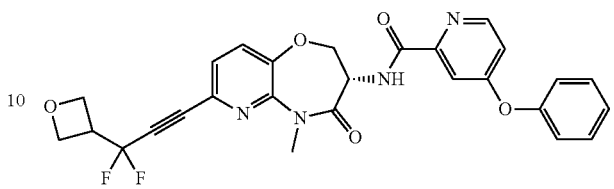

MS (ESI, m/z) Calculated 520.1558; Found [M+1]⁺521.1. ¹H NMR (400 MHz, Chloroform-d) δ (ppm) 8.92 (d, J=6.9 Hz, 1H), 8.45 (d, J=5.6 Hz, 1H), 7.62 (d, J=2.5 Hz, 1H), 7.51 (d, J=8.1 Hz, 1H), 7.46-7.37 (m, 3H), 7.29-7.23 (m, 1H), 7.11-7.04 (m, 2H), 6.96 (dd, J=5.6, 2.5 Hz, 1H), 5.02 (dt, J=11.4, 6.8 Hz, 1H), 4.88-4.75 (m, 5H), 4.39 (dd, J=11.4, 9.8 Hz, 1H), 3.73 (dtdd, J=14.6, 12.5, 8.1, 6.5 Hz, 1H), 3.54 (s, 3H).

N-((3S)-7-(3-Amino-4,4,4-trifluoro-3-methylbut-1-yn-1-yl)-5-methyl-4-oxo-2,3,4,5-tetrahydro pyrido [3,2-b][1,4]oxazepin-3-yl)-4-phenoxypicolinamide (I-46)

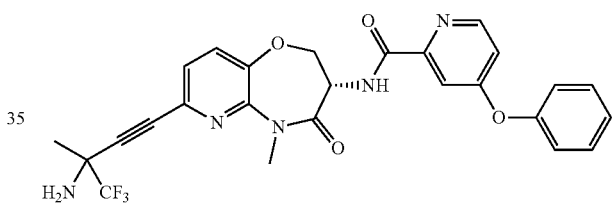

MS (ESI, m/z) Calculated 525.1624; Found [M+1]⁺526.0. ¹H NMR (400 MHz, Chloroform-d) δ (ppm) 8.91 (d, J=7.0 Hz, 1H), 8.44 (d, J=5.6 Hz, 1H), 7.61 (d, J=2.4 Hz, 1H), 7.50-7.37 (m, 3H), 7.31 (d, J=8.2 Hz, 1H), 7.27-7.21 (m, 1H), 7.10-7.03 (m, 2H), 6.95 (dd, J=5.6, 2.5 Hz, 1H), 5.00 (dt, J=11.4, 6.9 Hz, 1H), 4.78 (dd, J=9.7, 6.8 Hz, 1H), 4.35 (dd, J=11.4, 9.7 Hz, 1H), 3.52 (s, 3H), 1.92 (s, 2H), 1.66 (s, 3H).

(S)—N-(5-Methyl-4-oxo-7-((tetrahydro-2H-pyran-4-yl)ethynyl)-2,3,4,5-tetrahydropyrido[3,2-b][1,4]oxazepin-3-yl)-4-phenoxypicolinamide (I-47)

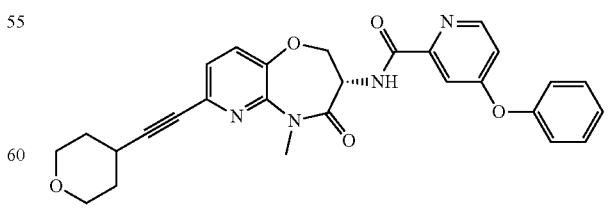

MS (ESI, m/z) Calculated 498.1903; Found [M+1]⁺499.1. ¹H NMR (400 MHz, Chloroform-d) δ (ppm) 8.92 (d, J=7.0 Hz, 1H), 8.44 (dd, J=5.6, 0.5 Hz, 1H), 7.61 (dd, J=2.5, 0.5 Hz, 1H), 7.47-7.37 (m, 3H), 7.29-7.22 (m, 2H), 7.10-7.03

(m, 2H), 6.95 (dd, J=5.6, 2.5 Hz, 1H), 5.01 (dt, J=11.3, 6.9 Hz, 1H), 4.78 (dd, J=9.7, 6.9 Hz, 1H), 4.33 (dd, J=11.4, 9.7 Hz, 1H), 3.96 (ddd, J=11.7, 5.3, 3.8 Hz, 2H), 3.59-3.49 (m, 5H), 2.88 (tt, J=8.7, 4.1 Hz, 1H), 1.98-1.87 (m, 2H), 1.81 (ddt, J=13.7, 9.2, 4.4 Hz, 2H).

Step 1: Synthesis of Intermediate (VI)

Intermediate I (0.1 mmol, 1 eq), substituted ethyne (0.2 to 0.3 mmol, 2 to 3 eq), Pd(PPh$_3$)$_4$ (0.01 mmol, 0.1 eq) and CuI (0.01 mmol, 0.1 eq) in anhydrous DMF (1 mL) in a vial was added Et$_3$N (0.4 mmol, 4 eq). The reaction solution was purged with nitrogen for 1 minute, then sealed and heated at 70° C. for 14 to 24 hours. Reaction solution was cooled to ambient temperature, diluted with ethyl acetate (100 mL), washed with brine, dried over anhydrous magnesium sulfate, filtered, and concentrated under the reduced pressure. Residue obtained was purified by silica gel chromatography or reverse HPLC (mobile phase A: water with 0.1% HCOOH; mobile phase B: acetonitrile with 0.1% HCOOH) to afford intermediate VI.

Step 2: Synthesis of Intermediate (VII)

Intermediate VI (1 eq) was dissolved in dichloromethane, then TFA (concentration: 10% in dichloromethane) or HCl (40 eq, 4N in dioxane) was added. The resulting solution was stirred at ambient temperature until all starting material disappeared (monitored by reverse HPLC). All solvents were removed under the reduced pressure to afford crude product of intermediate VII which was directly used in next step.

Step 3: Synthesis of Final Product (VIII)

Intermediate VII (1 eq), corresponding acid (1.2 eq), and diisopropylethylamine (5 eq) were dissolved in DMF (concentration 0.05M to 0.1M), then HATU (1.2 eq) was added. The resulting solution was stirred at ambient temperature for 14 to 24 hours. Reaction solution was added brine and ethyl acetate. Organic layer was separated and dried over anhydrous magnesium sulfate, filtered, and concentrated under the reduced pressure. Residue obtained was purified by silica gel chromatography or reverse HPLC (mobile phase A: water with 0.1% HCOOH; mobile phase B: acetonitrile with 0.1% HCOOH) to afford final product (VIII).

Exemplary 7-substituted pyridooxaazepine compounds also were prepared according to the general procedure Method B, set forth below.

Method B

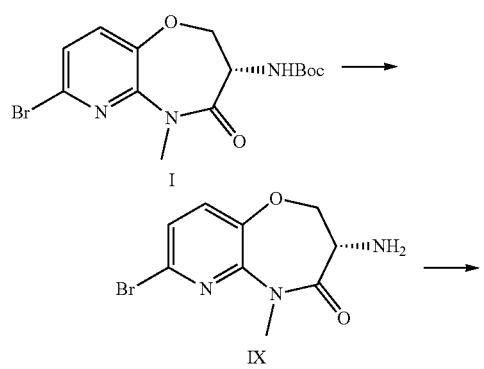

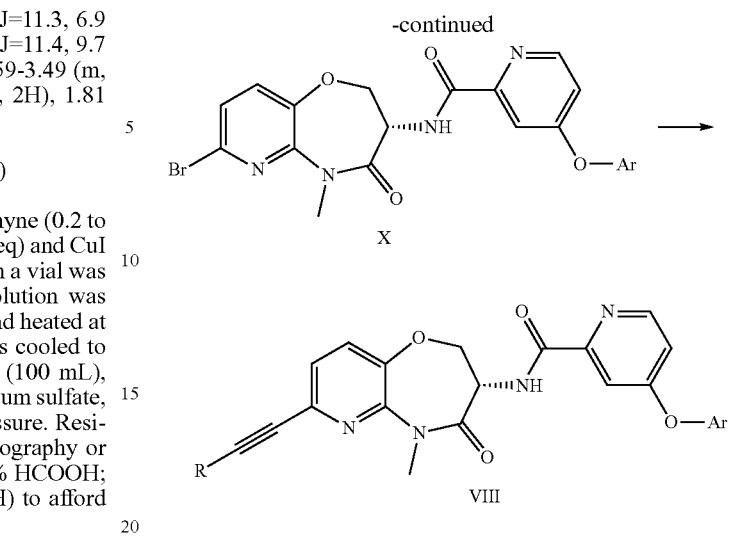

Step 1: Synthesis of Intermediate IX

Intermediate I was dissolved in 10% trifluoracetic acid in dichloromethane (0.1M) and stirred at room temperature for about 3 hours. All solvents were removed under the reduced pressure to afford crude trifluoracetic acid salt of IX, which was used directly in next step. MS (ESI, m/z) Calculated 270.9956; Found [M+1]$^+$271.9.

Step 2: Synthesis of Intermediate X

Intermediate IX (1 eq), corresponding acid (1.2 eq), and diisopropylethylamine (5 eq) were dissolved in DMF (concentration 0.05M to 0.1M), then HATU (1.2 eq) was added. The resulting solution was stirred at ambient temperature for 14 to 24 hours. Reaction solution was added brine and ethyl acetate. Organic layer was separated and dried over anhydrous magnesium sulfate, filtered, and concentrated under the reduced pressure. Residue obtained was purified by silica gel chromatography or reverse HPLC (mobile phase A: water with 0.1% HCOOH; mobile phase B: acetonitrile with 0.1% HCOOH) to afford intermediate(X).

Step 2: Synthesis of Final Product VIII

Intermediate X (0.1 mmol, 1 eq), substituted ethyne (0.2 to 0.3 mmol, 2 to 3 eq), Pd(PPh$_3$)$_4$ (0.01 mmol, 0.1 eq) and CuI (0.01 mmol, 0.1 eq) in anhydrous DMF (1 mL) in a vial was added Et$_3$N (0.4 mmol, 4 eq). The reaction solution was purged with nitrogen for 1 minute, then sealed and heated at 70° C. for 14 to 24 hours. Reaction solution was cooled to ambient temperature, diluted with ethyl acetate (100 mL), washed with brine, dried over anhydrous magnesium sulfate, filtered, and concentrated under the reduced pressure. Residue obtained was purified by silica gel chromatography or reverse HPLC (mobile phase A: water with 0.1% HCOOH; mobile phase B: acetonitrile with 0.1% HCOOH) to afford final product VIII.

Compounds synthesized by method B include compounds I-17, I-19, I-20, I-21, I-22, I-23, I-24, I-25, I-26, I-27, I-28, I-29, I-30 and I-40.

((S)—N-(7-((3-hydroxyoxetan-3-yl)ethynyl)-5-methyl-4-oxo-2,3,4,5-tetrahydropyrido[3,2b][1,4]oxazepin-3-yl)-4-phenoxypicolinamide (I-17)

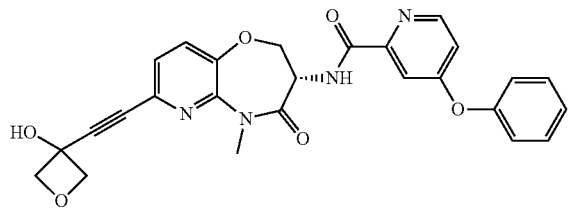 [SMILES: CN1C(=O)[C@@H](NC(=O)c2cc(Oc3ccccc3)ccn2)COc2ccc(C#CC3(O)COC3)nc21]

MS (ESI, m/z) Calculated 486.1539; Found [M+1]⁺487.1.

(S)-4-(4-fluorophenoxy)-N-(7-((3-hydroxyoxetan-3-yl)ethynyl)-5-methyl-4-oxo-2,3,4,5-tetrahydropyrido[3,2-b][1,4]oxazepin-3-yl)picolinamide (I-19)

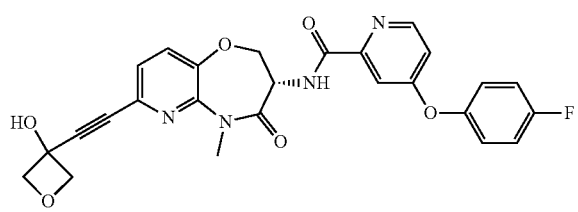 [SMILES: CN1C(=O)[C@@H](NC(=O)c2cc(Oc3ccc(F)cc3)ccn2)COc2ccc(C#CC3(O)COC3)nc21]

MS (ESI, m/z) Calculated 504.1445; Found [M+1]⁺505.1.

(S)—N-(7-((3-fluorooxetan-3-yl)ethynyl)-5-methyl-4-oxo-2,3,4,5-tetrahydro pyrido [3,2,b][1,4]oxazepin-3-yl)-4-phenoxypicolinamide (I-20)

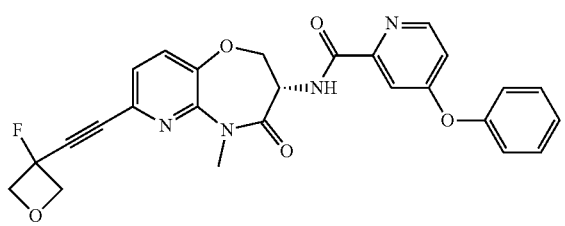 [SMILES: CN1C(=O)[C@@H](NC(=O)c2cc(Oc3ccccc3)ccn2)COc2ccc(C#CC3(F)COC3)nc21]

To a solution of ((S)—N-(7-((3-hydroxyoxetan-3-yl)ethynyl)-5-methyl-4-oxo-2,3,4,5-tetrahydro pyrido[3,2b][1,4]oxazepin-3-yl)-4-phenoxypicolinamide (9.5 mg, 0.0195 mmol) in anhydrous dichloromethane (1 mL) at −78° C. was added Deoxo-Fluor (8.6 mg, 7.2 uL, 0.039 mmol). The resulting solution was stirred at this temperature for 30 minutes, then additional Deoxo-Fluor (4.3 mg, 3.6 uL, 0.020 mmol) was added and stirred for additional 15 minutes. Saturated sodium bicarbonate solution (0.1 mL) was added followed by dichloromethane (60 mL). Solution was washed with water (15 mL), brine (15 mL) and dried over anhydrous magnesium sulfate, filtered and concentrated under the reduced pressure. Residue was purified by reverse HPLC (40 to 70% acetonitrile in water with 0.1% formic acid). Desired fractions were combined, diluted with ethyl acetate, washed with a little saturated sodium bicarbonate aqueous solution, brine, dried over anhydrous magnesium sulfate, filtered, and concentrated under the reduced pressure to afford (S)—N-(7-((3-fluorooxetan-3-yl)ethynyl)-5-methyl-4-oxo-2,3,4,5-tetrahydropyrido [3,2,b][1,4] oxazepin-3-yl)-4-phenoxypicolinamide (2.5 mg, 26%) as a white solid. MS (ESI, m/z) Calculated 488.1496; Found [M+1]⁺489.1. ¹H NMR (400 MHz, Chloroform-d) δ (ppm) 8.98-8.87 (m, 1H), 8.48-8.37 (m, 1H), 7.64-7.52 (m, 1H), 7.50 (d, J=8.1 Hz, 1H), 7.46-7.39 (m, 2H), 7.39-7.33 (m, 1H), 7.08 (dd, J=2.0, 1.3 Hz, 1H), 7.07 (dd, J=2.1, 1.0 Hz, 1H), 7.05-7.01 (m, 1H), 6.96 (dd, J=5.6, 2.6 Hz, 1H), 5.12-4.86 (m, 5H), 4.79 (dd, J=9.7, 6.8 Hz, 1H), 4.38 (dd, J=11.4, 9.7 Hz, 1H), 3.55 (m, 3H).

(S)-4-(3-fluorophenoxy)-N-(7-(3-hydroxy-3-methyl-but-1-yn-1-yl)-5-methyl-4-oxo-2,3,4,5-tetrahydropyrido[3,2-b][1,4]oxazepin-3-yl)picolinamide (I-21)

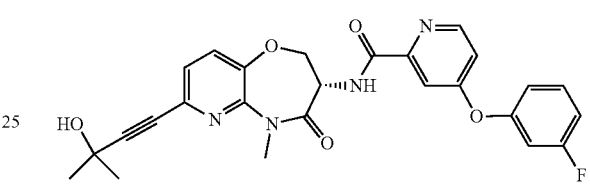

MS (ESI, m/z) Calculated 490.1652; Found [M+1]⁺491.1. ¹H NMR (400 MHz, Chloroform-d) δ (ppm) δ 8.93 (d, J=7.0 Hz, 1H), 8.48 (dd, J=5.6, 0.6 Hz, 1H), 7.62 (dd, J=2.5, 0.5 Hz, 1H), 7.38 (td, J=8.3, 6.5 Hz, 1H), 7.29 (s, 1H), 7.01-6.92 (m, 2H), 6.87 (ddt, J=8.2, 2.2, 0.8 Hz, 1H), 6.81 (dt, J=9.4, 2.4 Hz, 1H), 5.02 (dt, J=11.4, 7.0 Hz, 1H), 4.83-4.71 (m, 1H), 4.34 (dd, J=11.4, 9.7 Hz, 1H), 3.53 (s, 3H), 1.64 (s, 6H).

(S)-4-(3-fluorophenoxy)-N-(7-((3-hydroxyoxetan-3-yl)ethynyl)-5-methyl-4-oxo-2,3,4,5-tetrahydropyrido[3,2-b][1,4]oxazepin-3-yl)picolinamide (I-22)

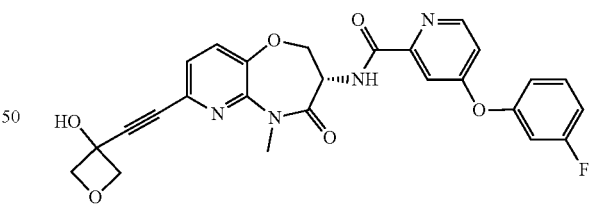

MS (ESI, m/z) Calculated 504.1445; Found [M+1]⁺505.1. ¹H NMR (400 MHz, Chloroform-d) δ (ppm) 9.01-8.86 (m, 1H), 8.53-8.41 (m, 1H), 7.65-7.54 (m, 1H), 7.53-7.46 (m, 1H), 7.38 (td, J=8.3, 6.5 Hz, 1H), 7.35-7.30 (m, 1H), 7.14-6.92 (m, 2H), 6.87 (ddt, J=8.2, 2.3, 0.8 Hz, 1H), 6.84-6.78 (m, 1H), 5.06 (dt, J=11.4, 6.9 Hz, 1H), 4.97 (td, J=6.2, 5.8, 0.9 Hz, 2H), 4.86-4.76 (m, 3H), 4.71 (dt, J=6.9, 0.7 Hz, 1H), 4.37 (dd, J=11.4, 9.7 Hz, 1H), 3.54 (d, J=13.5 Hz, 3H).

(S)—N-(7-((3-fluorooxetan-3-yl)ethynyl)-5-methyl-4-oxo-2,3,4,5-tetrahydropyrido[3,2-b][1,4]oxazepin-3-yl)-4-(3-fluorophenoxy)picolinamide (I-23)

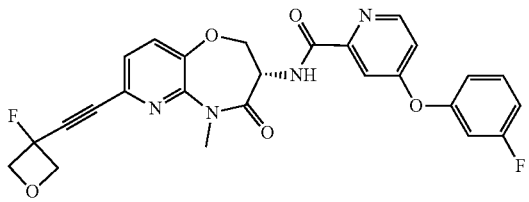 [SMILES: CN1C(=O)[C@@H](NC(=O)c2cc(Oc3cccc(F)c3)ccn2)COc2ccc(C#CC3(F)COC3)nc21]

To a solution of (S)-4-(3-fluorophenoxy)-N-(7-((3-hydroxyoxetan-3-yl)ethynyl)-5-methyl-4-oxo-2,3,4,5-tetrahydropyrido[3,2-b][1,4]oxazepin-3-yl)picolinamide (12.4 mg, 0.0246 mmol) in anhydrous dichloromethane (1 mL) at −78° C. was added Deoxo-Fluor (16.3 mg, 14 uL, 0.0737 mmol). The resulting solution was stirred at this temperature for 30 minutes, then saturated sodium bicarbonate solution (0.2 mL) was added followed by dichloromethane (80 mL). Solution was washed with water (15 mL), brine (15 mL) and dried over anhydrous magnesium sulfate, filtered, and concentrated under the reduced pressure. Residue was purified by reverse HPLC (40 to 70% acetonitrile in water with 0.1% formic acid). Desired fractions were combined, diluted with ethyl acetate, washed with a little saturated sodium bicarbonate aqueous solution, brine, dried over anhydrous magnesium sulfate, filtered, and concentrated under the reduced pressure to afford (S)—N-(7-((3-fluorooxetan-3-yl)ethynyl)-5-methyl-4-oxo-2,3,4,5-tetrahydropyrido[3,2-b][1,4]oxazepin-3-yl)-4-(3-fluorophenoxy)picolinamide (4.7 mg, 38%) as a white solid. MS (ESI, m/z) Calculated 506.1402; Found [M+1]⁺507.0. ¹H NMR (400 MHz, Chloroform-d) δ (ppm) 8.99-8.85 (m, 1H), 8.53-8.41 (m, 1H), 7.67-7.60 (m, 1H), 7.52 (d, J=8.1 Hz, 1H), 7.44-7.34 (m, 2H), 7.03-6.92 (m, 2H), 6.92-6.85 (m, 1H), 6.85-6.79 (m, 1H), 5.10-4.88 (m, 5H), 4.81 (dd, J=9.7, 6.8 Hz, 1H), 4.39 (dd, J=11.4, 9.7 Hz, 1H), 3.65-3.40 (m, 3H).

(S)-5-benzyl-N-(7-(3-hydroxy-3-methylbut-1-yn-1-yl)-5-methyl-4-oxo-2,3,4,5-tetrahydropyrido [3,2-b][1,4]oxazepin-3-yl)-1H-1,2,4-triazole-3-carboxamide (I-24)

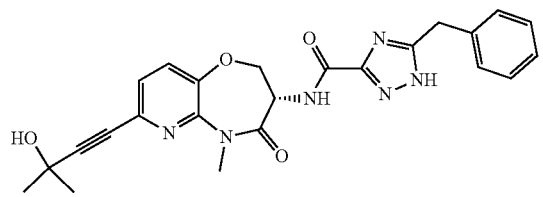 [SMILES: CN1C(=O)[C@@H](NC(=O)c2n[nH]c(Cc3ccccc3)n2)COc2ccc(C#CC(C)(C)O)nc21]

MS (ESI, m/z) Calculated 460.1859; Found [M+1]⁺461.1. ¹H NMR (400 MHz, Methanol-d4) δ (ppm) 7.61 (d, J=8.2 Hz, 1H), 7.36 (d, J=8.1 Hz, 1H), 7.35-7.15 (m, 5H), 5.03 (dd, J=11.5, 7.1 Hz, 1H), 4.67 (dd, J=9.8, 7.1 Hz, 1H), 4.51 (dd, J=11.6, 9.8 Hz, 1H), 4.17 (s, 2H), 3.45 (s, 3H), 1.58 (s, 6H).

(S)-5-benzyl-N-(7-((3-hydroxyoxetan-3-yl)ethynyl)-5-methyl-4-oxo-2,3,4,5-tetrahydropyrido [3,2-b][1,4]oxazepin-3-yl)-1H-1,2,4-triazole-3-carboxamide (I-25)

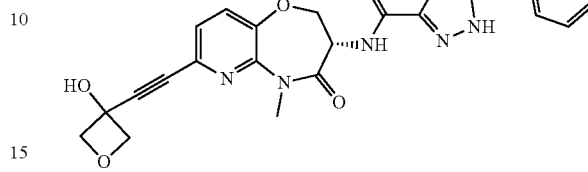

MS (ESI, m/z) Calculated 474.1652; Found [M+1]⁺475.1. ¹H NMR (400 MHz, Methanol-d4) δ (ppm) 7.64 (d, J=8.2 Hz, 1H), 7.44 (d, J=8.1 Hz, 1H), 7.36-7.20 (m, 5H), 5.04 (dd, J=11.5, 7.0 Hz, 1H), 4.89 (d, J=0.9 Hz, 2H), 4.73-4.69 (m, 2H), 4.67 (dd, J=7.2, 2.7 Hz, 1H), 4.52 (dd, J=11.6, 9.8 Hz, 1H), 4.16 (s, 2H), 3.46 (s, 3H).

(S)—N-(7-((1-hydroxycyclobutyl)ethynyl)-5-methyl-4-oxo-2,3,4,5-tetrahydropyrido[3,2-b][1,4]oxazepin-3-yl)-4-phenoxypicolinamide (I-26)

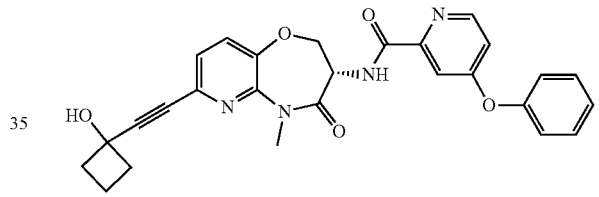

MS (ESI, m/z) Calculated 484.1747; Found [M+1]⁺485.1. ¹H NMR (400 MHz, Chloroform-d) δ (ppm) 8.93 (d, J=7.0 Hz, 1H), 8.44 (d, J=5.6 Hz, 1H), 7.61 (d, J=2.5 Hz, 1H), 7.50-7.37 (m, 3H), 7.30 (d, J=8.1 Hz, 1H), 7.27-7.23 (m, 1H), 7.11-7.03 (m, 2H), 6.95 (dd, J=5.6, 2.5 Hz, 1H), 5.03 (dt, J=11.4, 6.9 Hz, 1H), 4.79 (dd, J=9.7, 7.0 Hz, 1H), 4.35 (dd, J=11.4, 9.7 Hz, 1H), 3.52 (s, 3H), 2.65-2.52 (m, 2H), 2.44 (s, 1H), 2.40-2.30 (m, 2H), 1.96-1.85 (m, 2H).

(S)-4-(4-fluorophenoxy)-N-(7-(3-hydroxy-3-methylbut-1-yn-1-yl)-5-methyl-4-oxo-2,3,4,5-tetrahydropyrido[3,2-b][1,4]oxazepin-3-yl)picolinamide (I-27)

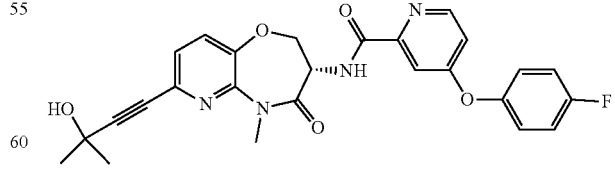

MS (ESI, m/z) Calculated 490.1652; Found [M+1]⁺491.1. ¹H NMR (400 MHz, Chloroform-d) δ (ppm) 8.92 (d, J=7.0 Hz, 1H), 8.45 (dd, J=5.6, 0.6 Hz, 1H), 7.57 (dd, J=2.6, 0.5 Hz, 1H), 7.45 (d, J=8.1 Hz, 1H), 7.28 (d, J=8.1 Hz, 1H), 7.14-7.08 (m, 2H), 7.08-7.02 (m, 2H), 6.93 (dd, J=5.6, 2.6

Hz, 1H), 5.01 (dt, J=11.3, 7.0 Hz, 1H), 4.82-4.72 (m, 1H), 4.34 (dd, J=11.4, 9.7 Hz, 1H), 3.52 (d, J=1.3 Hz, 3H).

(S)-4-(2-fluorophenoxy)-N-(7-(3-hydroxy-3-methyl-but-1-yn-1-yl)-5-methyl-4-oxo-2,3,4,5-tetrahydropyrido[3,2-b][1,4]oxazepin-3-yl)picolinamide (I-28)

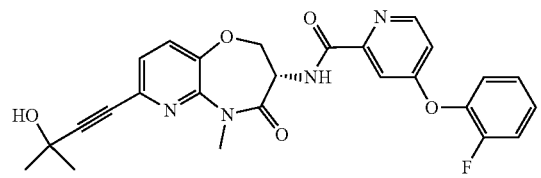 [SMILES: CN1C(=O)[C@@H](NC(=O)c2cc(Oc3ccccc3F)ccn2)COc2ccc(C#CC(C)(C)O)nc21]

MS (ESI, m/z) Calculated 490.1652; Found [M+1]⁺491.1. ¹H NMR (400 MHz, Chloroform-d) δ (ppm) 8.95 (d, J=7.0 Hz, 1H), 8.48 (dd, J=5.6, 0.5 Hz, 1H), 7.59 (dt, J=2.6, 0.6 Hz, 1H), 7.47 (d, J=8.1 Hz, 1H), 7.30-7.23 (m, 4H), 7.23-7.21 (m, 1H), 7.21-7.17 (m, 2H), 6.98 (ddd, J=5.6, 2.6, 0.5 Hz, 1H), 5.03 (dt, J=11.4, 6.9 Hz, 1H), 4.79 (dd, J=9.7, 6.9 Hz, 1H), 4.35 (dd, J=11.4, 9.7 Hz, 1H), 4.13 (q, J=7.1 Hz, 1H), 3.53 (s, 3H), 1.65 (s, 6H).

(S)—N-(7-ethynyl-5-methyl-4-oxo-2,3,4,5-tetrahydropyrido[3,2-b][1,4]oxazepin-3-yl)-4-fluoro-1-(4-fluorobenzyl)-1H-pyrazole-3-carboxamide (I-40)

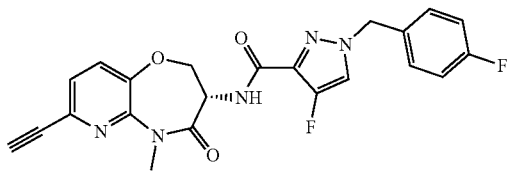 [SMILES: C#Cc1ccc2c(n1)N(C)C(=O)[C@@H](NC(=O)c1nn(Cc3ccc(F)cc3)cc1F)CO2]

This compound was obtained from the desilylation of (S)-4-fluoro-1-(4-fluorobenzyl)-N-(5-methyl-4-oxo-7-((trimethylsilyl)ethynyl)-2,3,4,5-tetrahydropyrido[3,2-b][1,4]oxazepin-3-yl)-1H-pyrazole-3-carboxamide. MS (ESI, m/z) Calculated 437.1299; Found [M+1]⁺438.1. ¹H NMR (400 MHz, Chloroform-d) δ (ppm) 7.66 (d, J=6.4 Hz, 1H), 7.48 (d, J=8.1 Hz, 1H), 7.35 (d, J=8.1 Hz, 1H), 7.25-7.18 (m, 3H), 7.11-7.01 (m, 2H), 5.19 (s, 2H), 5.03 (dt, J=11.3, 6.7 Hz, 1H), 4.84 (dd, J=9.7, 6.8 Hz, 1H), 4.32 (dd, J=11.3, 9.7 Hz, 1H), 3.53 (s, 3H), 3.16 (s, 1H).

General Synthesis of 7-Ethynyl Pyridoazepine Compound XI

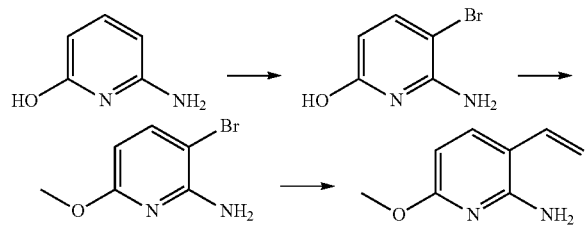

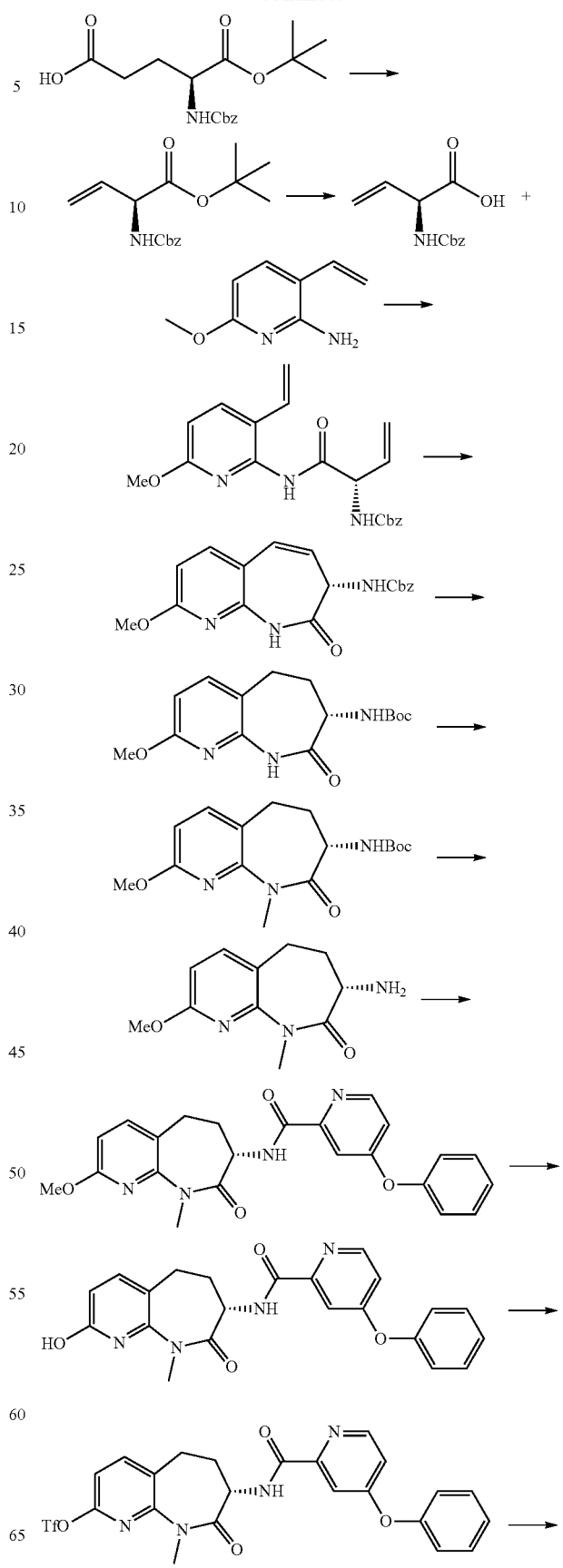

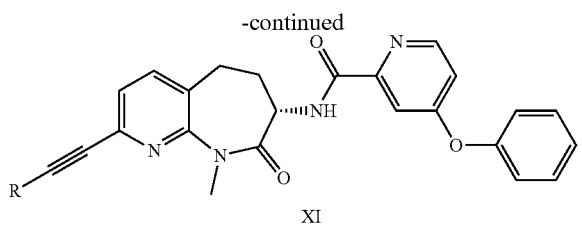

XI

As will be readily appreciated by those of skill in the art, the synthesis of compound XI illustrated is applicable to compounds having a variety of R groups.

6-Amino-5-bromopyridin-2-ol

6-Aminopyridin-2-ol (11 g, 0.1 mmol) was dissolved in acetic acid (220 mL), then bromine (16 g, 5.12 mL, 0.1 mmol) was added at ambient temperature. The resulting solution was stirred at this temperature for 40 minutes. Water (200 mL) was added, and solution was filtered through Celite. Filtrate was extracted with ethyl acetate (3×400 mL). Combined organic layer was washed with water (2×100 mL), dried over anhydrous magnesium sulfate, filtered, and concentrated under the reduced pressure to afford crude product of 6-Amino-5-bromopyridin-2-ol (8.3 g) as a pale brown solid, which was used directly in next step without further purification. MS (ESI, m/z) Calculated 187.9585; Found [M+1]$^+$188.9. $^1$H NMR (400 MHz, DMSO-d6) δ (ppm) 10.79 (s, 1H), 7.38 (d, J=8.8 Hz, 1H), 5.93 (s, 2H), 5.60 (d, J=8.8 Hz, 1H).

3-Bromo-6-methoxypyridin-2-amine

Crude material of 6-Amino-5-bromopyridin-2-ol (8.3 g, 43.9 mmol) was dissolved in acetone (130 mL), then potassium hydroxide (7.4 g, 0.132 mol) was added followed by dimethyl sulfate (7.20 g, 5.4 mL, 57.1 mmol). The reaction solution was stirred at ambient temperature for 4 hours. All solvents were removed under the reduced pressure. Residue was added brine (100 mL) and extracted with ethyl acetate (3×300 mL). Combined organic layer was dried over anhydrous magnesium sulfate, filtered, and concentrated under the reduced pressure. Residue obtained was purified by silica gel chromatography using a gradient of 0 to 30% ethyl acetate in hexane to afford 3-bromo-6-methoxypyridin-2-amine (4.09 g, 20% over 2 steps) as a white solid. MS (ESI, m/z) Calculated 201.9742; Found [M+1]$^+$202.9. $^1$H NMR (400 MHz, Chloroform-d) δ (ppm) 7.48 (d, J=8.4 Hz, 1H), 6.02 (d, J=8.3 Hz, 1H), 4.73 (s, 2H), 3.82 (s, 3H).

6-Methoxy-3-vinylpyridin-2-amine

Pd(PPh$_3$)$_4$ (1.17 g, 1.01 mmol) was added to the solution of 3-bromo-6-methoxypyridin-2-amine (4.09 g, 20.3 mmol) and tributyl(vinyl)stannane (9.64 g, 30.4 mmol) in anhydrous toluene (66 mL). The solution was purged with nitrogen for 1 min, then sealed and heated at 110° C. for 16 hours. Reaction solution was cooled to ambient temperature. Potassium fluoride aqueous solution (100 mL, 1M) was added followed by ethyl acetate (500 mL). The solution was filtered through Celite, washed with ethyl acetate. Organic was separated, washed with brine, dried over anhydrous magnesium sulfate, filtered, and concentrated under the reduced pressure. Residue obtained was purified by silica gel chromatography using a gradient of 0 to 10% ethyl acetate in hexane to afford 6-methoxy-3-vinylpyridin-2-amine (2.09 g, 69%) as a pale-yellow liquid. MS (ESI, m/z) Calculated 150.0793; Found [M+1]$^+$150.9. $^1$H NMR (400 MHz, Chloroform-d) δ (ppm) 7.46 (dd, J=8.2, 0.6 Hz, 1H), 6.57 (ddt, J=17.4, 11.1, 0.6 Hz, 1H), 6.14 (dd, J=8.2, 0.6 Hz, 1H), 5.49 (dd, J=17.4, 1.2 Hz, 1H), 5.21 (dd, J=11.1, 1.2 Hz, 1H), 4.45 (s, 2H), 3.85 (s, 3H).

tert-Butyl (S)-2-(((benzyloxy)carbonyl)amino)but-3-enoate

To a solution of (S)-4-(((benzyloxy)carbonyl)amino)-5-(tert-butoxy)-5-oxopentanoic acid (20 g, 59.3 mmol) in anhydrous benzene (600 mL) was added copper(II) acetate (2.7 g, 14.8 mmol). The resulting solution was stirred at ambient temperature under nitrogen for 2 hours, then lead tetraacetate (55.3 g, 0.119 mol) was added. The resulting solution was refluxed under nitrogen for 14 hours before it was cooled to ambient temperature. Reaction solution was filtered through Celite and washed with ethyl acetate (1200 mL). Organic layer was washed with water (2×300 mL), brine (300 mL), dried over anhydrous magnesium sulfate, filtered, and concentrated under the reduced pressure. Residue obtained was purified by silica gel chromatography using a gradient of 0 to 10% ethyl acetate in hexane to afford tert-butyl (S)-2-(((benzyloxy) carbonyl)amino)but-3-enoate (4.3 g, 25%) as a pale-yellow liquid. MS (ESI, m/z) Calculated 291.1471; Found [M-$^t$Bu+1]$^+$ 236.0. $^1$H NMR (400 MHz, Chloroform-d) δ (ppm) 7.44-7.27 (m, 5H), 5.90 (ddd, J=16.3, 10.4, 5.3 Hz, 1H), 5.44 (d, J=8.1 Hz, 1H), 5.34 (ddd, J=17.2, 1.8, 0.7 Hz, 1H), 5.24 (ddd, J=10.4, 1.8, 0.7 Hz, 1H), 5.12 (s, 2H), 4.86-4.74 (m, 1H), 1.46 (s, 9H).

(S)-2-(((Benzyloxy)carbonyl)amino)but-3-enoic acid

To a solution of tert-butyl (S)-2-(((benzyloxy)carbonyl) amino)but-3-enoate (4.3 g, 14.8 mmol) in anhydrous dichloromethane (340 mL) at 0° C. was added trifluoroacetic acid (50.5 g, 34 mL, 0.443 mol). The resulting solution was stirred at ambient temperature for 16 hours. All solvents were removed under the reduced pressure to afford (S)-2-(((benzyloxy)carbonyl)amino)but-3-enoic acid (3.3 g, 95%) as a white solid. MS (ESI, m/z) Calculated 235.0845; Found [M-1]$^+$ 234.1. $^1$H NMR (400 MHz, DMSO-d6) δ (ppm) δ 12.80 (s, 1H), 7.83 (d, J=8.2 Hz, 1H), 7.42-7.25 (m, 5H), 5.91 (ddd, J=16.8, 10.4, 6.1 Hz, 1H), 5.33 (dt, J=17.2, 1.5 Hz, 1H), 5.21 (dt, J=10.4, 1.4 Hz, 1H), 5.05 (s, 2H), 4.62 (ddt, J=7.8, 6.1, 1.7 Hz, 1H).

Benzyl (S)-(1-((6-methoxy-3-vinylpyridin-2-yl) amino)-1-oxobut-3-en-2-yl)carbamate To a cloudy solution of (S)-2-(((benzyloxy)carbonyl) amino)but-3-enoic acid (1.75 g, 7.55 mmol) in anhydrous dichloromethane (35 mL) at 0° C. was added 1-chloro-N, N,2-trimethylprop-1-en-1-amine (1.01 g, 1 mL, 7.55 g) dropwise, and stirred at this temperature for 30 minutes. Then 6-methoxy-3-vinylpyridin-2-amine (1.03 g, 6.87 mmol) in anhydrous dichloromethane (5 mL) was added dropwise followed by triethylamine (0.76 g, 1.05 mL, 7.55 mmol). The resulting solution was stirred at ambient temperature for additional 2 hours, and dichloromethane (150 mL) was added. The solution was washed with a little HCl aqueous solution (1N), sodium bicarbonate aqueous solution, brine, dried over anhydrous magnesium sulfate, filtered, and concentrated under the reduced pressure. Residue obtained was purified by silica gel chromatography using a gradient of 0 to 50% ethyl acetate in hexane to afford benzyl (S)-(1-((6-methoxy-3-vinylpyridin-2-yl)amino)-1-oxobut-3-en-2-yl)carbamate (568 mg, 23%) as a pale-yellow liquid. MS (ESI, m/z) Calculated 367.1532; Found [M+1]+368.1. $^1$H NMR (400 MHz, Chloroform-d) δ (ppm) 7.75 (d, J=8.5 Hz, 1H), 7.67 (s, 1H), 7.43-7.27 (m, 5H), 6.63 (d, J=8.5 Hz, 1H), 6.54 (dd, J=17.5, 11.1 Hz, 1H), 6.02 (ddd, J=16.9, 10.2, 6.3 Hz, 1H), 5.79 (s, 1H), 5.59 (dd, J=17.4, 0.9 Hz, 1H), 5.47 (d, J=17.0 Hz, 1H), 5.37 (d, J=10.1 Hz, 1H), 5.30 (d, J=11.0 Hz, 1H), 5.14 (d, J=1.3 Hz, 2H), 3.98-3.72 (s, 3H).

Benzyl (S)-(2-methoxy-8-oxo-8,9-dihydro-7H-pyrido[2,3-b]azepin-7-yl)carbamate

To a suspension solution of benzyl (S)-(1-((6-methoxy-3-vinylpyridin-2-yl)amino)-1-oxobut-3-en-2-yl)carbamate (573 mg, 1.56 mmol) in anhydrous toluene (78 mL) was added Grubb's $2^{nd}$ generation catalyst (133 mg, 0.156 mmol). The solution was purged with nitrogen for 1 minute, then heated at 80° C. under nitrogen for 15 hours. Reaction solution was cooled to ambient temperature. All solvents were removed under the reduced pressure. Residue obtained was purified by silica gel chromatography using a gradient of 0 to 30% ethyl acetate in hexane to afford benzyl (S)-(2-methoxy-8-oxo-8,9-dihydro-7H-pyrido[2,3-b]azepin-7-yl)carbamate (343 mg, 65%) as a white solid. MS (ESI, m/z) Calculated 339.1219; Found [M+1]+340.0. $^1$H NMR (400 MHz, Chloroform-d) δ (ppm) 7.97 (s, 1H), 7.55 (d, J=8.4 Hz, 1H), 7.44-7.27 (m, 5H), 6.63-6.53 (m, 2H), 6.22 (d, J=6.2 Hz, 1H), 5.67 (dd, J=10.0, 4.4 Hz, 1H), 5.14 (s, 2H), 4.41 (d, J=6.7 Hz, 1H), 3.91 (s, 3H).

tert-Butyl (S)-(2-methoxy-8-oxo-6,7,8,9-tetrahydro-5H-pyrido[2,3-b]azepin-7-yl)carbamate To a solution of benzyl (S)-(2-methoxy-8-oxo-8,9-dihydro-7H-pyrido[2,3-b]azepin-7-yl)carbamate (341 mg, 1 mmol) in MeOH were added 10% palladium on carbon (110 mg) and di-tert-butyl carbonate (537 mg, 2 mmol). The reaction was hydrogenated under 50 PSI hydrogen pressure in Parr-Shaker for 15 hours. Reaction solution was filtered through Celite and washed with MeOH. All solvents were removed under the reduced pressure. Residue obtained was purified by silica gel chromatography using a gradient of 0 to 40% ethyl acetate in hexane to afford tert-butyl (S)-(2-methoxy-8-oxo-6,7,8,9-tetrahydro-5H-pyrido[2,3-b]azepin-7-yl)carbamate (151 mg, 49%) as a white solid. MS (ESI, m/z) Calculated 307.1532; Found [M+1-Boc]+208.0. $^1$H NMR (400 MHz, Chloroform-d) δ (ppm) 7.82 (s, 1H), 7.41 (d, J=8.2 Hz, 1H), 6.50 (d, J=8.2 Hz, 1H), 5.53 (d, J=7.5 Hz, 1H), 4.29 (dt, J=11.5, 7.2 Hz, 1H), 3.85 (s, 3H), 2.87-2.73 (m, 1H), 2.73-2.55 (m, 2H), 2.02-1.89 (m, 1H), 1.39 (s, 9H).

tert-Butyl (S)-(2-methoxy-9-methyl-8-oxo-6,7,8,9-tetrahydro-5H-pyrido[2,3-b]azepin-7-yl) carbamate To a solution of tert-butyl (S)-(2-methoxy-8-oxo-6,7,8,9-tetrahydro-5H-pyrido[2,3-b]azepin-7-yl) carbamate (150 mg, 0.489 mmol) in anhydrous DMF (4 mL) was added methyl iodide (69.3 mg, 30.4 uL, 0.489 mmol) followed by cesium carbonate (159 mg, 0.489 mmol). The resulting solution was stirred at ambient temperature for 2 days. Reaction solution was diluted with ethyl acetate (150 mL), washed with water, brine, dried over anhydrous magnesium sulfate, filtered, and concentrated under the reduced pressure. Residue obtained was purified by silica gel chromatography using a gradient of 0 to 30% ethyl acetate in hexane to afford tert-butyl (S)-(2-methoxy-9-methyl-8-oxo-6,7,8,9-tetrahydro-5H-pyrido[2,3-b]azepin-7-yl) carbamate (147 mg, 94%) as a white solid. MS (ESI, m/z) Calculated 321.1689; Found [M+1-Boc]+222.0. $^1$H NMR (400 MHz, Chloroform-d) δ (ppm) 7.40 (d, J=8.1 Hz, 1H), 6.53 (d, J=8.2 Hz, 1H), 5.53 (d, J=7.7 Hz, 1H), 4.26 (dt, J=11.2, 7.4 Hz, 1H), 3.89 (s, 3H), 3.45 (s, 3H), 2.77-2.56 (m, 2H), 2.52 (dd, J=12.3, 6.4 Hz, 1H), 2.02-1.84 (m, 1H), 1.40 (s, 9H).

(S)-7-Amino-2-methoxy-9-methyl-5,6,7,9-tetrahydro-8H-pyrido[2,3-b]azepin-8-one

To a solution of tert-butyl (S)-(2-methoxy-9-methyl-8-oxo-6,7,8,9-tetrahydro-5H-pyrido[2,3-b]azepin-7-yl) carbamate (35 mg, 0.11 mmol) in anhydrous dichloromethane (1 mL) was added trifluoroacetic acid (0.1 mL). The resulting solution was stirred at ambient temperature for 3 hours.

Then anhydrous 1,2-dichloroethane (1 mL) was added. All solvents were removed under the reduced pressure to afford crude trifluoracetic acid salt of (S)-7-amino-2-methoxy-9-methyl-5,6,7,9-tetrahydro-8H-pyrido[2,3-b]azepin-8-one. Residue obtained was used directly in next step. MS (ESI, m/z) Calculated 221.1164; Found [M+1]$^+$222.1.

(S)—N-(2-Methoxy-9-methyl-8-oxo-6,7,8,9-tetrahydro-5H-pyrido[2,3-b]azepin-7-yl)-4-phenoxy picolinamide To a solution of crude trifluoracetic acid salt of (S)-7-amino-2-methoxy-9-methyl-5,6,7,9-tetrahydro-8H-pyrido [2,3-b]azepin-8-one (0.11 mmol) and 4-phenoxypicolinic acid (28 mg, 0.13 mmol) in anhydrous DMF (1 mL) was added diisopropylethylamine (56 mg, 75 uL, 0.43 mmol) followed by HATU (49.4 mg, 0.13 mmol). The resulting solution was stirred at ambient temperature for 19 hours. A drop of water was added to quench the reaction. The solution was directly purified by reverse HPLC (30 to 70% acetonitrile in water with 0.1% formic acid). Desired fractions were combined, diluted with ethyl acetate, washed with saturated sodium bicarbonate aqueous solution, brine, dried over anhydrous magnesium sulfate, filtered, and concentrated under the reduced pressure to afford (S)—N-(2-methoxy-9-methyl-8-oxo-6,7,8,9-tetrahydro-5H-pyrido[2,3-b]azepin-7-yl)-4-phenoxy picolinamide (43 mg, 95%) as a white solid. MS (ESI, m/z) Calculated 418.1641; Found [M+1]+419.1. $^1$H NMR (400 MHz, Chloroform-d) δ (ppm) 8.90 (d, J=7.6 Hz, 1H), 8.43 (dd, J=5.6, 0.5 Hz, 1H), 7.62 (dd, J=2.5, 0.5 Hz, 1H), 7.46 (d, J=8.2 Hz, 1H), 7.44-7.37 (m, 2H), 7.26-7.20 (m, 1H), 7.10-7.04 (m, 2H), 6.93 (dd, J=5.6, 2.6 Hz, 1H), 6.57 (d, J=8.2 Hz, 1H), 4.66 (dt, J=11.4, 7.5 Hz, 1H), 3.90 (s, 3H), 3.48 (s, 3H), 2.83-2.69 (m, 2H), 2.64-2.52 (m, 1H), 2.15-2.02 (m, 1H).

(S)—N-(2-Hydroxy-8-oxo-6,7,8,9-tetrahydro-5H-pyrido[2,3-b]azepin-7-yl)-4-phenoxy picolinamide To a solution of (S)—N-(2-methoxy-9-methyl-8-oxo-6,7,8,9-tetrahydro-5H-pyrido[2,3-b]azepin-7-yl)-4-phenoxy picolinamide (29 mg, 0.069 mmol) in anhydrous acetonitrile (1 mL) was added phosphorus tribromide (56 mg, 20 uL, 0.21 mmol). The resulting solution was heated at 80° C. for 3 hours. Reaction solution was cooled to ambient temperature and methanol was added carefully to quench the reaction. All solvents were removed under the reduced pressure. Crude solid was dissolved in DMSO and purified by reverse HPLC (20 to 56% acetonitrile in water with 0.1% formic acid). Desired fractions were combined and lyophilized to afford (S)—N-(2-hydroxy-8-oxo-6,7,8,9-tetrahydro-5H- pyrido[2,3-b]azepin-7-yl)-4-phenoxy picolinamide (24 mg, 87%) as a white solid. MS (ESI, m/z) Calculated 404.1485; Found [M+1]⁺405.1.

(S)-9-Methyl-8-oxo-7-(4-phenoxypicolinamido)-6,7,8,9-tetrahydro-5H-pyrido[2,3-b]azepin-2-yl trifluoromethanesulfonate To a solution of (S)—N-(2-hydroxy-8-oxo-6,7,8,9-tetrahydro-5H-pyrido[2,3-b]azepin-7-yl)-4-phenoxy picolinamide (24.2 mg, 0.06 mmol) and 1,1,1-trifluoro-N-phenyl-N-((trifluoromethyl) sulfonyl)methanesulfonamide (25.6 mg, 0.072 mmol) in anhydrous DMF (1 mL) was added anhydrous potassium carbonate (17.4 mg, 0.126 mmol). The resulting solution was stirred at ambient temperature for 20 hours. Reaction solution was diluted with ethyl acetate, washed with water, brine, dried over anhydrous magnesium sulfate, filtered, and concentrated under the reduced pressure. Residue obtained was purified by silica gel chromatography using a gradient of 0 to 50% ethyl acetate in hexane to afford (S)-9-methyl-8-oxo-7-(4-phenoxypicolinamido)-6,7,8,9-tetrahydro-5H-pyrido[2,3-b]azepin-2-yl trifluoromethanesulfonate (30 mg, 92%) as a white solid. MS (ESI, m/z) Calculated 536.0977; Found [M+1]⁺537.0.

General Procedure to Prepare 7-ethynyl pyridoazepine Compound XI (S)-9-methyl-8-oxo-7-(4-phenoxypicolinamido)-6,7,8,9-tetrahydro-5H-pyrido[2,3-b]azepin-2-yl trifluoromethanesulfonate (0.03 mmol, 1 eq), substituted ethyne (0.06 to 0.09 mmol, 2 to 3 eq), Pd(PPh₃)₄ (0.01 mmol, 0.1 eq) and CuI (0.01 mmol, 0.1 eq) in anhydrous DMF (0.5 mL) in a vial was added Et₃N (0.4 mmol, 4 eq). The reaction solution was purged with nitrogen for 1 minute, then sealed and heated at 70° C. for 14 to 24 hours. Reaction solution was cooled to ambient temperature, diluted with ethyl acetate (100 mL), washed with brine, dried over anhydrous magnesium sulfate, filtered, and concentrated under the reduced pressure. Residue obtained was purified by silica gel chromatography or reverse HPLC (mobile phase A: water with 0.1% HCOOH; mobile phase B: acetonitrile with 0.1% HCOOH) to afford intermediate final product XI. Compounds I-52, I-53, I-54, I-55, I-56, I-57, I-58, I-59 and I-60 are exemplary compounds synthesized by this general method. The picolinamide ring (the 'B' ring according to formulas presented herein) may be replaced with other heteroaryl groups in the general synthesis of XI presented above, as will be readily appreciated by those of skill in the art. For example, the picolinamide moiety may be replaced by another 5 or 6-membered heteroaryl ring described herein. By way of example of such a replacement, compound I-54 contains a triazole in the 'B' ring position. The general synthesis presented above was adapted according to the following working example.

Synthesis of (S)-5-benzyl-N-(2-(3-hydroxy-3-methylbut-1-yn-1-yl)-9-methyl-8-oxo-6,7,8,9-tetrahydro-5H-pyrido[2,3-b]azepin-7-yl)-1H-1,2,4-triazole-3-carboxamide (I-54)

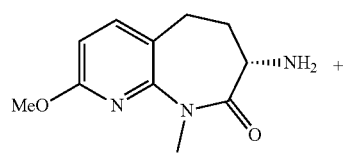

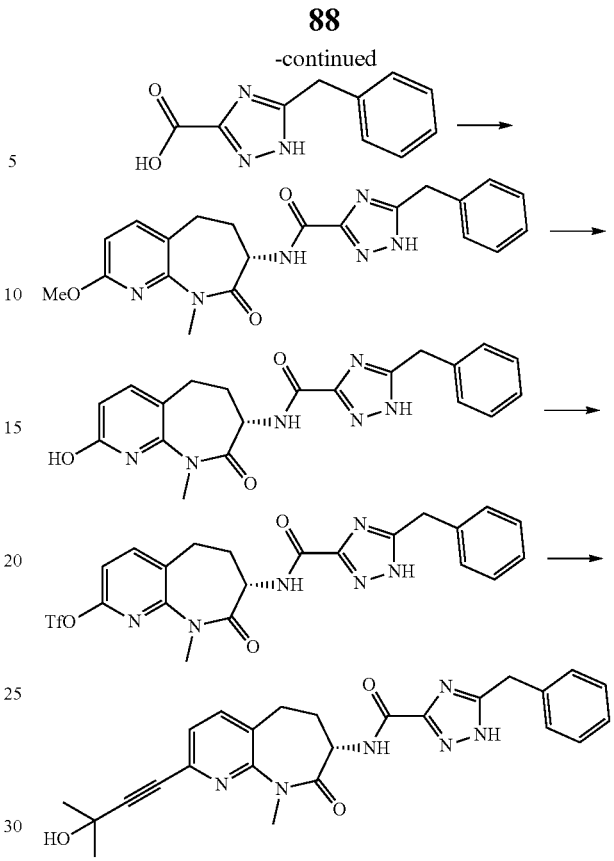

Step 1 (S)-5-Benzyl-N-(2-methoxy-9-methyl-8-oxo-6,7,8,9-tetrahydro-5H-pyrido[2,3-b]azepin-7-yl)-1H-1,2,4-triazole-3-carboxamide To a solution of crude trifluoracetic acid salt of (S)-7-amino-2-methoxy-9-methyl-5,6,7,9-tetrahydro-8H-pyrido[2,3-b]azepin-8-one (0.0523 mmol) and 5-benzyl-1H-1,2,4-triazole-3-carboxylic acid (10.6 mg, 0.0523 mmol) in anhydrous DMF (0.5 mL) was added diisopropylethylamine (27 mg, 37 uL, 0.209 mmol) followed by HATU (21.9 mg, 0.0575 mmol). The resulting solution was stirred at ambient temperature for 19 hours. A drop of water was added to quench the reaction. The solution was directly purified by reverse HPLC (15 to 52% acetonitrile in water with 0.1% formic acid). Desired fractions were combined, and lyophilized to afford (S)-5-benzyl-N-(2-methoxy-9-methyl-8-oxo-6,7,8,9-tetrahydro-5H-pyrido[2,3-b]azepin-7-yl)-1H-1,2,4-triazole-3-carboxamide (21 mg, 97%) as a white solid. MS (ESI, m/z) Calculated 406.1753; Found [M+1]⁺407.1.

Step 2 (S)-5-Benzyl-N-(2-hydroxy-9-methyl-8-oxo-6,7,8,9-tetrahydro-5H-pyrido[2,3-b]azepin-7-yl)-1H-1,2,4-triazole-3-carboxamide To a solution of (S)-5-benzyl-N-(2-methoxy-9-methyl-8-oxo-6,7,8,9-tetrahydro-5H-pyrido[2,3-b]azepin-7-yl)-1H-1,2,4-triazole-3-carboxamide (21 mg, 0.051 mmol) in anhydrous acetonitrile (1 mL) was added phosphorus tribromide (41 mg, 14 uL, 0.15 mmol). The resulting solution was heated at 80° C. for 3 hours. Reaction solution was cooled to ambient temperature and methanol was added carefully to quench the reaction. All solvents were removed under the reduced pressure. Crude solid was dissolved in DMSO and purified by reverse HPLC (10 to 40% acetonitrile in water with 0.1% formic acid). Desired fractions were combined and lyophilized to afford (S)-5-benzyl-N-(2-hydroxy-9-methyl-8-oxo-6,7,8,9-tetrahydro-5H-pyrido[2,3-b]azepin-7-yl)-1H-1,2,4-triazole-3-carboxamide (18 mg, 91%) as a white solid. MS (ESI, m/z) Calculated 392.1597; Found [M+1]$^+$ 393.1.

Step 3 (S)-7-(5-benzyl-1H-1,2,4-triazole-3-carboxamido)-9-methyl-8-oxo-6,7,8,9-tetrahydro-5H-pyrido[2,3-b]azepin-2-yl trifluoromethanesulfonate To a solution of (S)-5-benzyl-N-(2-hydroxy-9-methyl-8-oxo-6,7,8,9-tetrahydro-5H-pyrido[2,3-b]azepin-7-yl)-1H-1,2,4-triazole-3-carboxamide (18 mg, 0.046 mmol) and 1,1,1-trifluoro-N-phenyl-N-((trifluoromethyl) sulfonyl)methanesulfonamide (19.7 mg, 0.055 mmol) in anhydrous DMF (1 mL) was added anhydrous potassium carbonate (15.2 mg, 0.11 mmol). The resulting solution was stirred at ambient temperature for 2 hours. Reaction solution was diluted with ethyl acetate, washed with water, brine, dried over anhydrous magnesium sulfate, filtered, and concentrated under the reduced pressure. Residue obtained was purified by silica gel chromatography using a gradient of 0 to 50% acetone in hexane to afford (S)-7-(5-benzyl-1H-1,2,4-triazole-3-carboxamido)-9-methyl-8-oxo-6,7,8,9-tetrahydro-5H-pyrido[2,3-b]azepin-2-yl trifluoromethanesulfonate (22 mg, 92%) as a white solid. MS (ESI, m/z) Calculated 524.1090; Found [M+1]$^+$525.0.

Step 4 (S)-5-benzyl-N-(2-(3-hydroxy-3-methylbut-1-yn-1-yl)-9-methyl-8-oxo-6,7,8,9-tetrahydro-5H-pyrido[2,3-b]azepin-7-yl)-1H-1,2,4-triazole-3-carboxamide (S)-7-(5-Benzyl-1H-1,2,4-triazole-3-carboxamido)-9-methyl-8-oxo-6,7,8,9-tetrahydro-5H-pyrido[2,3-b]azepin-2-yl trifluoromethanesulfonate (22 mg, 0.0422 mmol), 2-methylbut-3-yn-2-ol (11.6 mg, 0.0138 mmol), Pd(PPh$_3$)$_4$ (5.3 mg, 0.0046 mmol) and CuI (0.9 mg, 0.0046 mmol) in anhydrous DMF (1 mL) in a vial was added Et$_3$N (18.6 mg, 26 uL, 0.184 mmol). The reaction solution was purged with nitrogen for 1 minute, then sealed and heated at 70° C. for 14 hours. Reaction solution was cooled to ambient temperature, diluted with ethyl acetate, washed with brine, dried over anhydrous magnesium sulfate, filtered, and concentrated under the reduced pressure. Residue obtained was purified by reverse HPLC (15% to 47% acetonitrile in water with 0.1% formic acid). Desired fractions were combined, diluted with ethyl acetate, washed with a little saturated sodium bicarbonate, brine, dried over anhydrous magnesium sulfate, filtered, and concentrated under the reduced pressure to afford (S)-5-benzyl-N-(2-(3-hydroxy-3-methylbut-1-yn-1-yl)-9-methyl-8-oxo-6,7,8,9-tetrahydro-5H-pyrido[2,3-b]azepin-7-yl)-1H-1,2,4-triazole-3-carboxamide (4.0 mg, 21%) as a white solid. MS (ESI, m/z) Calculated 458.2066; Found [M+1]$^+$459.1. $^1$H NMR (400 MHz, Chloroform-d) δ (ppm) 8.12 (d, J=7.2 Hz, 1H), 7.53 (d, J=7.7 Hz, 1H), 7.35-7.25 (m, 5H), 7.23 (d, J=7.7 Hz, 1H), 4.57 (dt, J=12.1, 6.9 Hz, 1H), 4.14 (s, 2H), 3.50 (s, 3H), 2.90-2.73 (m, 2H), 2.71-2.57 (m, 1H), 2.20 (s, 1H), 2.13-2.03 (m, 1H), 1.63 (s, 6H).

(S)—N-(2-(3-Hydroxy-3-methylbut-1-yn-1-yl)-9-methyl-8-oxo-6,7,8,9-tetrahydro-5H-pyrido[2,3-b]azepin-7-yl)-4-phenoxypicolinamide (I-52)

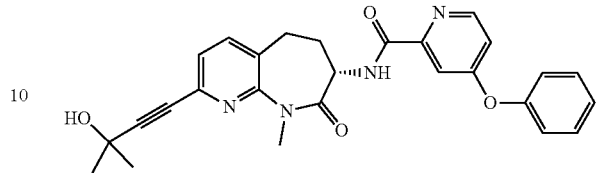

MS (ESI, m/z) Calculated 470.1954; Found [M+1]$^+$471.1. $^1$H NMR (400 MHz, Chloroform-d) δ (ppm) 8.93 (d, J=7.3 Hz, 1H), 8.43 (dd, J=5.6, 0.5 Hz, 1H), 7.62 (dd, J=2.6, 0.5 Hz, 1H), 7.55 (d, J=7.7 Hz, 1H), 7.45-7.36 (m, 2H), 7.26-7.21 (m, 2H), 7.11-7.03 (m, 2H), 6.93 (dd, J=5.6, 2.6 Hz, 1H), 4.59 (dt, J=11.1, 7.2 Hz, 1H), 3.52 (s, 3H), 2.93-2.73 (m, 2H), 2.73-2.58 (m, 1H), 2.14 (s, 1H), 2.13-1.99 (m, 1H), 1.65 (s, 6H).

(S)—N-(2-((3-Hydroxyoxetan-3-yl)ethynyl)-9-methyl-8-oxo-6,7,8,9-tetrahydro-5H-pyrido[2,3-b]azepin-7-yl)-4-phenoxypicolinamide (I-53)

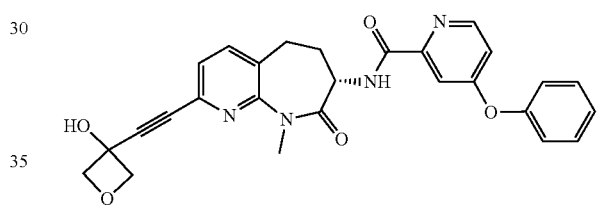

MS (ESI, m/z) Calculated 484.1747; Found [M+1]$^+$485.1. $^1$H NMR (400 MHz, Chloroform-d) δ (ppm) 8.94 (d, J=7.3 Hz, 1H), 8.44 (dd, J=5.6, 0.6 Hz, 1H), 7.62 (dd, J=2.6, 0.5 Hz, 1H), 7.59 (d, J=7.7 Hz, 1H), 7.45-7.37 (m, 2H), 7.30 (d, J=7.6 Hz, 1H), 7.26-7.20 (m, 1H), 7.11-7.04 (m, 2H), 6.93 (dd, J=5.6, 2.5 Hz, 1H), 4.98 (dd, J=6.6, 1.0 Hz, 2H), 4.80 (dt, J=6.8, 0.7 Hz, 2H), 4.61 (dt, J=11.1, 7.3 Hz, 1H), 3.52 (s, 3H), 2.89 (s, 1H), 2.88-2.75 (m, 2H), 2.75-2.62 (m, 1H), 2.18-2.04 (m, 1H).

N-((7S)-9-Methyl-8-oxo-2-(4,4,4-trifluoro-3-hydroxybut-1-yn-1-yl)-6,7,8,9-tetrahydro-5H-pyrido[2,3-b]azepin-7-yl)-4-phenoxypicolinamide (I-55)

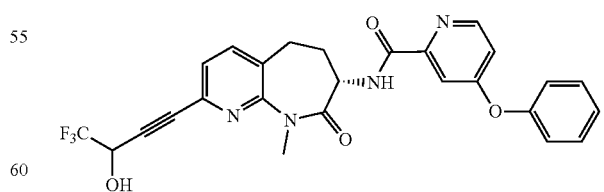

MS (ESI, m/z) Calculated 510.1515; Found [M+1]$^+$511.0. $^1$H NMR (400 MHz, Chloroform-d) δ (ppm) 9.01 (dd, J=20.7, 7.2 Hz, 1H), 8.42 (dd, J=5.6, 1.2 Hz, 1H), 7.63-7.53 (m, 2H), 7.45-7.35 (m, 2H), 7.31-7.25 (m, 1H), 7.24-7.18 (m, 1H), 7.09-7.00 (m, 2H), 6.92 (dd, J=5.6, 2.5 Hz, 1H), 4.91 (d, J=6.4 Hz, 1H), 4.80-4.52 (m, 1H), 3.97-3.77 (m, 0.5H), 3.66-3.52 (m, 0.5H), 3.52-3.34 (m, 3H), 2.97-2.76 (m, 2H), 2.76-2.59 (m, 1H), 2.19-2.00 (m, 1H).

N-((7S)-9-Methyl-8-oxo-2-(4,4,4-trifluoro-3-hydroxy-3-methylbut-1-yn-1-yl)-6,7,8,9-tetrahydro-5H-pyrido[2,3-b]azepin-7-yl)-4-phenoxypicolinamide (I-56)

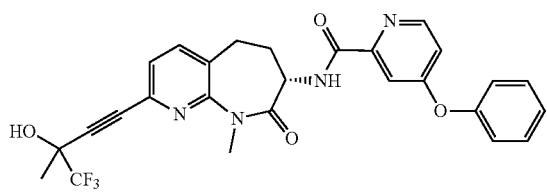 [SMILES: CN1C(=O)[C@@H](NC(=O)c2cc(Oc3ccccc3)ccn2)CCc2ccc(C#CC(C)(O)C(F)(F)F)nc21]

MS (ESI, m/z) Calculated 524.1671; Found [M+1]$^+$525.2. $^1$H NMR (400 MHz, Chloroform-d) δ (ppm) 8.97 (dd, J=12.6, 7.2 Hz, 1H), 8.43 (d, J=5.6 Hz, 1H), 7.64-7.54 (m, 2H), 7.46-7.35 (m, 2H), 7.32-7.18 (m, 2H), 7.10-7.01 (m, 2H), 6.96-6.87 (m, 1H), 4.64 (ddt, J=20.4, 11.3, 7.1 Hz, 1H), 3.55-3.39 (m, 3.5H), 3.23 (s, 0.5H), 2.93-2.76 (m, 2H), 2.75-2.63 (m, 1H), 2.19-1.98 (m, 1H), 1.74 (s, 3H).

(S)—N-(2-((3,3-Difluoro-1-hydroxycyclobutyl)ethynyl)-9-methyl-8-oxo-6,7,8,9-tetrahydro-5H-pyrido[2,3-b]azepin-7-yl)-4-phenoxypicolinamide (I-57)

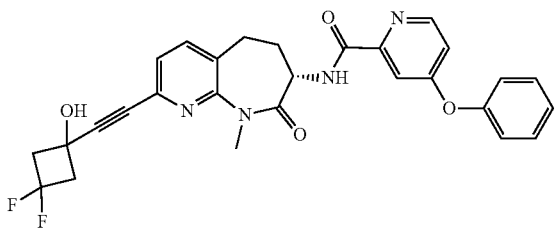 [SMILES: CN1C(=O)[C@@H](NC(=O)c2cc(Oc3ccccc3)ccn2)CCc2ccc(C#CC3(O)CC(F)(F)C3)nc21]

MS (ESI, m/z) Calculated 518.1766; Found [M+1]$^+$519.1. $^1$H NMR (400 MHz, Chloroform-d) δ (ppm) 8.95 (d, J=7.3 Hz, 1H), 8.43 (dd, J=5.6, 0.6 Hz, 1H), 7.62 (dd, J=2.6, 0.5 Hz, 1H), 7.58 (d, J=7.7 Hz, 1H), 7.45-7.37 (m, 2H), 7.27 (d, J=5.2 Hz, 1H), 7.26-7.21 (m, 1H), 7.10-7.04 (m, 2H), 6.93 (dd, J=5.6, 2.5 Hz, 1H), 4.61 (dt, J=11.1, 7.1 Hz, 1H), 3.52 (s, 3H), 3.29-3.14 (m, 2H), 3.07-2.92 (m, 2H), 2.84 (dtd, J=15.2, 7.5, 5.6 Hz, 2H), 2.75-2.59 (m, 1H), 2.19-2.03 (m, 1H).

(S)—N-(9-Methyl-2-(oxetan-3-ylethynyl)-8-oxo-6,7,8,9-tetrahydro-5H-pyrido[2,3-b]azepin-7-yl)-4-phenoxypicolinamide (I-58)

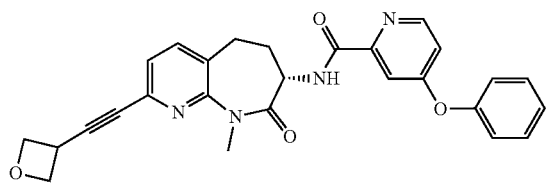 [SMILES: CN1C(=O)[C@@H](NC(=O)c2cc(Oc3ccccc3)ccn2)CCc2ccc(C#CC3COC3)nc21]

MS (ESI, m/z) Calculated 468.1798; Found [M+1]$^+$469.1. $^1$H NMR (400 MHz, Chloroform-d) δ (ppm) 8.94 (d, J=7.3 Hz, 1H), 8.43 (dd, J=5.6, 0.5 Hz, 1H), 7.62 (dd, J=2.5, 0.5 Hz, 1H), 7.56 (d, J=7.7 Hz, 1H), 7.45-7.35 (m, 2H), 7.27-7.22 (m, 3H), 7.10-7.04 (m, 2H), 6.93 (dd, J=5.6, 2.6 Hz, 1H), 4.92-4.79 (m, 4H), 4.60 (dt, J=11.2, 7.3 Hz, 1H), 4.12 (tt, J=8.5, 7.4 Hz, 1H), 3.52 (s, 3H), 2.94-2.73 (m, 2H), 2.73-2.61 (m, 1H), 2.19-2.03 (m, 1H).

(S)—N-(2-(3,3-Difluoro-3-(oxetan-3-yl)prop-1-yn-1-yl)-9-methyl-8-oxo-6,7,8,9-tetrahydro-5H-pyrido[2,3-b]azepin-7-yl)-4-phenoxypicolinamide (I-59)

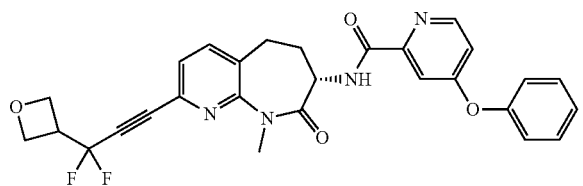 [SMILES: CN1C(=O)[C@@H](NC(=O)c2cc(Oc3ccccc3)ccn2)CCc2ccc(C#CC(F)(F)C3COC3)nc21]

MS (ESI, m/z) Calculated 518.1766; Found [M+1]$^+$519.1. $^1$H NMR (400 MHz, Chloroform-d) δ (ppm) 8.93 (d, J=7.3 Hz, 1H), 8.44 (d, J=5.6 Hz, 1H), 7.65-7.59 (m, 2H), 7.45-7.35 (m, 3H), 7.26-7.20 (m, 1H), 7.10-7.04 (m, 2H), 6.94 (dd, J=5.6, 2.5 Hz, 1H), 4.90-4.74 (m, 4H), 4.59 (dt, J=11.3, 7.2 Hz, 1H), 3.83-3.62 (m, 1H), 3.53 (s, 3H), 2.96-2.76 (m, 2H), 2.72 (dd, J=11.9, 6.2 Hz, 1H), 2.20-2.06 (m, 1H).

N-((7S)-2-(3-Amino-4,4,4-trifluoro-3-methylbut-1-yn-1-yl)-9-methyl-8-oxo-6,7,8,9-tetrahydro-5H-pyrido[2,3-b]azepin-7-yl)-4-phenoxypicolinamide (I-60)

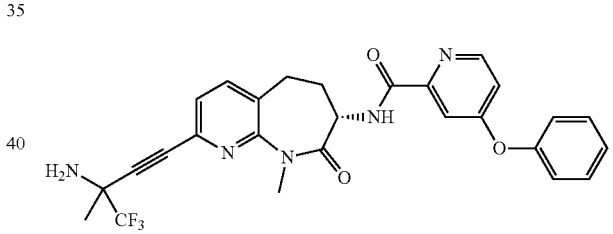

MS (ESI, m/z) Calculated 523.1831; Found [M+1]$^+$524.1. $^1$H NMR (400 MHz, Chloroform-d) δ (ppm) 8.93 (d, J=7.3 Hz, 1H), 8.43 (dd, J=5.6, 0.6 Hz, 1H), 7.62 (dd, J=2.6, 0.5 Hz, 1H), 7.57 (d, J=7.7 Hz, 1H), 7.44-7.37 (m, 2H), 7.30-7.21 (m, 2H), 7.09-7.04 (m, 2H), 6.93 (dd, J=5.6, 2.5 Hz, 1H), 4.58 (dt, J=11.1, 7.2 Hz, 1H), 3.52 (s, 3H), 2.93-2.75 (m, 2H), 2.75-2.63 (m, 1H), 2.17-2.02 (m, 1H), 2.02-1.81 (m, 2H), 1.67 (d, J=0.9 Hz, 3H).

(S)-5-Benzyl-N-(5-methyl-4-oxo-2,3,4,5-tetrahydropyrido[3,2-b][1,4]oxazepin-3-yl)-4H-1,2,4-triazole-3-carboxamide (I-1)

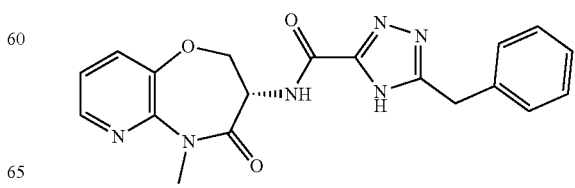

¹H NMR (400 MHz, CD₂Cl₂) δ8.30 (dd, J=4.7, 1.6 Hz, 1H), 8.06 (d, J=7.0 Hz, 1H), 7.53 (dd, J=8.0, 1.6 Hz, 1H), 7.32-7.21 (m, 5H), 7.18 (dd, J=8.0, 4.7 Hz, 1H), 4.99 (dt, J=11.3, 7.0 Hz, 1H), 4.76 (dd, J=9.8, 7.1 Hz, 1H), 4.32 (dd, J=11.3, 9.8 Hz, 1H), 4.17 (d, J=2.1 Hz, 2H), 3.49 (s, 3H). HRMS (TOFMS ES+) exact mass $C_{19}H_{18}N_6O_3$ 378.1440, found 379.1566.

(S)-5-Benzyl-N-(5-methyl-4-oxo-2,3,4,5-tetrahydro-pyrido[3,2-b][1,4]oxazepin-3-yl)-1,3,4-oxadiazole-2-carboxamide (I-2)

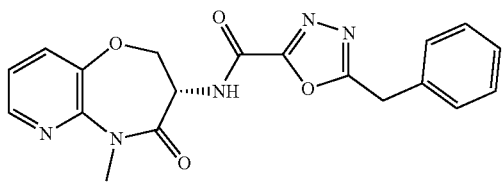 [SMILES: CN1C(=O)[C@@H](NC(=O)c2nnc(Cc3ccccc3)o2)COc2cccnc21]

MS (ESI, m/e) Calculated 379.1281; Found 380.0 $[M+H]^+$.

(S)-5-Benzyl-N-(8-(3-hydroxy-3-methylbut-1-yn-1-yl)-5-methyl-4-oxo-2,3,4,5-tetrahydro-pyrido[3,2-b][1,4]oxazepin-3-yl)-4H-1,2,4-triazole-3-carboxamide (I-3)

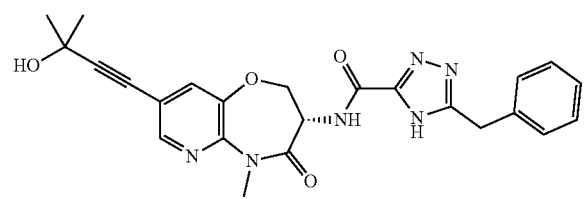 [SMILES: CN1C(=O)[C@@H](NC(=O)c2nnc(Cc3ccccc3)[nH]2)COc2cc(C#CC(C)(C)O)cnc21]

MS (ESI, m/e) Calculated 460.1859; Found 443.1 $[M-H_2O+H]^+$.

(S)-5-Benzyl-N-(5-methyl-8-(3-morpholinoprop-1-yn-1-yl)-4-oxo-2,3,4,5-tetrahydropyrido[3,2-b][1,4]oxazepin-3-yl)-1,3,4-oxadiazole-2-carboxamide (I-5)

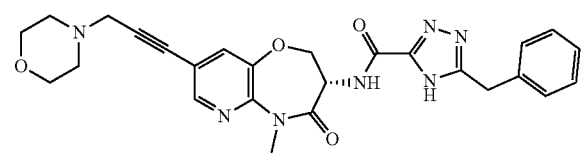 [SMILES: CN1C(=O)[C@@H](NC(=O)c2nnc(Cc3ccccc3)[nH]2)COc2cc(C#CCN3CCOCC3)cnc21]

MS (ESI m e) Calculated 502.1965; Found 503.1 $[M+H]^+$.

Synthesis of (S)-3-Amino-8-bromo-5-methyl-2,3-dihydropyrido[3,2-b][1,4]oxazepin-4 (5H)-one Hydrochloride (I-6)

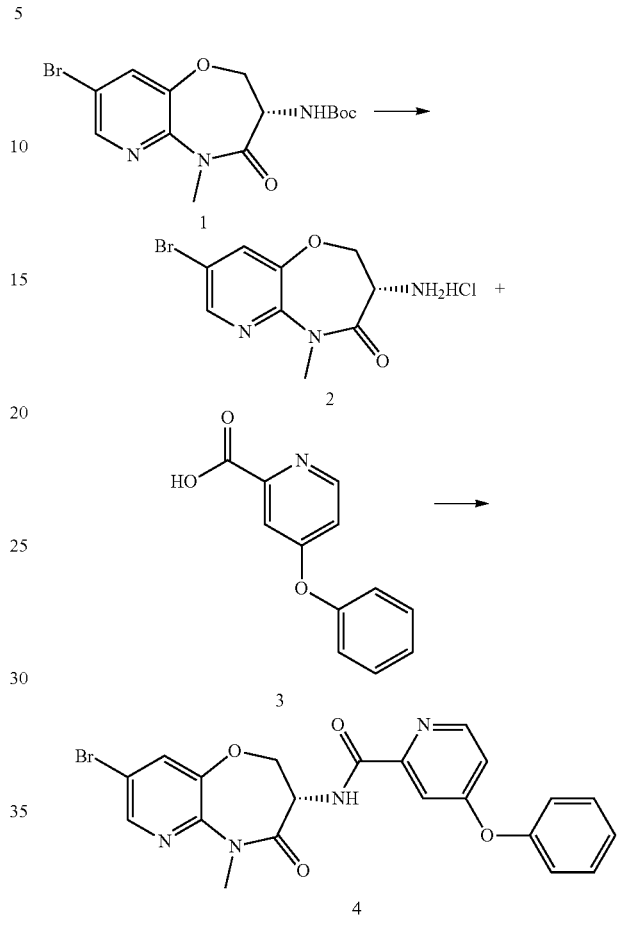

The 8-bromo compound illustrated in the scheme above as structure 4 is compound I-6 of the present disclosure. Compound I-6, in addition to exhibiting RIP1K inhibitory activity, is useful as an intermediate for synthesizing 8-substituted pyridoxazepines. For example, compound I-6 can be cross-coupled, for example under palladium catalyzed conditions with amino moieties as well as unsaturated groups as is known to those of skill in the art.

Hydrogen chloride solution (1 mL, 4M in dioxane, 4 mmol) was added to a vial containing tert-butyl (S)-(8-bromo-5-methyl-4-oxo-2,3,4,5-tetrahydropyrido[3,2-b][1,4]oxazepin-3-yl)carbamate 1 (prepared as described in WO2020239074, 52 mg, 0.139 mmol). The resulting solution was stirred at ambient temperature for 19 hrs. All solvents were removed under reduced pressure to afford (S)-3-amino-8-bromo-5-methyl-2,3-dihydropyrido[3,2-b][1,4]oxazepin-4 (5H)-one hydrochloride 2 (43 mg, 100%) as a white solid. MS (ESI, m/e) Calculated 270.9956; Found 272.0 $[M+H]^+$.

Synthesis of (S)—N-(8-Bromo-5-methyl-4-oxo-2,3,4,5-tetrahydropyrido[3,2-b][1,4]oxazepin-3-yl)-4-phenoxypicolinamide (4)

To a solution of (S)-3-amino-8-bromo-5-methyl-2,3-dihydropyrido[3,2-b][1,4]oxazepin-4 (5H)-one hydrochloride 2 (43 mg, 86 μmol) and 4-phenoxypicolinic acid 3 (45 mg, 0.21 mmol) in anhydrous DMF (1.4 mL) was added diisopropylethylamine (135 mg, 0.18 mL, 1.1 mmol) followed by HATU (80 mg, 0.21 mmol). The resulting solution was stirred at ambient temperature for 16 hrs. Water (0.1 mL) was then added, and the solution was directly purified by reverse HPLC using a gradient of 37 to 90% acetonitrile in water buffered with 0.1% formic acid. The desired fractions were combined, diluted with ethyl acetate (100 mL) and the resulting solution was washed with saturated sodium bicarbonate solution, brine, dried over anhydrous magnesium sulfate, filtered and concentrated under reduced pressure to afford (S)—N-(8-bromo-5-methyl-4-oxo-2,3,4,5-tetrahydropyrido[3,2-b][1,4]oxazepin-3-yl)-4-phenoxypicolinamide 4 (50 mg, 77%) as a white solid. MS (ESI, m/e) Calculated 468.0433; Found 468.9 [M+H]$^+$.

(S)—N-(8-Bromo-5-methyl-4-oxo-2,3,4,5-tetrahydropyrido[3,2-b][1,4]oxazepin-3-yl)-4-phenoxypicolinamide (I-6)

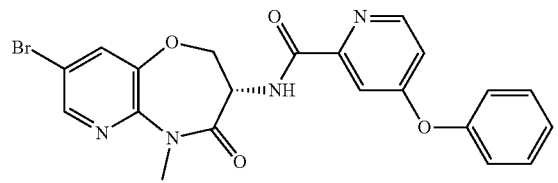 [SMILES: CN1C(=O)[C@@H](NC(=O)c2cc(Oc3ccccc3)ccn2)COc2cc(Br)cnc21]

MS (ESI, m/e) Calculated 468.0433; Found 468.9 [M+H]$^+$. (I-6)

(S)—N-(8-(3-Hydroxy-3-methylbut-1-yn-1-yl)-5-methyl-4-oxo-2,3,4,5-tetrahydropyrido[3,2-b][1,4]oxazepin-3-yl)-4-phenoxypicolinamide (I-7)

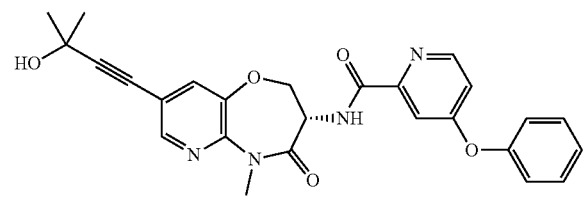 [SMILES: CN1C(=O)[C@@H](NC(=O)c2cc(Oc3ccccc3)ccn2)COc2cc(C#CC(C)(C)O)cnc21]

MS (ESI, m/e) Calculated 472.1747; Found 473.1 [M+H]$^+$.

(S)—N-(7-(3-hydroxy-3-methylbut-1-yn-1-yl)-5-methyl-4-oxo-2,3,4,5-tetrahydropyrido[3,2b][1,4]oxazepin-3-yl)-4-phenoxypicolinamide (I-18)

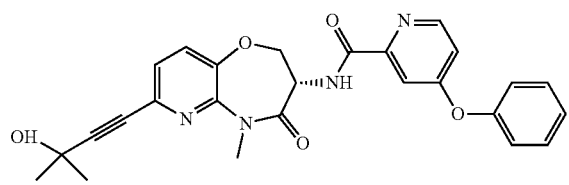 [SMILES: CN1C(=O)[C@@H](NC(=O)c2cc(Oc3ccccc3)ccn2)COc2ccc(C#CC(C)(C)O)nc21]

MS (ESI, m/z) Calculated 472.1747; Found [M+1]$^+$473.1. $^1$H NMR (400 MHz, Methanol-d$_4$) δ (ppm) 8.52 (dd, J=5.7, 0.5 Hz, 1H), 7.61 (d, J=8.1 Hz, 1H), 7.52-7.44 (m, 3H), 7.36 (d, J=8.2 Hz, 1H), 7.34-7.27 (m, 1H), 7.17-7.12 (m, 2H), 7.09 (dd, J=5.6, 2.6 Hz, 1H), 5.00 (dd, J=11.5, 7.0 Hz, 1H), 4.69 (dd, J=9.8, 7.0 Hz, 1H), 4.49 (dd, J=11.5, 9.8 Hz, 1H), 3.46 (s, 3H), 1.57 (s, 6H).

(S)—N-(7-((3,3-difluoro-1-hydroxycyclobutyl)ethynyl)-5-methyl-4-oxo-2,3,4,5-tetrahydropyrido [3,2-b][1,4]oxazepin-3-yl)-4-phenoxypicolinamide (I-30)

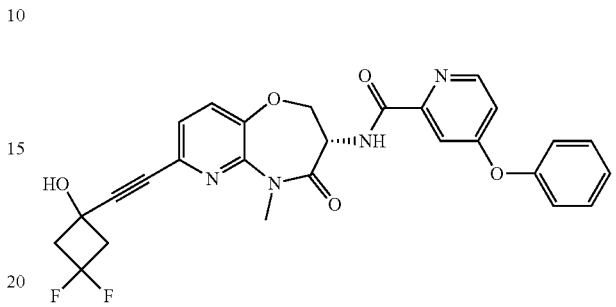

MS (ESI, m/z) Calculated 520.1558; Found [M+1]$^+$521.1. $^1$H NMR (400 MHz, Chloroform-d) δ (ppm) 8.97 (d, J=6.9 Hz, 1H), 8.45 (d, J=5.6 Hz, 1H), 7.61 (d, J=2.5 Hz, 1H), 7.48 (d, J=8.1 Hz, 1H), 7.46-7.39 (m, 2H), 7.29 (d, J=8.1 Hz, 1H), 7.24 (t, J=1.2 Hz, 1H), 7.11-7.04 (m, 2H), 6.96 (dd, J=5.6, 2.5 Hz, 1H), 5.09 (dt, J=11.4, 6.8 Hz, 1H), 4.81 (dd, J=9.7, 6.8 Hz, 1H), 4.36 (dd, J=11.4, 9.7 Hz, 1H), 3.50 (s, 3H), 3.22 (tdd, J=11.9, 9.3, 3.7 Hz, 2H), 3.08-2.86 (m, 3H).

(S)—N-(7-(4-hydroxy-3,3-dimethylbut-1-yn-1-yl)-5-methyl-4-oxo-2,3,4,5-tetrahydropyrido[3,2-b][1,4] oxazepin-3-yl)-4-phenoxypicolinamide (I-31)

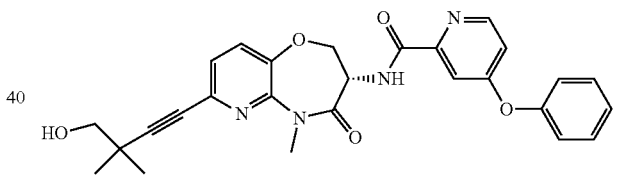

MS (ESI, m/z) Calculated 486.1903; Found [M+1]$^+$487.1. $^1$H NMR (400 MHz, Chloroform-d) δ (ppm) 8.92 (d, J=7.0 Hz, 1H), 8.44 (d, J=5.6 Hz, 1H), 7.61 (d, J=2.5 Hz, 1H), 7.47-7.37 (m, 3H), 7.28 (d, J=1.1 Hz, 1H), 7.25 (d, J=5.9 Hz, 1H), 7.10-7.04 (m, 2H), 6.96 (dd, J=5.6, 2.5 Hz, 1H), 5.00 (dt, J=11.4, 7.0 Hz, 1H), 4.78 (dd, J=9.7, 7.0 Hz, 1H), 4.34 (dd, J=11.4, 9.7 Hz, 1H), 3.54 (s, 2H), 3.53 (s, 3H), 1.34 (s, 6H).

(S)—N-(7-(4-Hydroxy-3,3-dimethylbut-1-yn-1-yl)-5-methyl-4-oxo-2,3,4,5-tetrahydro-benzo[b][1,4] oxazepin-3-yl)-4-phenoxypicolinamide (I-31)

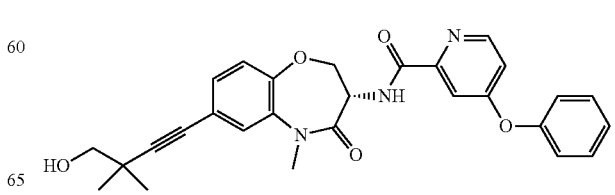

¹H NMR (400 MHz, CD₂Cl₂) δ8.74 (d, J=7.2 Hz, 1H), 8.47 (dd, J=5.6, 0.5 Hz, 1H), 7.56 (dd, J=2.6, 0.5 Hz, 1H), 7.49-7.40 (m, 2H), 7.31-7.25 (m, 3H), 7.14-7.08 (m, 3H), 6.98 (dd, J=5.6, 2.6 Hz, 1H), 4.97 (dt, J=11.2, 7.3 Hz, 1H), 4.69 (dd, J=9.7, 7.3 Hz, 1H), 4.25 (dd, J=11.3, 9.7 Hz, 1H), 3.48 (s, 2H), 3.40 (s, 3H), 1.87 (s, 1H), 1.29 (s, 6H). HRMS (TOFMS ES+) exact mass $C_{28}H_{27}N_3O_5$ 485.1951, found 486.2024.

(S)—N-(8-(4-Hydroxy-3,3-dimethylbut-1-yn-1-yl)-5-methyl-4-oxo-2,3,4,5-tetrahydropyrido[3,2-b][1,4]oxazepin-3-yl)-4-phenoxypicolinamide (I-8)

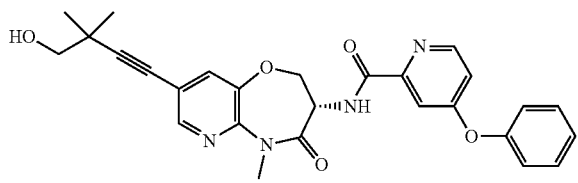 [SMILES: CN1C(=O)[C@@H](NC(=O)c2cc(Oc3ccccc3)ccn2)COc2cc(C#CC(C)(C)CO)cnc21]

¹H NMR (400 MHz, CDCl₃) δ 8.91 (d, J=7.0 Hz, 1H), 8.44 (d, J=5.6 Hz, 1H), 8.30 (d, J=1.9 Hz, 1H), 7.62 (d, J=2.5 Hz, 1H), 7.51 (d, J=2.0 Hz, 1H), 7.41 (td, J=8.9, 7.2 Hz, 2H), 7.27-7.24 (m, 1H), 7.12-7.03 (m, 2H), 6.95 (dd, J=5.6, 2.5 Hz, 1H), 5.00 (dt, J=11.4, 7.0 Hz, 1H), 4.76 (dd, J=9.7, 7.0 Hz, 1H), 4.34 (dd, J=11.4, 9.7 Hz, 1H), 3.54 (s, 2H), 3.51 (s, 3H), 1.91 (s, 1H), 1.33 (s, 6H). HRMS (TOFMS ES+) exact mass $C_{27}H_{26}N_4O_5$ 486.1903, found 487.1988.

(S)—N-(5-Methyl-4-oxo-8-(pyridin-2-ylethynyl)-2,3,4,5-tetrahydropyrido[3,2-b][1,4]oxazepin-3-yl)-4-phenoxypicolinamide (I-9)

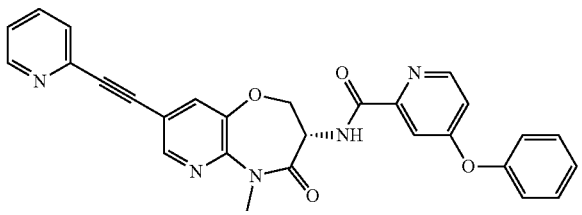 [SMILES: CN1C(=O)[C@@H](NC(=O)c2cc(Oc3ccccc3)ccn2)COc2cc(C#Cc3ccccn3)cnc21]

HRMS (TOFMS ES+) exact mass $C_{28}H_{21}N_5O_4$ 491.1594, found 492.1680.

Kinase Inhibition

In this example, compounds of the disclosure were evaluated using a biochemical assay using the ADP-Glo™ technology.

ADP-Glo™ (Promega, Madison, WI, USA) reagents were thawed at ambient temperature. Kinase Detection Reagent was prepared by mixing kinase detection buffer with the lyophilized kinase detection substrate.

A 500 ml stock volume of 5× Reaction Kinase Buffer was made by mixing 1000 μl of 1M MgCl₂, 500 μl of 1M Tris-HCL pH7.4, 0.5 mg/ml (25 mg) of BSA, and 3475 μl of distilled H₂O. A 3 ml 2× working stock volume of Reaction Kinase Buffer was made containing a final concentration of 100 μM DTT and 4 mM MnCl₂.

Components of RIPK1 enzyme (Rigel Pharmaceuticals, South San Francisco, CA, USA) were thawed on ice. Diluted RIPK1 was prepared in 1× Kinase Reaction Buffer (diluted from 2× buffer) to 31 ng/well. A 166 μM working stock ATP assay solution was prepared in 1× Kinase Reaction Buffer (diluted from 2× buffer).

Compounds were serially diluted in DMSO from 250 uM in 4-fold dilutions then diluted 1:5 in 2× Reaction Buffer in a 96 well plate. 1.0 ul of diluted compound was added to a 384 well plate in duplicate. 2 μl of diluted Active RIPK1 was added to 384 well plate (do not add to column1) add 2×rxn buffer to column 1. AKT (Anaspec, Fremont, CA, USA) at 150 nM was combined with ATP working stock at equal volume and 2 ul/well were added to the 384 well plate. The final reaction volume was 5.0 μl.

The plate was quickly centrifuged and the reaction was incubated at 30° C. for 30 minutes. Adding 5 μl of ADP-Glo™ terminated the reaction. The plate was quickly centrifuged and the reaction was incubated at room temperature for 40 minutes. Kinase Detection Reagent was then added and incubated at room temperature for 30 minutes. The relative light unit (RLU) of kinase reaction was determined by luminescent (Luminescence 0.1 s) using a Wallac Victor2 Luminometer (PerkinElmer, Waltham, MA, USA). $IC_{50}$ values obtained from this example are provided by Table 1.

TABLE 1

| Compound | RIPK1 ADP-Glo Kinase (IC$_{50}$) |
|---|---|
| I-1 | 0.0375 |
| I-2 | 0.038 |
| I-3 | 0.0627 |
| I-4 | 0.0229 |
| I-5 | 0.0728 |
| I-6 | 0.0221 |
| I-7 | 0.0693 |
| I-8 | 0.034 |
| I-9 | 1.845 |
| I-10 | 0.0538 |
| I-11 | 12.03 |
| I-12 | 0.1482 |
| I-13 | 0.0257 |
| I-14 | 3.723 |
| I-15 | 0.2192 |
| I-16 | 6.255 |
| I-17 | 0.024 |
| I-18 | 0.0227 |
| I-19 | 0.0162 |
| I-20 | 0.0099 |
| I-21 | 0.023 |
| I-22 | 0.0172 |
| I-23 | 0.0261 |
| I-24 | 0.0291 |
| I-25 | 0.1104 |
| I-26 | 0.0265 |
| I-27 | 0.026 |
| I-28 | 0.0188 |
| I-29 | 0.0211 |
| I-30 | 0.0179 |
| I-31 | 0.0196 |
| I-32 | 0.0381 |
| I-33 | 0.013 |
| I-34 | 0.0269 |
| I-35 | 0.0201 |
| I-36 | 0.0335 |
| I-37 | 0.0377 |
| I-38 | 0.0208 |
| I-39 | 0.0217 |
| I-40 | 0.012 |
| I-41 | 0.0189 |
| I-42 | 0.018 |
| I-43 | 0.0112 |
| I-44 | 0.0116 |
| I-45 | 0.0598 |
| I-46 | 0.0108 |
| I-47 | 0.0321 |
| I-48 | 0.0344 |

TABLE 1-continued

| Compound | RIPK1 ADP-Glo Kinase ($IC_{50}$) |
|---|---|
| I-49 | 0.1097 |
| I-50 | 5.058 |
| I-51 | 0.0167 |
| I-52 | 0.0178 |
| I-53 | 0.0117 |
| I-54 | 0.1016 |
| I-55 | 0.0135 |
| I-56 | 0.0157 |
| I-57 | 0.0079 |
| I-58 | 0.0172 |
| I-59 | 0.0205 |
| I-60 | 0.0085 |

Whole Cell Assay Data

In this example, U937 and L929 cells were exposed to compounds of the present disclosure and a cell necroptosis assay was conducted to evaluate the compounds' activity against human RIP1 and murine RIP1.

U937 and L929 cells were obtained from the American Type Culture Collection (Manassa, VA, USA). Both cells were maintained in logarithmic growth phase in complete RPMI 1640 media (Sigma, ST Louis, MO, USA) supplemented with 10% fetal bovine serum (Sigma, ST Louis, MO, USA) at 37° C. with 5% $CO_2$. For necroptosis assay, L929 cells were plated for 18 h in 100 µL/well medium at 10K cells/well in Costar 96-well black clear-bottom plates (Fisher Scientific, Hampton, NH, USA); U937 cells were plated on the day of the assay in 50 µL/well medium containing 60 uM zVAD-fmk (Lonza, Basel, Switzerland) at 50K cells/well. Medium from L929 cells were removed from the 96-well plates and replaced with 50 µL/well new medium containing 40 uM zVAD-fmk. Each compound of the present disclosure evaluated in this example was serially diluted in DMSO from 2.5 mM in 4-fold dilutions, and then diluted 1:125 in complete medium. 50 µL/well 2× of the compound was then added to the cells in the plates. The cells were pre-incubated with the compound for 1 hour at 37° C. with 5% $CO_2$ and before addition of 10 µL/well 11× TNFa (Peprotech, Rocky Hill, NJ, USA) to give a final concentration of 2 ng/mL for TNFa. The relative amount of necroptosis cells was determined by luminescent using a Wallac Victor2 Luminometer (PerkinElmer, Waltham, MA, USA) and a CellTiter-Glo® Luminescent Cell Viability Reagent Assay (Promega, Madison, WI, USA) added per manufacturer instructions after 18 hours of TNFa stimulation at 37° C. with 5% $CO_2$. Results from this example are summarized in Table 2. This example establishes that embodiments of the compounds described herein have unexpectedly potent activity against human RIP1 and murine RIP1, which allows their assessment in in vivo mouse models of disease. These results are useful in determining safe and effective doses for humans.

TABLE 2

| Compound | L929-CTG-recovery, L929, TNFa + zVAD ($IC_{50}$) | U937 Zvad TNF CTG Recovery, U937, TNFa + zVAD ($IC_{50}$) |
|---|---|---|
| I-1 | 2.197 | 0.0054 |
| I-2 | 1.735 | 0.0088 |
| I-3 | 0.7303 | 0.0114 |
| I-4 | 0.5818 | 0.0452 |
| I-5 | 0.848 | 0.0025 |
| I-6 | 0.2323 | 0.0024 |
| I-7 | 1.004 | 0.0022 |
| I-8 | 0.5385 | 0.0033 |
| I-9 | 14.67 | 0.514 |
| I-10 | 0.8896 | 0.1658 |
| I-11 | 9999 | 9999 |
| I-12 | 12.65 | 0.0352 |
| I-13 | 4.111 | 0.0115 |
| I-14 | 9999 | 3.64 |
| I-15 | 7.396 | 19.19 |
| I-16 | 9999 | 7.11 |
| I-17 | 0.3923 | 0.0025 |
| I-18 | 0.8655 | 0.0043 |
| I-19 | 0.6463 | 0.0166 |
| I-20 | 0.7101 | 0.0024 |
| I-21 | 2.631 | 0.0097 |
| I-22 | 0.6688 | 0.0017 |
| I-23 | 2.354 | 0.0023 |
| I-24 | 0.6616 | 0.003 |
| I-25 | 8.816 | 0.0273 |
| I-26 | 0.3244 | 0.0013 |
| I-27 | 9.421 | 0.0706 |
| I-28 | 1.553 | 0.0067 |
| I-29 | 0.626 | 0.0027 |
| I-30 | 0.6477 | 0.001 |
| I-31 | 2.197 | 0.0054 |
| I-32 | 1.735 | 0.0088 |
| I-33 | 0.204 | 0.0014 |
| I-34 | 0.2158 | 0.0063 |
| I-35 | 0.7077 | 0.0114 |
| I-36 | 0.0159 | 0.0009 |
| I-37 | 0.0318 | 0.0034 |
| I-38 | 0.0066 | 0.0021 |
| I-39 | 4.199 | 0.021 |
| I-40 | 0.7748 | 0.0276 |
| I-41 | 0.3381 | 0.0033 |
| I-42 | 0.9114 | 0.0196 |
| I-43 | 0.3231 | 0.0036 |
| I-44 | 0.0597 | 0.0011 |
| I-45 | 0.9454 | 0.0162 |
| I-46 | 0.1986 | 0.0027 |
| I-47 | 0.0065 | 0.0003 |
| I-48 | 3.403 | 0.0543 |
| I-49 | 30.3 | 0.2435 |
| I-50 | 67.61 | 6.142 |
| I-51 | 5.134 | 0.0874 |
| I-52 | 0.0475 | 0.0128 |
| I-53 | 0.0221 | 0.0057 |
| I-54 | 0.4367 | 0.0128 |
| I-55 | 0.0755 | 0.0045 |
| I-56 | 0.0582 | 0.0041 |
| I-57 | 0.1357 | 0.008 |
| I-58 | 0.0813 | 0.003 |
| I-59 | 0.0582 | 0.0056 |
| I-60 | 0.2034 | 0.0057 |

Acute In Vivo Assay

In this example, an acute hypothermia mouse model assay was used to evaluate the ability of compounds disclosed herein to inhibit TNF-alpha induced hypothermia.

Female C57BL/6 mice are randomly grouped and weighed on Day −1. On the day of the study (Day 0), mice are administered vehicle or test article by oral gavage. Fifteen minutes after oral administration of test agents, each mouse is administered an intraperitoneal (IP) injection of solution containing recombinant human tumor necrosis factor alpha (TNF-α, 25.0 µg) and zVAD-FMK (200 µg). Body temperature is measured at 0 hours (before IP injections) and every hour via rectal probe temperature measuring device. Three (3) hours after IP injections of TNF-α and zVAD/

FMK, mice are euthanized by $CO_2$ asphyxiation and blood is collected via cardiac puncture. Serum and plasma are harvested for determination of cytokine and compound levels, respectively. Separate groups of mice (satellite mice) are included for the determination of compound levels in plasma at the time of administration of TNFa/zVAD-FMK. Compounds of the present disclosure inhibited TNF-alpha induced hypothermia.

Brain Penetration

Certain embodiments of the invention provide for compound, compounds or compositions thereof to traverse the blood-brain barrier. Disclosed compound and composition embodiments exhibit sufficient brain penetration as potential therapeutics in neurological diseases. Brain penetration may be assessed by evaluating brain/plasma ratio (B/P) as measured through in vivo pharmacokinetic studies in rodents and determining free fraction in rodent brain in vitro. By way of example compound I-44 exhibited a B/P ratio of 1.6 and compound I-58 exhibited a B/P ratio of 0.44. Other examples exhibited higher partition ratios. Without being limited to theory, it is believed that compounds with higher brain/plasma partition ratios may be more pharmacologically active against neurological disorders. Other methods for assessing brain penetration are known to persons of ordinary skill in the art. See, for example, Liu, X. et al., J. Pharmacol. Exp. Therap., 325:349-56, 2008. *II-MDR1 Permeability*. In this method, the passive membrane permeability (Papp) and the P-gp (P-glycoprotein) substrate efflux potential are determined using a MDCKII-MDR1 cell line as an in vitro model of the effective permeability of a compound through the BBB. Compounds with an MDCKII-MDR1 efflux ratio of less than or equal to 2.5 are likely to demonstrate ability to cross the blood-brain-barrier.

Brain free fraction is a predictive marker for assessing potential for potential therapeutics in the CNS. See, Read K. D.; Braggio S. Assessing brain free fraction in early drug discovery. *Expert. Opin. Drug. Metab. Toxicol.* 2010, 6, 337-344.

Accordingly, the brain free fraction for representative compounds is provided in Table 3:

TABLE 3

| Compound | % Unbound |
|---|---|
| I-18 | 2.7 |
| I-21 | 2.19 |
| I-33 | 0.57 |
| I-44 | 1.70 |
| I-46 | 0.89 |
| I-56 | 0.93 |
| I-58 | 1.84 |

Determination of brain free fraction is known such that those of skill in the art could determine the brain free fraction for additional compounds disclosed herein. See, Srinivas, Nithya et al. "*Clinical Pharmacokinetics* and Pharmacodynamics of Drugs in the Central Nervous System." *Clinical pharmacokinetics* vol. 57, 9 (2018): 1059-1074. doi: 10.1007/s40262-018-0632-y. The brain free fraction reported in Table 3 indicates that exemplary compounds exhibit characteristics of CNS-active compounds.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for treating a disease in a subject, comprising administering to the subject
   (i) a therapeutically effective amount of a compound of Formula I; or
   (ii) a therapeutically effective amount of a pharmaceutical composition comprising a compound of Formula I and one or more pharmaceutically acceptable excipient;
   wherein the subject has, or is suspected of having or developing, the disease, wherein the disease is a disease involving a receptor-interacting protein-1 (RIP1) kinase, wherein the disease involving a receptor-interacting protein-1 (RIP1) kinase is amyotrophic lateral sclerosis (ALS), type I diabetes, rheumatoid arthritis, Crohn's disease, ulcerative colitis, multiple sclerosis, asthma, or leukemia;
   wherein the compound of Formula I is

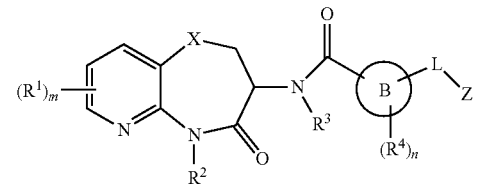

wherein
ring B is a 5-membered or 6-membered heteroaryl;
X is $CH_2$ or O;
L is a heteroatom or $R^a$, provided that $R^a$ is not hydrogen;
Z is $C_{1-10}$aliphatic, aryl, or heteroaryl, wherein the $C_{1-10}$aliphatic, aryl, or heteroaryl is optionally substituted with one or more $R^5$;
$R^1$ is independently for each occurrence —$NR^dR^d$ wherein the two $R^d$ groups together with the nitrogen bound thereto provide a $C_{3-10}$heterocyclic group; —C≡CH, or a -linker-$R^6$ group, wherein the linker is a divalent $C_{1-10}$aliphatic or $C_{1-10}$cycloaliphatic, and $R^6$ is $R^b$, —$C(R^f)_3$, or —$C(R^f)$=$C(R^f)_2$; $C_{5-10}$aromatic, or $C_{3-6}$heterocyclic, wherein each linker is optionally substituted with one or more halo, $R^a$, or both;
$R^2$ and $R^3$ independently are $R^a$;
$R^4$ and $R^5$ independently are, for each occurrence, $R^e$;
$R^a$ is independently for each occurrence hydrogen, $C_{1-10}$aliphatic, $C_{1-10}$haloaliphatic, $C_{5-10}$aromatic, or $C_{3-6}$heterocyclic;
$R^b$ is independently for each occurrence —OH, —SH, —$OR^c$, —$SR^c$, —$NR^eR^e$, —$Si(R^a)_3$, —C(O)OH, —$C(O)OR^c$, or —$C(O)NR^eR^e$
$R^c$ is independently for each occurrence $C_{1-10}$alkyl, $C_{2-10}$alkenyl, $C_{2-10}$alkynyl, $C_{3-6}$cycloalkyl, or $C_{5-10}$aromatic, wherein the $C_{1-10}$alkyl, $C_{2-10}$alkenyl, $C_{2-10}$alkynyl, $C_{3-6}$cycloalkyl, or $C_{5-10}$aromatic is optionally substituted with 1, 2, or 3 $R^e$;
$R^d$ is $C_{1-9}$aliphatic optionally substituted with 1, 2, or 3 groups selected from the group consisting of $R^a$, $R^b$ and $R^e$;
$R^e$ is independently for each occurrence oxo (═O), —$OR^a$, $N(R^a)_2$, halo, $C_{1-6}$alkyl, $C_{1-6}$haloalkyl, $C_{1-6}$heteroalkyl, $C_{3-6}$cycloalkyl, or two $R^e$ groups join together to provide a $C_{3-10}$heterocyclic group with a nitrogen to which the two $R^e$ groups are bound;

m is 1 to 4; and n is 0, 1 or 2.

2. The method of claim 1, wherein the disease involving a receptor-interacting protein-1 (RIP1) kinase is amyotrophic lateral sclerosis (ALS) or multiple sclerosis.

3. The method of claim 1, wherein the disease involving a receptor-interacting protein-1 (RIP1) kinase is rheumatoid arthritis, type I diabetes, Crohn's disease, ulcerative colitis, asthma, or leukemia.

4. A method for treating a disease in a subject, comprising administering to the subject (i) a therapeutically effective amount of a compound; or (ii) a therapeutically effective amount of a pharmaceutical composition comprising a compound and one or more pharmaceutically acceptable excipient;

wherein the subject has, or is suspected of having or developing, the disease, wherein the disease is a disease involving a receptor-interacting protein-1 (RIP1) kinase, wherein the disease involving a receptor-interacting protein-1 (RIP1) kinase is amyotrophic lateral sclerosis (ALS), type I diabetes, rheumatoid arthritis, Crohn's disease, ulcerative colitis, multiple sclerosis, asthma, or leukemia;

wherein the compound is

I-3

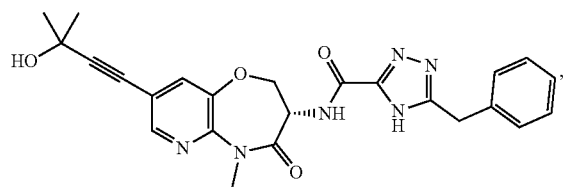

I-5

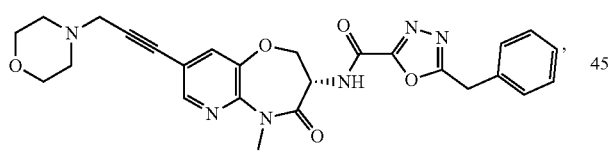

I-7

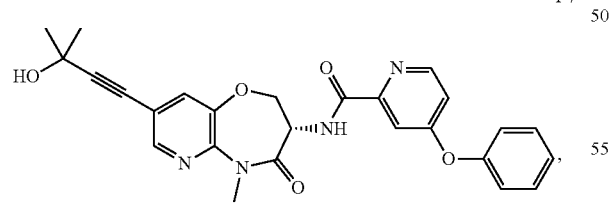

I-8

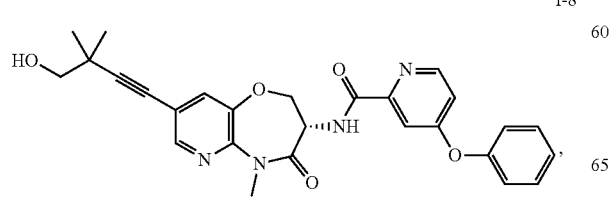

I-9

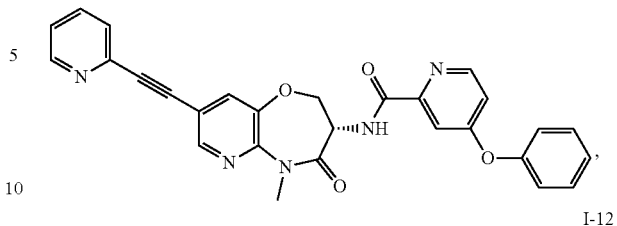

I-12

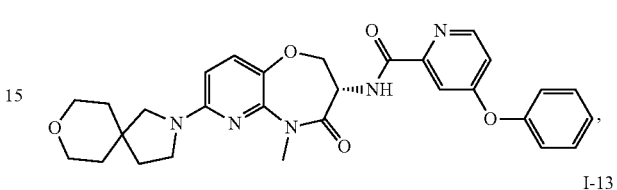

I-13

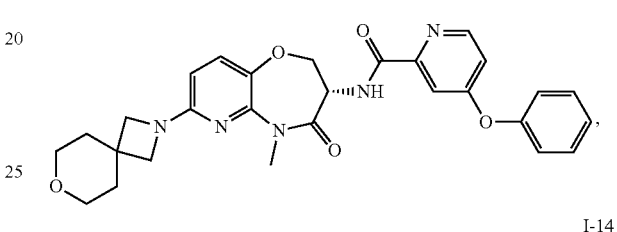

I-14

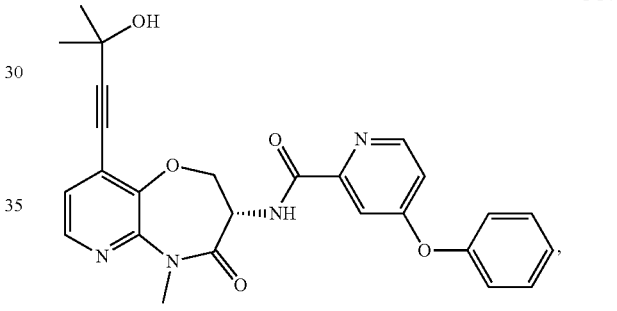

I-15

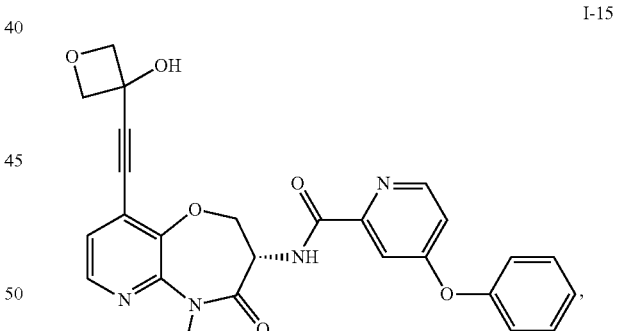

I-16

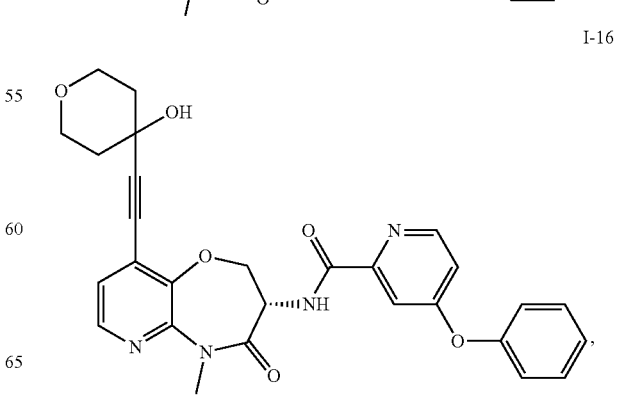

-continued

I-17

I-18

I-19

I-20

I-21

I-22

I-23

I-24

I-25

I-26

I-27

I-28

I-29

I-30

I-31
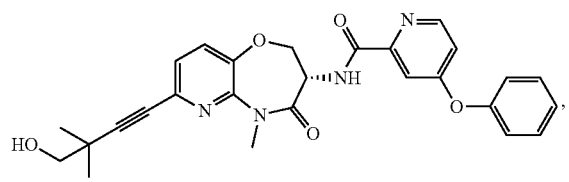
I-32
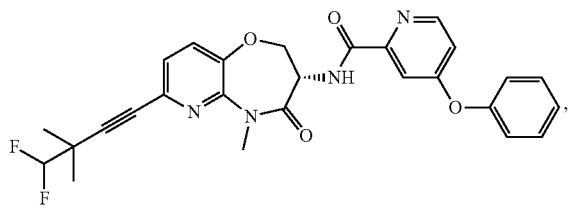
I-33
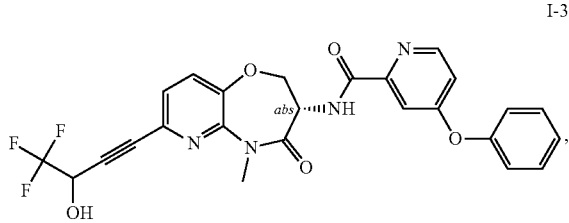
I-34
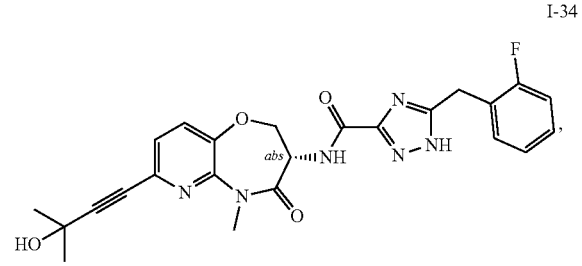
I-35
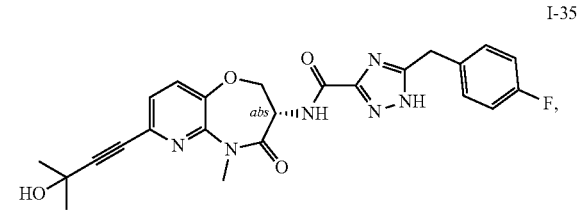
I-36
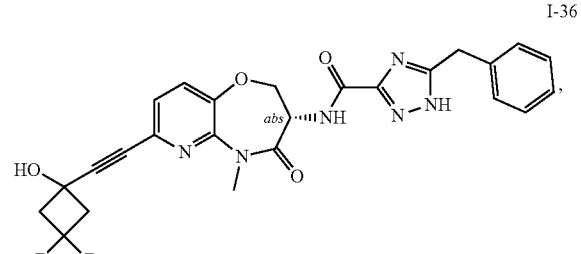
I-37
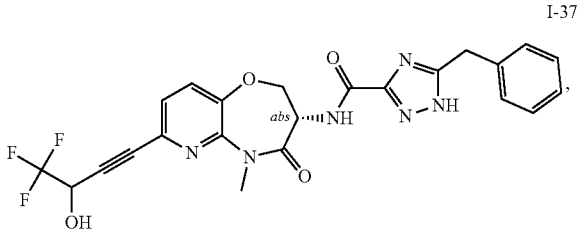
I-38
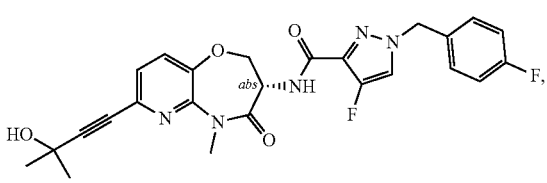
I-39
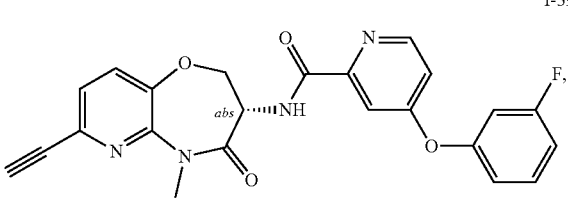
I-40
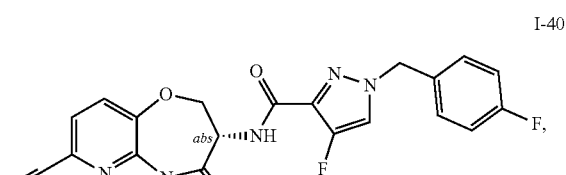
I-41
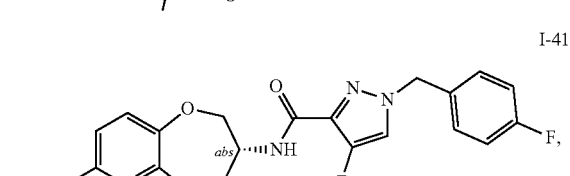
I-42
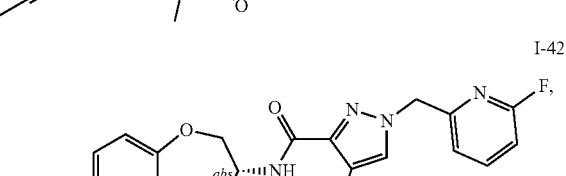
I-43
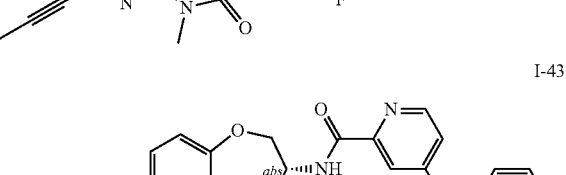
I-44
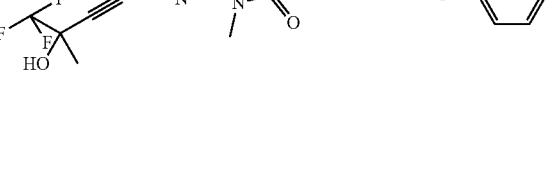
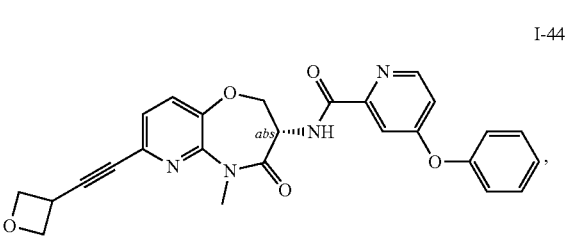

I-45
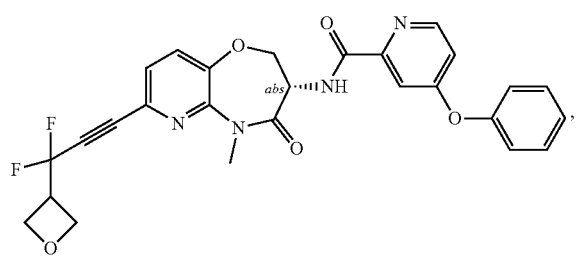
I-46
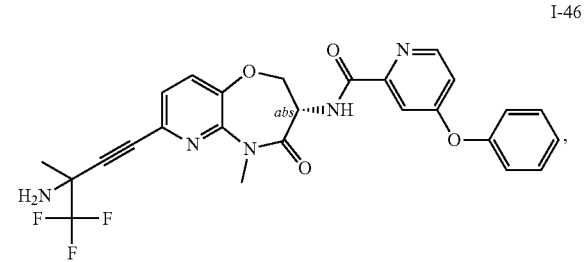
I-47
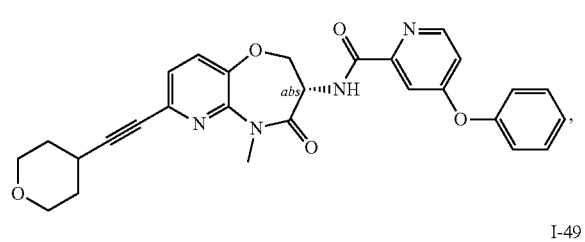
I-49
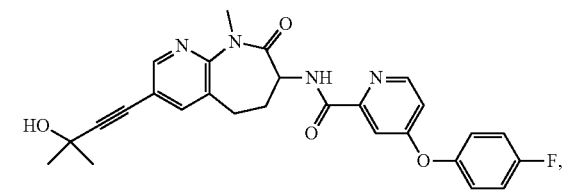
I-50
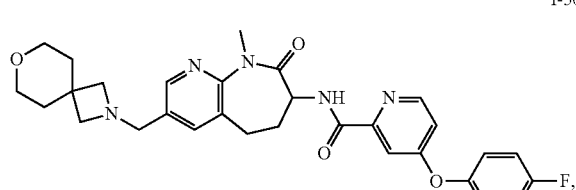
I-52
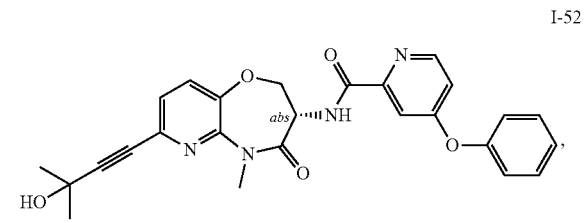
I-53
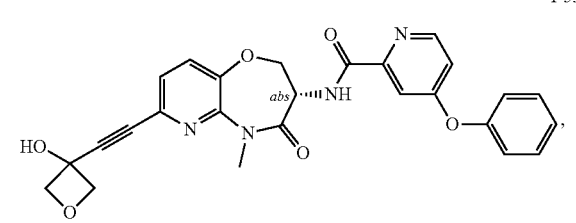
I-54
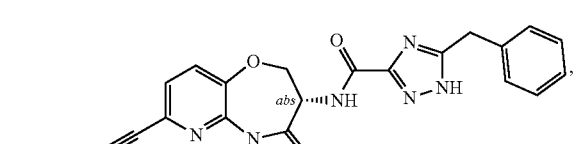
I-55
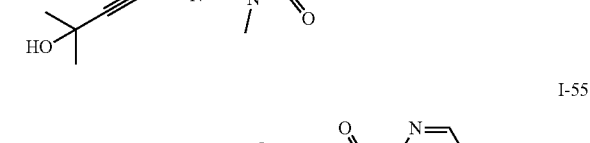
I-56
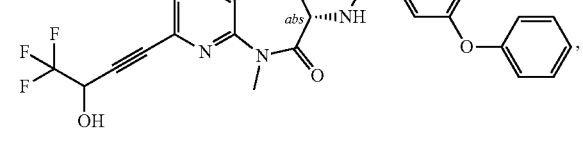
I-57
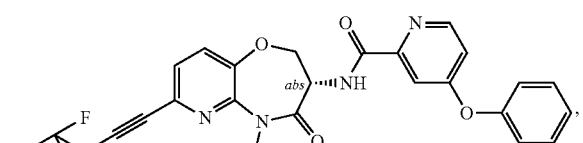
I-58
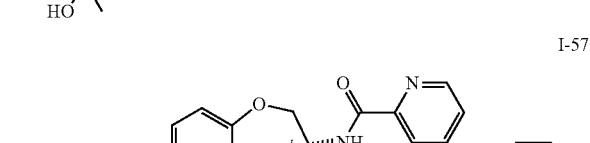
I-59
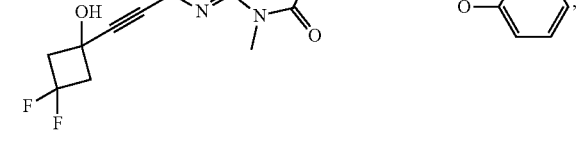
or
I-60
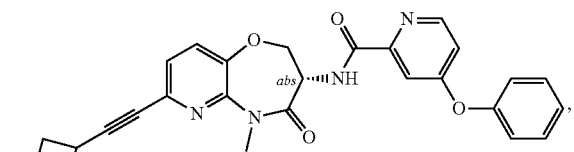

5. A method of inhibiting receptor-interacting protein-1 (RIP1) kinase in a subject, comprising administering to the subject
  (i) a therapeutically effective amount of a compound of Formula I; or
  (ii) a therapeutically effective amount of a pharmaceutical composition comprising a compound of Formula I and one or more pharmaceutically acceptable excipient;
wherein the compound of Formula I is

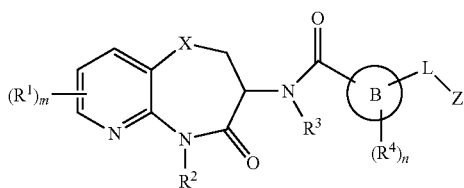

wherein
  ring B is a 5-membered or 6-membered heteroaryl;
  X is $CH_2$ or O;
  L is a heteroatom or $R^a$, provided that $R^a$ is not hydrogen;
  Z is $C_{1-10}$aliphatic, aryl, or heteroaryl, wherein the $C_{1-10}$aliphatic, aryl, or heteroaryl is optionally substituted with one or more $R^5$;
  $R^1$ is independently for each occurrence —$NR^dR^d$ wherein the two $R^d$ groups together with the nitrogen bound thereto provide a $C_{3-10}$heterocyclic group; —C≡CH, or a -linker-$R^6$ group, wherein the linker is a divalent $C_{1-10}$aliphatic or $C_{1-10}$cycloaliphatic, and $R^6$ is $R^b$, —$C(R^f)_3$, or —$C(R^f)$=$C(R^f)_2$; $C_{5-10}$aromatic, or $C_{3-6}$heterocyclic, wherein each linker is optionally substituted with one or more halo, $R^a$, or both;
  $R^2$ and $R^3$ independently are $R^a$;
  $R^4$ and $R^5$ independently are, for each occurrence, $R^e$;
  $R^a$ is independently for each occurrence hydrogen, $C_{1-10}$aliphatic, $C_{1-10}$haloaliphatic, $C_{5-10}$aromatic, or $C_{3-6}$heterocyclic;
  $R^b$ is independently for each occurrence —OH, —SH, —$OR^c$, —$SR^c$, —$NR^eR^e$, —$Si(R^a)_3$, —C(O)OH, —$C(O)OR^c$, or —$C(O)NR^eR^e$
  $R^c$ is independently for each occurrence $C_{1-10}$alkyl, $C_{2-10}$alkenyl, $C_{2-10}$alkynyl, $C_{3-6}$cycloalkyl, or $C_{5-10}$aromatic, wherein the $C_{1-10}$alkyl, $C_{2-10}$alkenyl, $C_{2-10}$alkynyl, $C_{3-6}$cycloalkyl, or $C_{5-10}$aromatic is optionally substituted with 1, 2, or 3 $R^e$;
  $R^d$ is $C_{1-9}$aliphatic optionally substituted with 1, 2, or 3 groups selected from the group consisting of $R^a$, $R^b$ and $R^e$;
  $R^e$ is independently for each occurrence oxo (=O), —$OR^a$, $N(R^a)_2$, halo, $C_{1-6}$alkyl, $C_{1-6}$haloalkyl, $C_{1-6}$heteroalkyl, $C_{3-6}$cycloalkyl, or two $R^e$ groups join together to provide a $C_{3-10}$heterocyclic group with a nitrogen to which the two $R^e$ groups are bound;
  m is 1 to 4; and
  n is 0, 1 or 2.

* * * * *